United States Patent
Lai et al.

(10) Patent No.: US 11,897,939 B2
(45) Date of Patent: Feb. 13, 2024

(54) COMPOSITIONS AND METHODS FOR INHIBITING PATHOGEN INFECTION

(71) Applicants: The University of North Carolina at Chapel Hill, Chapel Hill, NC (US); The Johns Hopkins University, Baltimore, MD (US)

(72) Inventors: Samuel Lai, Carrboro, NC (US); Ying-Ying Wang, San Francisco, CA (US); Arthi Kannan, Morrisville, NC (US); Kenetta Nunn, Moscow, ID (US); Durai Babu Subramani, Chapel Hill, NC (US); Richard Cone, Baltimore, MD (US); Bing Yang, Chapel Hill, NC (US); Justin Mccallen, Greenville, NC (US)

(73) Assignees: The University of North Carolina at Chapel Hill, Chapel Hill, NC (US); The Johns Hopkins University, Baltimore, MD (US)

( * ) Notice: Subject to any disclaimer, the term of this patent is extended or adjusted under 35 U.S.C. 154(b) by 477 days.

(21) Appl. No.: 17/066,874

(22) Filed: Oct. 9, 2020

(65) Prior Publication Data
US 2021/0061889 A1 Mar. 4, 2021

Related U.S. Application Data

(63) Continuation of application No. 16/138,643, filed on Sep. 21, 2018, now Pat. No. 10,829,543, which is a continuation-in-part of application No. 14/438,511, filed as application No. PCT/US2013/067328 on Oct. 29, 2013, now Pat. No. 10,100,102.

(60) Provisional application No. 62/646,220, filed on Mar. 21, 2018, provisional application No. 61/719,689, filed on Oct. 29, 2012.

(51) Int. Cl.
| | |
|---|---|
| *C07K 16/08* | (2006.01) |
| *A61P 31/22* | (2006.01) |
| *C07K 16/10* | (2006.01) |
| *A61P 31/14* | (2006.01) |
| *C07K 16/12* | (2006.01) |
| *A61P 11/00* | (2006.01) |
| *A61P 31/12* | (2006.01) |
| *A61K 39/00* | (2006.01) |

(52) U.S. Cl.
CPC ............ *C07K 16/087* (2013.01); *A61P 11/00* (2018.01); *A61P 31/12* (2018.01); *A61P 31/14* (2018.01); *A61P 31/22* (2018.01); *C07K 16/10* (2013.01); *C07K 16/1027* (2013.01); *C07K 16/1214* (2013.01); *A61K 2039/505* (2013.01); *A61K 2039/544* (2013.01); *C07K 2317/13* (2013.01); *C07K 2317/21* (2013.01); *C07K 2317/24* (2013.01); *C07K 2317/41* (2013.01); *C07K 2317/54* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 4,501,729 A | 2/1985 | Boucher et al. | |
| 6,045,786 A | 4/2000 | Cone et al. | |
| 6,355,235 B1 | 3/2002 | Cone et al. | |
| 8,106,169 B2* | 1/2012 | Briggs | C07K 16/2839 435/69.6 |
| 10,100,102 B2 | 10/2018 | Lai et al. | |
| 2006/0083741 A1 | 4/2006 | Hoffman et al. | |
| 2006/0131350 A1 | 6/2006 | Schechter et al. | |
| 2006/0198848 A1 | 9/2006 | Betz et al. | |
| 2008/0060092 A1 | 3/2008 | Dickey et al. | |
| 2010/0008905 A1 | 1/2010 | Burioni et al. | |
| 2010/0172906 A1* | 7/2010 | Lai | A61P 31/22 435/254.2 |
| 2011/0318376 A1 | 12/2011 | Murata et al. | |

FOREIGN PATENT DOCUMENTS

| | | |
|---|---|---|
| WO | 9201473 A1 | 2/1992 |
| WO | 2006012539 A1 | 2/2006 |
| WO | 2006135309 A2 | 12/2006 |
| WO | 2012078877 A2 | 6/2012 |
| WO | 2014070786 A1 | 5/2014 |

OTHER PUBLICATIONS

Epstein et al., Cornea, Jul. 2001, 20(5):495-500. (Year: 2001).*
European Search Report corresponding to European Application No. 13851374.2 dated May 4, 2016.
Extended European Search Report corresponding to European Application No. 19218983.5 dated May 27, 2020.
Ghirlando R, Lund J, Goodall M, Jefferis R. Glycosylation of human IgG-Fc: influences on structure revealed by differential scanning micro-calorimetry. Immunol Lett. May 3, 1999;68(1):47-52.
Hobbs SM, Jackson LE, Hoadley J. Interaction of aglycosyl immunoglobulins with the IgG Fc transport receptor from neonatal rat gut: comparison of deglycosylation by tunicamycin treatment and genetic engineering. Mol Immunol. Jul.-Aug. 1992;29(7-8):949-56.
Labrijn A. F. and Parren W. H. l., 1999, Neutralizing epitopes of HIV-1, p. 13-34, in B. Korber, C. Brander, B. F. Haynes, J. P. Moore, R. Koup, B. Walker, and D. I. Watkins (ed.), HIV Molecular Immunology database, Los Alamos National Laboratory, Los Alamos, New Mexico, also available from https://www.hiv.lanl.gov/content/sequence/HIV/REVIEWS/art.

(Continued)

*Primary Examiner* — Stacy B Chen
(74) *Attorney, Agent, or Firm* — Myers Bigel, P.A.

(57) ABSTRACT

The presently-disclosed subject matter relates to antibodies, compositions, and methods for inhibiting and treating virus infection in the respiratory tract and virus transmission through the respiratory tract. In particular, the presently-disclosed subject matter relates to inhibiting and treating virus infection in a subject using compositions and antibodies that trap viruses in mucus of the respiratory tract, thereby inhibiting transport of virus across or through mucus secretions.

23 Claims, 18 Drawing Sheets

Specification includes a Sequence Listing.

(56) References Cited

OTHER PUBLICATIONS

Lai SK, Wang YY, Hida K, Cone R, Hanes J. Nanoparticles reveal that human cervicovaginal mucus is riddled with pores larger than viruses. Proc Natl Acad Sci U S A. Jan. 12, 2010;107(2):598-603. doi: 10.1 073/pnas.0911748107. Epub Dec. 16, 2009. Erratum in: Pro.

Notification of Transmittal of the International Search Report and the Written Opinion of the International Searching Authority, or the Declaration corresponding to International Application No. PCT/US2013/067328 dated Mar. 13, 2014.

Notification of Transmittal of the International Search Report and the Written Opinion of the International Searching Authority, or the Declaration corresponding to International Application No. PCT/US2016/061574 dated Feb. 27, 2017.

Olmsted SS, Padgett JL, Yudin AI, Whaley KJ, Moench TR, Cone RA. Diffusion of macromolecules and virus-like particles in human cervical mucus. Biophys J. Oct. 2001;81 (4):1930-7.

Parr EL, Bozzola JJ, Parr MB. Immunity to vaginal infection by herpes simplex virus type 2 in adult mice: characterization of the immunoglobulins in vaginal mucus. J Rep rod Immunol. Apr. 1998;38(1):15-30.

Bomsel, et al., "Immunization with HIV-1 gp41 Subunit Virosomes Induces Mucosal Antibodies Protecting Nonhuman Primates against Vaginal SHIV Challenges", Immunity 34:269-280 (2011).

Carragher, et al. "The Journal of Immunology," 2008, 181:4186-4176.

Chen, et al., "Transient Antibody-Mucin Interactions Produce a Dynamic Molecular Shield against Viral Invasion", Biophysical Journal 108:2028-2036 (2014).

Cosio, et al., "Binding of human fibronectin to antigen-antibody complexes", The Journal of Laboratory and Clinical Medicine 107(5):453-458 (1986) Abstract Only (2 pages).

Desoubeaux, et al., "Therapeutic monoclonal antibodies for respiratory diseases: Current challenges and perspectives, Mar. 31-Apr. 1, 2016, Tours, France", MABS 8(6):999-1009 (2016).

Dudley, et al., "Immune Protection against HSV-2 in B-Cell-Deficient Mice", Virology 270:454-463 (2000).

Ercan, et al., "Multiple juvenile idiopathic arthritis subtypes demonstrate pro-inflammatory IgG glycosylation", Arthritis Rheum. 64(9):3025-3033 (2012).

Fahrbach, et al., "Differential Binding of IgG and IgA to Mucus of the Female Reproductive Tract", PLOS One 8(10):e76176 (2013) 11 pages.

Fellner, et al., "Inhaled protein/peptide-based therapies for respiratory disease", Molecular and Cellular Pediatrics 3:16 pp. 1-5 (2016).

Hansen, et al., "Antibodies in the small intestine: mucosal synthesis and deposition of anti-glycosyl IgA, IgM, and IgG in the enterocyte brush border", Am. J. Physiol. Gastrointest. Liver Physiol. 291:G82-G90 (2006).

Kannan, et al., "Mucosal immunity mediated by antibody-mucin cross-linking", Glycobiology, Oxford University Press 22(11):1537-1538 (2012).

Karsten, et al., "Anti-inflammatory activity of IgG1 mediated by Fc galactosylation and association of Fc?RIIB and dectin-1", Nature Medicine 18(9):1401-1409 (2012).

Li, et al., "Cell culture processes for monoclonal antibody production", MABS 2(5):466-479 (2010).

Mascola, et al., "Protection of macaques against vaginal transmission of a pathogenic HIV-1/SIV chimeric virus by passive infusion of neutralizing antibodies", Nature Medicine 6(2):207-210 (2000).

Maverakis, et al., "Glycans in the immune system and The Altered Glycan Theory of Autoimmunity: A critical review", Journal of Autoimmunity 57:1-13 (2015).

Nelson, et al., Nature Reviews, Drug Discovery, Oct. 2010, 9:767-774.

Prince, et al., "Treatment of Respiratory Syncytial Virus Bronchiolitis and Pneumonia in a Cotton Rat Model with Systemically Administered Monoclonal Antibody (Palivizumab) and Glucocorticosteroid", The Journal of Infectious Diseases 182:1326-30 (2000).

Raju, et al., "Species-specific variation in glycosylation of IgG: evidence for the species-specific sialylation and branch-specific galactosylation and importance for engineering recombinant glycoprotein therapeutics", Glycobiology 10(5):477-486 (2000).

Reusch, et al., "Comparison of methods for the analysis of therapeutic immunoglobulin G Fc-glycosylation profiles—Part 1: Separation-based methods", MABS 7(1):167-179 (2015).

Rimensberger, et al., "Aerosolized immunoglobulin treatment of respiratory syncytial virus infection in infants", The Pediatric Infectious Disease Journal 15(3):209-216 (1996) Abstract Only.

Saltzman, et al., "Long-Term Vaginal Antibody Delivery: Delivery Systems and Biodistribution", Biotechnol Bioeng 67:253-264 (2000).

Whaley, et al. "Emerging antibody products and Nicotiana manufacturing", Human Vaccines 7(3):349-356 (2011).

Xu, et al., "Passive immunization with human neutralizing monoclonal antibodies: correlates of protective immunity against HIV", Vaccine 20:1956-1960 (2002).

"European Search Report corresponding to European Application No. 19218983.5 dated Mar. 22, 2023".

* cited by examiner

FIGS. 2A-2B

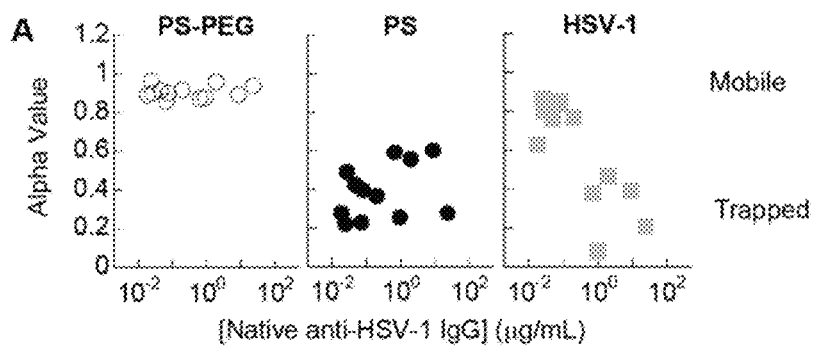

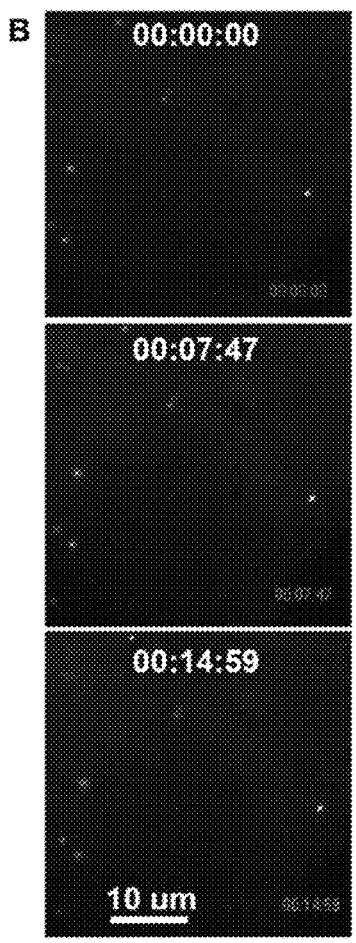

Average α values for PS-PEG, PS and HSV-1 in native or Ab-treated CVM

| Particle | Treatment | n | α |
|---|---|---|---|
| PS-PEG | Native (low endogenous anti-HSV-1 IgG) | 7 | 0.91 ± 0.012 |
| PS-PEG | Native (high endogenous anti-HSV-1 IgG) | 5 | 0.91 ± 0.016 |
| PS | Native (low endogenous anti-HSV-1 IgG) | 7 | 0.34 ± 0.039 |
| PS | Native (high endogenous anti-HSV-1 IgG) | 5 | 0.46 ± 0.078 |
| HSV-1 | Native (low endogenous anti-HSV-1 IgG) | 7 | 0.79 ± 0.031 |
| HSV-1 | Native (high endogenous anti-HSV-1 IgG) | 5 | 0.31 ± 0.071 * |
| HSV-1 | 33 ng/mL anti-HSV-1 IgG | 7 | 0.67 ± 0.029 * |
| HSV-1 | 100 ng/mL anti-HSV-1 IgG | 7 | 0.48 ± 0.074 * |
| HSV-1 | 333 ng/mL anti-HSV-1 IgG | 7 | 0.32 ± 0.046 * |
| HSV-1 | 1000 ng/mL anti-HSV-1 IgG | 7 | 0.31 ± 0.045 * |
| HSV-1 | Native (low endogenous anti-HSV-1 IgG) | 5 | 0.76 ± 0.059 |
| HSV-1 | Anti-HSV-1 IgG | 5 | 0.35 ± 0.054 * |
| HSV-1 | Deglycosylated anti-HSV-1 IgG | 4 | 0.62 ± 0.10 |
| HSV-1 | Anti-HSV-1 F(ab')₂ | 4 | 0.59 ± 0.063 |

†Values are expressed as mean ± SEM
* indicates $p < 0.01$ compared to "Native (low endogenous anti-HSV-1 IgG)" group; based on Student's t-test (paired for comparisons of Ab-treated vs. native CVM for the same CVM samples)

FIGS. 4A-4B
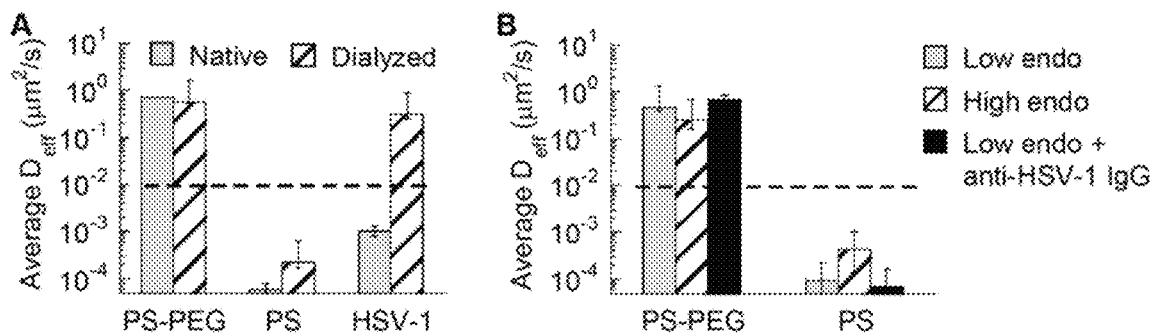
FIGS. 5A-5C
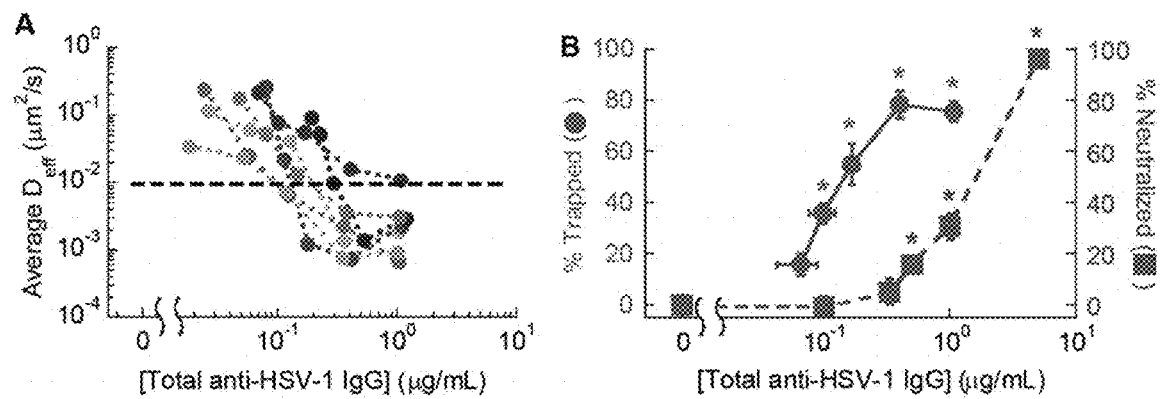
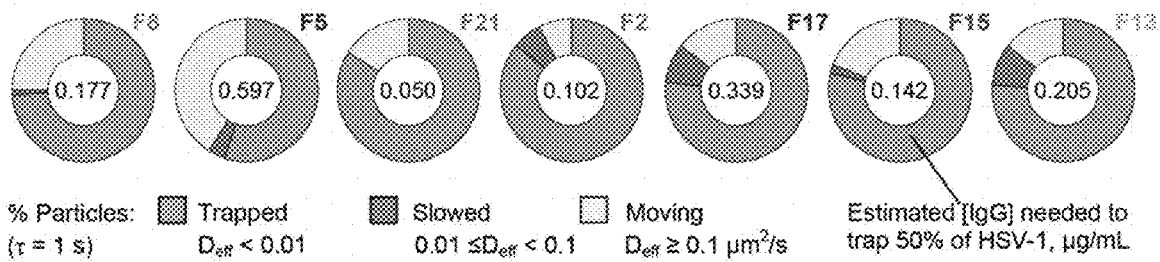

FIGS. 9A-9C
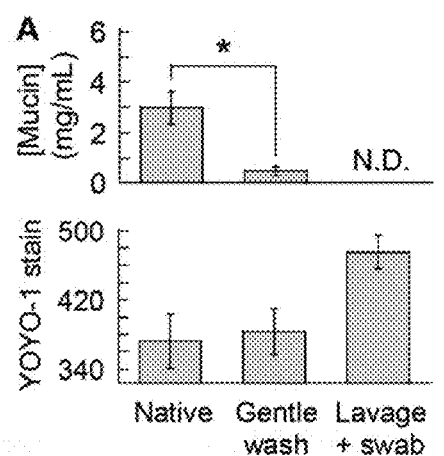
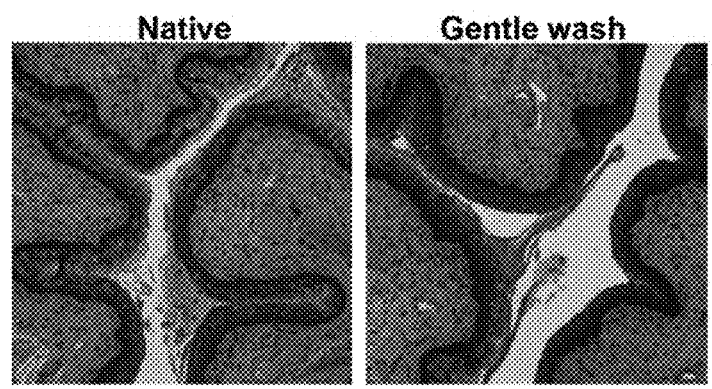
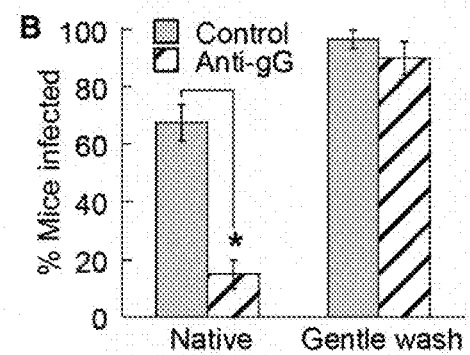
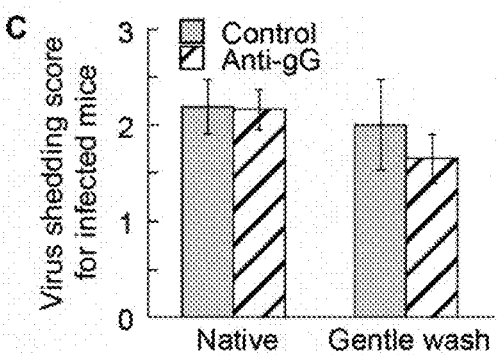

SEQUENCE LISTING

```
<160> NUMBER OF SEQ ID NOS: 13

<210> SEQ ID NO 1
<211> LENGTH: 126
<212> TYPE: PRT
<213> ORGANISM: Artificial
<220> FEATURE:
<223> OTHER INFORMATION: Heavy Chain Variable Region

<400> SEQUENCE: 1

Gln Val Gln Leu Val Gln Ser Gly Ala Glu Val Lys Lys Pro Gly Ser
1               5                   10                  15

Ser Val Met Val Ser Cys Gln Ala Ser Gly Pro Leu Arg Asn Tyr
                20                  25                  30

Ile Ile Asn Trp Leu Arg Gln Ala Pro Gly Gln Gly Pro Glu Trp Met
                35                  40                  45

Gly Gly Ile Ile Pro Val Leu Gly Thr Val His Tyr Ala Pro Lys Phe
        50                  55                  60

Gln Gly Arg Val Thr Ile Thr Ala Asp Glu Ser Thr Asp Thr Ala Tyr
65                  70                  75                  80

Ile His Leu Ile Ser Leu Arg Ser Glu Asp Thr Ala Met Tyr Tyr Cys
                85                  90                  95

Ala Thr Glu Thr Ala Leu Val Val Ser Thr Thr Tyr Leu Pro His Tyr
                100                 105                 110

Phe Asp Asn Trp Gly Gln Gly Thr Leu Val Thr Val Ser Ser
                115                 120                 125

<210> SEQ ID NO 2
<211> LENGTH: 110
<212> TYPE: PRT
<213> ORGANISM: Artificial
<220> FEATURE:
<223> OTHER INFORMATION: Light Chain Variable Region

<400> SEQUENCE: 2

Asp Ile Gln Met Thr Gln Ser Pro Ser Ser Leu Ser Ala Ala Val Gly
1               5                   10                  15

Asp Arg Val Thr Ile Thr Cys Gln Ala Ser Gln Asp Ile Val Asn Tyr
                20                  25                  30

Leu Asn Trp Tyr Gln Gln Lys Pro Gly Lys Ala Pro Lys Leu Leu Ile
                35                  40                  45

Tyr Val Ala Ser Asn Leu Glu Thr Gly Val Pro Ser Arg Phe Ser Gly
        50                  55                  60

Ser Gly Ser Gly Thr Asp Phe Ser Leu Thr Ile Ser Ser Leu Gln Pro
65                  70                  75                  80

Glu Asp Val Ala Thr Tyr Tyr Cys Gln Gln Tyr Asp Asn Leu Pro Leu
                85                  90                  95

Thr Phe Gly Gly Gly Thr Lys Val Glu Ile Lys Arg Thr Val
                100                 105                 110

<210> SEQ ID NO 3
<211> LENGTH: 120
<212> TYPE: PRT
<213> ORGANISM: Artificial
<220> FEATURE:
<223> OTHER INFORMATION: Heavy Chain Variable Region

<400> SEQUENCE: 3
```

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Met Ser Val Gly Trp Ile Arg Gln Pro Pro Gly Lys Ala Leu Glu
            35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Ala
            100                 105                 110

Gly Thr Thr Val Thr Val Ser Ser
        115                 120
```

<210> SEQ ID NO 4
<211> LENGTH: 120
<212> TYPE: PRT
<213> ORGANISM: Artificial
<220> FEATURE:
<223> OTHER INFORMATION: Heavy Chain Variable Region

<400> SEQUENCE: 4

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
                20                  25                  30

Gly Met Ser Val Gly Trp Ile Arg Gln Pro Pro Gly Lys Ala Leu Glu
            35                  40                  45

Trp Leu Ala Asp Ile Trp Trp Asp Asp Lys Lys His Tyr Asn Pro Ser
    50                  55                  60

Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Gln
            100                 105                 110

Gly Thr Thr Val Thr Val Ser Ser
        115                 120
```

<210> SEQ ID NO 5
<211> LENGTH: 120
<212> TYPE: PRT
<213> ORGANISM: Artificial
<220> FEATURE:
<223> OTHER INFORMATION: Heavy Chain Variable Region

<400> SEQUENCE: 5

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
                20                  25                  30

Gly Met Ser Val Gly Trp Ile Arg Gln Pro Pro Gly Lys Ala Leu Glu
            35                  40                  45

Trp Leu Ala Asp Ile Trp Trp Asp Asp Lys Lys His Tyr Asn Pro Ser
```

```
                  50                  55                  60

Leu Lys Asp Arg Leu Thr Ile Ser Lys Asp Thr Ser Lys Asn Gln Val
 65                  70                  75                  80

Val Leu Lys Val Thr Asn Met Asp Pro Ala Asp Thr Ala Thr Tyr Tyr
                     85                  90                  95

Cys Ala Arg Ser Met Ile Thr Asn Phe Tyr Phe Asp Val Trp Gly Gln
                    100                 105                 110

Gly Thr Thr Val Thr Val Ser Ser
            115                 120

<210> SEQ ID NO 6
<211> LENGTH: 120
<212> TYPE: PRT
<213> ORGANISM: Artificial
<220> FEATURE:
<223> OTHER INFORMATION: Heavy Chain Variable Region

<400> SEQUENCE: 6

Gln Val Thr Leu Arg Glu Ser Gly Pro Ala Leu Val Lys Pro Thr Gln
  1               5                  10                  15

Thr Leu Thr Leu Thr Cys Thr Phe Ser Gly Phe Ser Leu Ser Thr Ala
                 20                  25                  30

Gly Met Ser Val Gly Trp Ile Arg Gln Pro Pro Gly Lys Ala Leu Glu
            35                  40                  45

Trp Leu Ala Asp Ile Trp Trp Asp Asp Lys Lys Asp Tyr Asn Pro Ser
 50                  55                  60

Leu Lys Ser Arg Leu Thr Ile Ser Lys Asp Thr Ser Lys Asn Gln Val
 65                  70                  75                  80

Val Leu Lys Val Thr Asn Met Asp Pro Ala Asp Thr Ala Thr Tyr Tyr
                     85                  90                  95

Cys Ala Arg Asp Met Ile Phe Asn Phe Tyr Phe Asp Val Trp Gly Gln
                    100                 105                 110

Gly Thr Thr Val Thr Val Ser Ser
            115                 120

<210> SEQ ID NO 7
<211> LENGTH: 120
<212> TYPE: PRT
<213> ORGANISM: Artificial
<220> FEATURE:
<223> OTHER INFORMATION: Heavy Chain Variable Region

<400> SEQUENCE: 7

Gln Val Thr Leu Arg Glu Ser Gly Pro Ala Leu Val Lys Pro Thr Gln
  1               5                  10                  15

Thr Leu Thr Leu Thr Cys Thr Phe Ser Gly Phe Ser Leu Ser Thr Ser
                 20                  25                  30

Gly Met Ser Val Gly Trp Ile Arg Gln Pro Pro Gly Lys Ala Leu Glu
            35                  40                  45

Trp Leu Ala Asp Ile Trp Trp Asp Asp Lys Lys Asp Tyr Asn Pro Ser
 50                  55                  60

Leu Lys Ser Arg Leu Thr Ile Ser Lys Asp Thr Ser Lys Asn Gln Val
 65                  70                  75                  80

Val Leu Lys Val Thr Asn Met Asp Pro Ala Asp Thr Ala Thr Tyr Tyr
                     85                  90                  95

Cys Ala Arg Asp Met Ile Phe Asn Phe Tyr Phe Asp Val Trp Gly Gln
                    100                 105                 110
```

```
Gly Thr Thr Val Thr Val Ser Ser
        115                 120
```

```
<210> SEQ ID NO 8
<211> LENGTH: 106
<212> TYPE: PRT
<213> ORGANISM: Artificial
<220> FEATURE:
<223> OTHER INFORMATION: Light Chain Variable Region

<400> SEQUENCE: 8

Asp Ile Gln Met Thr Gln Ser Pro Ser Thr Leu Ser Ala Ser Val Gly
1               5                   10                  15

Asp Arg Val Thr Ile Thr Cys Lys Cys Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
            100                 105
```

```
<210> SEQ ID NO 9
<211> LENGTH: 106
<212> TYPE: PRT
<213> ORGANISM: Artificial
<220> FEATURE:
<223> OTHER INFORMATION: Light Chain Variable Region

<400> SEQUENCE: 9

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Ser Val Gly Tyr Met
            20                  25                  30

His Trp Tyr Gln Gln Lys Pro Gly Lys Ala Pro Lys Leu Leu Ile Tyr
        35                  40                  45

Asp Thr Phe Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Phe Tyr Pro Phe Thr
                85                  90                  95

Phe Gly Gly Gly Thr Lys Val Glu Ile Lys
            100                 105
```

```
<210> SEQ ID NO 10
<211> LENGTH: 106
<212> TYPE: PRT
<213> ORGANISM: Artificial
<220> FEATURE:
<223> OTHER INFORMATION: Light Chain Variable Region

<400> SEQUENCE: 10

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Ser Val Gly Tyr Met
```

```
                    20                  25                  30

His Trp Tyr Gln Gln Lys Pro Gly Lys Ala Pro Lys Leu Leu Ile Tyr
            35                  40                  45

Asp Thr Phe Phe Leu Asp Ser Gly Val Pro Ser Arg Phe Ser Gly Ser
        50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys
            100                 105

<210> SEQ ID NO 11
<211> LENGTH: 106
<212> TYPE: PRT
<213> ORGANISM: Artificial
<220> FEATURE:
<223> OTHER INFORMATION: Light Chain Variable Region

<400> SEQUENCE: 11

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Arg Val Gly Tyr Met
            20                  25                  30

His Trp Tyr Gln Gln Lys Pro Gly Lys Ala Pro Lys Leu Leu Ile Tyr
            35                  40                  45

Asp Thr Ser Lys Leu Ala Ser Gly Val Pro Ser Arg Phe Ser Gly Ser
        50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys
            100                 105

<210> SEQ ID NO 12
<211> LENGTH: 106
<212> TYPE: PRT
<213> ORGANISM: Artificial
<220> FEATURE:
<223> OTHER INFORMATION: Light Chain Variable Region

<400> SEQUENCE: 12

Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Arg Val Gly Tyr Met
            20                  25                  30

His Trp Tyr Gln Gln Lys Pro Gly Lys Ala Pro Lys Leu Leu Ile Tyr
            35                  40                  45

Asp Thr Ser Lys Leu Ala Ser Gly Val Pro Ser Arg Phe Ser Gly Ser
        50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys
            100                 105
```

```
<210> SEQ ID NO 13
<211> LENGTH: 5
<212> TYPE: PRT
<213> ORGANISM: Artificial
<220> FEATURE:
<223> OTHER INFORMATION: Linker

<400> SEQUENCE: 13

Gly Ser Ser Ser Ser
1               5
```

COMPOSITIONS AND METHODS FOR INHIBITING PATHOGEN INFECTION

CROSS REFERENCE TO RELATED APPLICATIONS

This patent application is a continuation of U.S. patent application Ser. No. 16/138,643, filed Sep. 21, 2018, which is a continuation-in-part of U.S. patent application Ser. No. 14/438,511, filed Apr. 24, 2015, claiming priority under 35 U.S. § 371 to PCT/US2013/067328, filed Oct. 29, 2013, titled "Compositions and Methods for Inhibiting Pathogen Infection", claiming priority to U.S. provisional patent application No. 61/719,689, filed on Oct. 29, 2012. This patent application also claims priority to U.S. provisional patent application No. 62/646,220, filed Mar. 21, 2018, titled "Compositions and Methods for Inhibiting Pathogen Infection in the Lung". Each of these patent applications is herein incorporated by reference in its entirety.

STATEMENT AS TO FEDERALLY SPONSORED RESEARCH

This invention was made with government support under Grant Nos. R21AI093242, U19AI096398 and UL1TR001111, awarded by the National Institutes of Health. The government has certain rights in the invention.

INCORPORATION BY REFERENCE

All publications and patent applications mentioned in this specification are herein incorporated by reference in their entirety to the same extent as if each individual publication or patent application was specifically and individually indicated to be incorporated by reference.

STATEMENT REGARDING ELECTRONIC FILING OF A SEQUENCE LISTING

A Sequence Listing in ASCII text format, submitted under 37 C.F.R. § 1.821, entitled 5470-682TSIPCT_ST25.txt, 13,823 bytes in size, generated on Oct. 7, 2020 and filed via EFS-Web, is provided in lieu of a paper copy. This Sequence Listing is hereby incorporated by reference into the specification for its disclosures.

FIELD OF THE INVENTION

The presently-disclosed subject matter relates to antibodies, compositions, and methods for inhibiting and treating pathogen infection and providing contraception. In particular, the presently-disclosed subject matter relates to inhibiting and treating pathogen infection and providing contraception in a subject using compositions and antibodies that trap pathogens in mucus, thereby inhibiting transport of pathogens or sperm across or through mucus secretions. The subject matter further relates to methods for monitoring the effectiveness of vaccines by detecting antibodies capable of trapping pathogens in mucus. For example, the presently-disclosed subject matter relates to antibodies, compositions, and methods for inhibiting and treating virus infection in the respiratory tract and virus transmission through the respiratory tract, including using compositions and antibodies that trap viruses in mucus of the respiratory tract, thereby inhibiting transport of virus across or through mucus secretions.

BACKGROUND OF THE INVENTION

Large quantities of IgG are transported into female genital tract mucus secretions by the MHC class I-related neonatal Fc receptor (Li et al., *Proc. Natl. Acad. Sci. U.S.A.* 108:4388 (2011), resulting in at least ten-fold more IgG than IgA (Usala et al., *J. Reprod. Med.* 34:292 (1989)). However, despite this predominance of IgG, the precise mechanism(s) by which secreted IgG can prevent vaginal infections are not well understood. Previous animal studies have shown that antibodies (Ab) can provide robust protection against vaginal challenge with pathogens, including human immunodeficiency virus (HIV) and herpes simplex virus-2 (HSV-2), when applied intravaginally (Burton et al., *Proc. Natl. Acad. Sci. U.S.A.* 108:11181 (2011); Sherwood et al., *Nature Biotechnol.* 14:468 (1996); Veazey et al., *Nature Med.* 9:343 (2003); Whaley et al., *J. Infect. Dis,* 169:647 (1994)) or even intravenously (Hessell et al., *PLoSPathogens* 5:e1000433 (2009); Mascola et al., *Nature Med.* 6:207 (2000)). Many investigators have focused on neutralizing Ab, which, at sufficiently high doses, provided sterilizing immunity against simian-human immunodeficiency virus (SHIV) challenge in rhesus macaques (Burton et al., *Proc. Natl. Acad. Sci. U.S.A.* 108:11181 (2011)). In the same studies, non-neutralizing or poorly neutralizing Ab provided at best only partial protection, with some infected animals exhibiting reduced viral load. Studies by Hessell et al. and Mascola et al. showed complete protection in some animals even by weakly neutralizing antibodies, as well as reduced viremia in others (Hessell et al., *PLoS Pathogens* 5:e1000433 (2009); Mascola et al., *Nature Med.* 6:207 (2000)).

Few studies have explored the potential protective role of IgG within the mucus secretions overlaying the epithelial tissue, which sexually transmitted viruses invariably encounter and must penetrate in order to reach target cells. Well-known Ab effector functions in blood and lymph (e.g., complement activation, opsonization, and ADCC) are absent or limited in healthy female genital secretions, which typically have little complement activity and few if any active leukocytes (Cone, In *Handbook of Mucosal Immunology*. P. L. Ogra et al., editors. Academic Press, San Diego, Calif. 43-64 (1999); Hill et al., *Am. J. Obstet. Gynecol.* 166:720 (1992); Schumacher, *Hum. Reprod.* 3:289 (1988)). These classical mechanisms of systemic immune protection do not adequately account for the moderate but significant protection observed in the landmark Thai RV144 HIV vaccine trial (Kresge, *IAVI Report* Vol 13, Number 5 (2009); Rerks-Ngarm et al., *N. Engl. J. Med.* 361:2209 (2009)). The vaccination regimen modestly reduced the risk of HIV acquisition despite inducing primarily non-neutralizing Ab and otherwise offering little to no protection against systemic progression of infections once acquired, suggesting that protection likely occurred prior to initiation of infection. A better understanding of potential additional mechanisms of vaginal mucosal immunity will also likely be critical for developing effective vaccines against other sexually transmitted infections, including HSV, which has been shown to evade complement and other classical antibody-mediated protective mechanisms (Brockman et al., Vaccine 26 Suppl 8:194 (2008); Hook et al., *J. Virol.* 80:4038 (2006); Lubinski et al., *J. Exp. Med.* 190:1637 (1999)). To date, herpes vaccine candidates have achieved only transient and partial protection despite inducing high neutralizing serum antibody titers and cellular immunity (Chentoufi et al., *Clin. Dev. Immunol.* 2012:187585 (2012)). A Phase III clinical trial, using a subunit vaccine based on HSV-2 glycoprotein D, demonstrated some protection against HSV-1 infection but no efficacy against HSV-2 infection and no overall efficacy against genital disease (Belshe et al., *New Eng. J Med.* 366:34 (2012)).

There is a need in the art for new compositions, and methods of using such compositions, to prevent and treat infectious diseases and provide contraception.

For example, respiratory infections, such as influenza virus and respiratory syncytial virus (RSV) infections, are a tremendous health and financial burden. Additionally, the mucosal lining of the respiratory tract is a point of entry for non-respiratory viruses such as Ebola virus. Ideally, viral infection in or through the lungs would be prevented by transporting virions that enter the respiratory tract out of the tract before they have a chance to contact cells.

Thus, there is a need for new compositions, and methods of using such compositions, to prevent and treat viral infectious diseases, including in particular diseases in the respiratory tract.

SUMMARY OF THE INVENTION

Viruses must penetrate cervicovaginal mucus (CVM) to reach and infect their target cells in the vaginal epithelium; indeed, HIV and human papillomavirus (HPV) are both capable of rapidly diffusing through human genital mucus secretions (Lai et al., *J. Virol.* 83:11196 (2009); Olmsted et al., *Biophys. J.* 81:1930 (2001)). It was previously found that the diffusion of IgG (11 nm) was slowed slightly in human cervical mucus compared to saline buffer, while much larger virus-like particles, including the capsids of norovirus (38 nm) and HPV (55 nm), were not slowed by this mucus (Olmsted et al., *Biophys. J.* 81:1930 (2001)). It was hypothesized that the slight retardation of the much smaller IgG molecules may be due to very transient (<1 s), low-affinity bonds with the mucin mesh (Olmsted et al., *Biophys. J.* 81:1930 (2001)). In other words, by making only transient low-affinity bonds with mucins, IgG is able to diffuse rapidly through mucus, and in theory is therefore free to quickly accumulate on a pathogen surface.

Surprisingly, as described herein, Ab bound to a pathogen surface can effectively trap the pathogen in mucus gel by ensuring at least some low-affinity bonds to the mucin mesh are present at any given time (illustrated in FIG. 13). Virions trapped in CVM cannot reach their target cells, and will instead be shed with post-coital discharge and/or inactivated by spontaneous thermal degradation as well as additional protective factors in mucus, such as defensins (Cole, *Curr. Top. Microbiol. Immunol.* 306:199 (2006); Doss et al., *J. Leukoc. Biol.* 87:79 (2010). This discovery provides novel methods for preventing and treating infection, monitoring the effectiveness of vaccines, and/or providing contraception.

Thus, one aspect of the methods and compositions described herein may relate to an isolated antibody comprising an oligosaccharide at a glycosylation site, the oligosaccharide comprising a glycosylation pattern that enhances trapping potency of the antibody in mucus, wherein the antibody specifically binds an epitope of a target pathogen or sperm. In general, these methods and compositions may include trapping antibodies directed against a target virion in mucus (e.g., within the lungs, vagina, etc.).

A further aspect may relate to compositions, e.g., pharmaceutical compositions, and kits comprising the antibodies of the invention.

An additional aspect of the invention relates to a method of inhibiting an infection by a pathogen or a disease or disorder caused by an infection by a pathogen in a subject in need thereof, comprising administering to a mucosa of the subject an antibody (e.g., an antibody that is adapted to have an enhanced trapping potency in mucus) in an amount effective to inhibit an infection.

Another aspect of the invention relates to a method of treating an infection by a pathogen or a disease or disorder caused by an infection by a pathogen in a subject in need thereof, comprising administering to a mucosa of the subject the antibody of the invention in an amount effective to treat the infection.

A further aspect of the invention relates to a method of providing contraception in a female subject, comprising administering to a mucosa of a reproductive tract of the subject the antibody of the invention in an amount effective to provide contraception, wherein the antibody specifically binds an epitope of sperm.

An additional aspect of the invention relates to a method of monitoring the effectiveness of a vaccination in a subject that has been vaccinated against a target pathogen, comprising determining in a mucus sample from said subject the amount of an antibody comprising an oligosaccharide at a glycosylation site, the oligosaccharide having a glycosylation pattern that enhances trapping potency of the antibody in mucus, wherein the antibody specifically binds an epitope of said target pathogen.

Typically, viruses must penetrate the mucus of the respiratory tract to reach and infect their target cells in the epithelium. The present invention is based in part on the finding that antibodies in the respiratory tract can bind to virions and effectively trap the virions in mucus gel by ensuring at least some low-affinity bonds to the mucin mesh are present at any given time. Virions trapped in the mucus cannot reach their target cells, and will instead be shed from the respiratory tract with the mucus. This provides novel methods for preventing and treating infection in the respiratory tract.

Thus, one aspect of the invention relates to method for treating or preventing a viral infection in a subject in need thereof, the viral infection characterized by a virion in the lung of the subject, the method comprising administering, via an inhaled route, an antibody, e.g., a recombinant monoclonal antibody molecule, comprising a human Fc portion and a set of CDRs with specific affinity for the virion, thereby treating or preventing the infection. The antibody may be delivered in an aerosol composition, e.g., by nebulizer.

A further aspect of the invention relates to compositions comprising an antibody, e.g., a recombinant monoclonal antibody molecule, comprising a human Fc portion and a set of CDRs with specific affinity for a virion present in the lung of a subject, wherein the composition is suitable for inhalation.

An additional aspect of the invention relates to a kit comprising the compositions of the invention.

For example, described herein are methods for treating or preventing an infection by a pathogen (e.g., treating and/or preventing a viral infection by a virion, treating and/or preventing a bacterial infection, treating and/or preventing a fungal infection) in a subject in need thereof. For example, a method for treating and/or preventing a viral infection by a virion in a subject in need thereof may include: administering to the subject, via an inhaled route, a recombinant antibody with a specific affinity for the virion, the recombinant antibody comprising a human or humanized Fc region, wherein the recombinant antibody comprises an oligosaccharide having a glycosylation pattern that enhances the trapping potency of the recombinant antibody in mucus, so that the recombinant antibody binds to the virion to form an antibody/virion complex that is trapped in the subject's mucus thereby treating or preventing the infection.

The administration of the mAb may refer to administering a population of mAbs that has been enriched for mAbs having a glycosylation pattern that enhances mucosal trapping.

The recombinant antibody may, when not bound to target (e.g., virion) be weakly interacting with mucus and may therefore freely diffuse through the mucus; however, once bound to the target (e.g., virion) to form an antibody/virion complex, it may trap the antibody/virion complex within the mucus, allowing it to be removed and/or destroyed by the body. The concentration of antibody in the mucus (and particularly the concentration of mAb having an enhanced trapping efficiency, such as having a G0/G0F (i.e. GnGn) glycosylation pattern) may be, e.g., 50 ng/mL or greater, (e.g., 100 ng/mL or greater, 200 ng/mL or greater, 500 ng/mL or greater, 1 µg/mL or greater, 10 µg/mL or greater, 12.5 µg/mL or greater, 15.0 µg/mL or greater, 20 µg/mL or greater, etc., e.g., between 0.1 µg/mL and 20 µg/mL).

In general, recombinant antibodies having an increased mucosal trapping potency may comprise an N-linked glycosylation site on the Fc region of the antibodies to which the oligosaccharide is attached. For example, the glycosylation pattern may comprise a biantennary core glycan structure of Manα1-6(Manα1-3)Manβ1-4GlcNAcβ1-4GlcNAcβ1 with terminal N-acetylglucosamine on each branch. In some variations at least 20% (e.g., at least 25%, at least 30%, at least 35%, at least 40%, at least 45%, at least 50%, at least 55%, at least 60%, at least 65%, at least 70%, at least 75%, at least 80%, etc., and particularly 50% or more, e.g., 55% or greater, 60% or greater, 65% or greater, between 80-100%, etc.) of the recombinant antibodies in the population administered to the patient have a glycosylation pattern comprising the biantennary core glycan structure Manα1-6(Manα1-3)Manβ1-4GlcNAcβ1-4GlcNAcβ1 with terminal N-acetylglucosamine on each branch. For example, at least 50% of the recombinant antibodies in the population have a glycosylation pattern comprising the biantennary core glycan structure Manα1-6(Manα1-3)Manβ1-4GlcNAcβ1-4GlcNAcβ1 with terminal N-acetylglucosamine on each branch.

As mentioned, any of these methods may include forming an antibody/virion complex and trapping an antibody/virion complex in the mucus. The recombinant antibody may be configured to bind to a non-neutralizing epitope of the virion. Administering may comprise administering a dose at a sub-neutralization dose level.

Any of these methods may include reducing the mobility of the virion in the patient's mucus to no more than about 50% relative to its mobility in water. For example, any of these methods may include reducing the percentage of virion that can penetrate the patient's mucus by at least 10% (e.g., at least 15%, at least 20%, at least 25%, etc.).

The recombinant antibody may be a human or humanized IgG or IgM monoclonal antibody, or a fragment or derivative thereof.

The recombinant antibody may be formulated as an aerosol composition. For example, the recombinant antibody may be formulated to have a neutral pH (e.g., approximately neutral pH); in some variations the recombinant antibody may be formulated as a hypotonic solution.

Administering may comprise administering a nebulized composition of recombinant antibody having a Mass Median Aerodynamic Diameter (MMAD) in the 2-5 µm range, as measured using a Next Generation Impactor.

Appropriate dosing regimens may include dosing the subject with the recombinant antibody molecule via the inhaled route once every 3 to 24 hours. The dosing regimen may include dosing between about 5-100 mg/day (e.g., between about 15-50 mg/day, between about 5-200 mg/day, between about 15-200 mg/day, between about 5-150 mg/day, between about 15-150 mg/day, between about 5-100 mg/day, between about 15-100 mg/day, etc.). In some variations the dosing may be configured to maintain a sustained concentration in the mucus (e.g., for approximately at least 1 hour, 2 hours, 3 hours, 4 hours, 5 hours, 6 hours, 8 hours, 12 hours, 16 hours, 20 hours, 24 hours, etc.) of between about 0.5-1000 µg/mL in the mucus (e.g., 1 µg/mL or greater, 10 µg/mL or greater, 15 µg/mL or greater, 20 µg/mL or greater, 30 µg/mL or greater, 40 µg/mL or greater, 50 µg/mL or greater, 60 µg/mL or greater, 70 µg/mL or greater, 80 µg/mL or greater, 19 µg/mL or greater, 100 µg/mL or greater, 120 µg/mL or greater, 150 µg/mL or greater, etc.). This dosing may be used for adult patients and/or infant patients. Alternatively, for children (including infants), the dosing may be different.

For example, in some variations dosing may be per body weight. For example, for children, the dosing may be in the range of between 0.1-25 mg/kg range per day (e.g., 0.5-20 mg/kg per day, 1-15 mg/kg per day, etc.), e.g., 5-75 mg/day for a 5 kg infant. For adults, higher dose levels may be used, e.g., >500 mg/day to even 1 g/day. The concentration in mucus may be between 0.05-1000 µg/mL (e.g., between about 0.5-1000 µg/mL), etc.

As described herein, antibodies of the presently-disclosed subject matter (having an enhanced trapping potency in mucus) are capable of diffusing through mucus when they are unbound, to allow the antibody to bind a target pathogen or sperm at a desirable rate. However, when antibodies are bound to the target (e.g., virion), the cumulative effect of the antibody-mucin interactions effectively traps the pathogen or sperm in the mucus. Because in the unbound state the antibodies may diffuse quickly through the mucus, the half-life of a typical dose is likely to be between 12-24 hours, allowing once or twice daily dosing and still remain above a certain minimal threshold despite the natural renewal and clearance of mucus. The unbound antibodies that are topically delivered (e.g., by inhalation) are not likely to be cleared quickly from the lungs, and the antibody may be at a steady state with the fluid environment even though the mucin mesh is being cleared quickly.

The patient may be an infant (e.g., a human infant), a child, an adult, or an elderly adult (e.g., 55 or older, 60 or older, 65 or older, 70 or older, 75 or older, etc.) In some variations the patient is immunocompromised (e.g., due to a pre-existing condition, due to chemotherapy, due to bone marrow transplant, etc.)

In some embodiments, the virion may be selected from respiratory viruses and/or viruses that are not typically considered respiratory viruses, including but not limited to: Ebola virus, respiratory syncytial virus, influenza virus, adenovirus, human rhinovirus, coronavirus, norovirus, human metapneumovirus, parainfluenza virus, Hantavirus, MERS, Bocavirus, Marburg virus, enterovirus, etc. In particular, the virion may be respiratory syncytial virus.

For example, described herein are methods of immobilizing a respiratory virion in mucus of a subject's lung, the method comprising administering to the subject, via an inhaled route, a recombinant antibody with a specific affinity for the virion so that the recombinant antibody is trapped in the subject's mucus, the recombinant antibody comprising a human or humanized Fc region, wherein the recombinant antibody comprises an oligosaccharide having a glycosylation pattern that enhances the trapping potency of the recombinant antibody in mucus, wherein the recombinant antibody is trapped in the subject's mucus at a concentration of 50 ng/mL or greater (e.g., between 0.1 µg/mL and 20 µg/mL).

Also described herein are methods for blocking, preventing or eliminating the proliferation, infiltration or spreading of a respiratory virion in mucus of a subject's lung, the method comprising immobilizing the virion by administering to the subject, via an inhaled route, a recombinant antibody with a specific affinity for the virion so that the recombinant antibody is trapped in the subject's mucus, the recombinant antibody comprising a human or humanized Fc region, wherein the recombinant antibody comprises an oligosaccharide having a glycosylation pattern that enhances the trapping potency of the recombinant antibody in mucus.

These and other aspects of the invention are set forth in more detail in the description of the invention below.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 2A-2B show transport characteristics for control beads and HSV-1 in CVM. (A) Alpha (α) values for control beads (PS-PEG and PS) and HSV-1 in individual CVM samples from unique donors (n=12, each experiment performed independently) as a function of endogenous anti-HSV-1 IgG. α is the slope of the log-log mean square displacement (<MSD>) vs. time scale plot (α=1 for pure unobstructed Brownian diffusion, e.g., particles in water, and a becomes smaller as obstruction to particle diffusion increases). Alpha values from all tracking analyses are listed in the table. (B) HSV-1 virions trapped in CVM at short time scales remain similarly immobilized even at long time scales. HSV-1 in CVM sample with elevated endogenous anti-HSV-1 IgG remain confined to the same locations over more than 15 min. Time stamps (bottom right corner, magnified at top center; hh:mm:ss) indicate elapsed time in three images from a representative movie.

FIGS. 4A-4B show mobility of HSV-1, but not PS-PEG or PS, is influenced by anti-HSV-1 IgG levels in CVM. (A) HSV-1 is immobilized in native CVM samples with elevated endogenous anti-HSV-1 IgG, but becomes readily mobile in the same CVM specimens dialyzed to remove ~90-95% total IgG at constant sample volume. Control PS-PEG and PS particles remain diffusive and immobilized, respectively. Dashed line represents the $D_{eff}$ cutoff below which particles are permanently trapped (moving less than their diameter within 1 s). (B) The addition of exogenous anti-HSV-1 IgG to CVM samples with low levels of endogenous anti-HSV-1 IgG does not alter CVM's diffusional barrier properties to nanoparticles. Control PS-PEG and PS particles remained similarly diffusive and immobilized, respectively, in CVM with low endogenous ("Low endo"), high endogenous ("High endo") and exogenously added anti-HSV-1 IgG ("Low endo anti-HSV-1 IgG"). Differences in average $D_{eff}$ were not statistically significant for either PS-PEG or PS particles across the three conditions. Dashed line represents the $D_{eff}$ cutoff below which particles are permanently trapped (moving less than their diameter within 1 s).

FIGS. 5A-5C show anti-HSV-1 polyclonal human IgG added to CVM samples with low endogenous anti-HSV-1 IgG potently traps HSV-1. HSV-1 mobility was quantified in aliquots of the same CVM samples with different amounts of anti-HSV-1 IgG added. (A) Comparison of effective diffusivity ($D_{eff}$; $\tau=1$ s) for HSV-1 in CVM samples (n=7, each experiment performed independently) with different amounts of total anti-HSV-1 IgG (sum of endogenous and added IgG). Different colored circles represent distinct samples. (B) In vitro neutralization vs. trapping potency of anti-HSV-1 IgG. Neutralization was assayed based on reduction of HSV plaque formation in Vero cells; trapping was defined as $D_{eff}(\tau=1\text{ s})$ below 0.01 µm²/s. Total IgG was averaged across samples for each treatment group. Error bars represent SEM. * indicates statistically significant difference compared to respective controls (p<0.05). (C) Distribution of particle speeds in samples treated with 1 µg/mL IgG (annulus chart), and estimated concentration of total IgG (g/mL) needed for 50% trapping (number in center). Donor ID is indicated for each sample, with colors matching those in (A).

FIGS. 9A-9C show protection by anti-gG IgG$_1$ is lost when mouse CVM is removed by gentle vaginal wash. (A) Mucin concentration in vaginal fluid collected from the native or gently washed mouse vagina, YOYO-1 staining for vaginal epithelial cell damage in gently washed or conventionally lavaged and swabbed (cotton tip) mice, and H&E stained transverse sections of native vs. gently washed mouse vaginal tissue, N.D.=no data. (B) % infected among mice treated with 33 µg/mL anti-gG IgG with or without gentle washing to remove vaginal mucus. (C) The gentle wash did not alter the extent of infection in infected mice. Data represent at least three independent experiments, each with n=10 mice per group (total n=30-40 per group). Error bars represent SEM, * indicates statistically significant difference compared to control (p<0.05).

FIGS. 10A-10B show mobility of individual Salmonella typhimurium bacteria in control or anti-LPS monoclonal IgG-treated mouse gastrointestinal mucus. (A) Microscopy setup that enables measurement of bacterial mobility in real time directly in mucus overlaying intestinal epithelial tissue excised from mice. The epithelium was NOT subjected to washing and hence the physiological mucus layer is intact. (B) The fraction of motile Salmonella typhimurium and their velocities in mucus overlaying different parts of the GI tract in native vs. anti-LPS IgG1 treatment. Similar findings were observed with anti-flagella Ab as well as with IgG2a.

FIGS. 14A-14B show characterization of Ebola virus-like particles (VLP). (A) Incorporation of Ebola glycoprotein (GP) confirmed via Western blot. Ebola VLP were prepared by transfecting 293T cells with expression plasmids encoding Ebola GP and HIV Gag-mCherry. Null VLP were prepared from cells transfected with HIV Gag-mCherry only. rGPdTM (recombinant Ebola GP) serves as a positive control for the 110 kd GP band. (B) Ebola VLP immunoprecipitated with ZMapp™ or individual Ebola-binding IgG (c2G4, c116C6FR1 and c4G7). The Ebola-binding mAbs were modified to have a glycosylation pattern having a higher than usual G0 glycosylation pattern, as described herein, to enhance mucosal binding. The G0 content of the antibodies used herein was 80% or more (e.g., between 85-95%). rGPdTM serves as a positive control for the GP band, while Null VLP and α-Biotin serve as negative controls confirming the specificity of ZMapp™ binding to Ebola VLP.

In FIGS. 20A-20B, the RespiraClear is a muco-trapping form of palivizumab, as described herein. For example, RespiraClear in this example is a mAb having the heavy and light chain variable regions of palivizumab and a glycosylation pattern having a biantennary core glycan structure of Manα1-6(Manα1-3)Manβ1-4GlcNAcβ1-4GlcNAcβ1 with terminal N-acetylglucosamine on each branch. Cells are stained with DAPI. The virus is retained in the airways treated with PBS (left columns) but is cleared from the airways in mouse treated with 1 µg/mL RespiraClear (right columns). Both virus and treatments are dosed at 25 µL using an aerosolizer (e.g., a PennCentury microsprayer), and mouse is sacrificed 30 mins after treatment. (B) Quantitative analysis of images from histology studies. Studies were performed on n=6 mice with at least 10 sections analyzed per mice.

DETAILED DESCRIPTION OF THE INVENTION

Figures 1A, 1B:
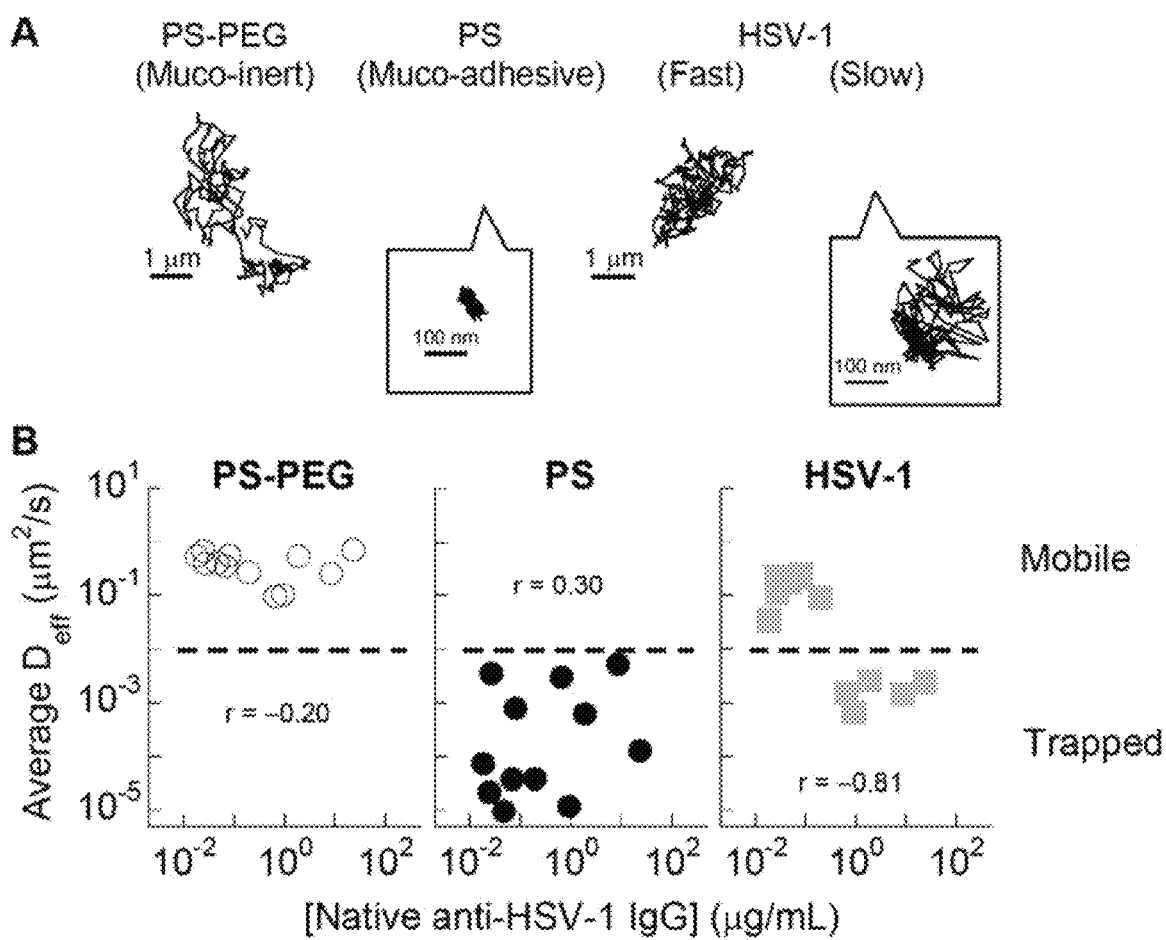
FIGS. 1A-1B show HSV-1 is immobilized in CVM samples with elevated endogenous anti-HSV-1 IgG but readily mobile in samples with low endogenous anti-HSV-1 IgG. Fluorescent HSV-1 or control particles were added to CVM, and their motions were analyzed by multiple particle tracking methods. (A) Representative 20 s traces of HSV-1 (d~180 nm) and control particles (d~200 nm) with effective diffusivity ($D_{eff}$) at a time scale r of 1 s within one SEM of the mean. Control particles include muco-inert (PEG-coated; PS-PEG) and muco-adhesive (uncoated; PS) polystyrene beads, which are freely diffusive and trapped in human CVM, respectively. (B) Geometric average $D_{eff}(\tau=1\text{ s})$ for PS-PEG, PS and HSV-1 in individual CVM samples from unique donors (n=12, each experiment performed independently) as a function of endogenous anti-HSV-1 IgG. Dashed lines represent the $D_{eff}$ cutoff below which particles are permanently trapped (moving less than their diameter within 1 s). Pearson's correlation coefficients (r) are indicated.

The present invention is based, in part, on the discovery and characterization of weak binding interactions between antibodies and mucins and the ability of such antibodies to stop the penetration of pathogens through mucus layers. The antibody-mucin interaction can be used advantageously in methods for preventing and treating infection, providing contraception, and monitoring the effectiveness of vaccines.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Except as otherwise indicated, standard methods known to those skilled in the art may be used for production of recombinant and synthetic polypeptides, antibodies or antigen-binding fragments thereof, manipulation of nucleic acid sequences, and production of transformed cells. Such techniques are known to those skilled in the art. See, e.g., SAMBROOK et al., MOLECULAR CLONING: A LABORATORY MANUAL 2nd Ed. (Cold Spring Harbor, N.Y., 1989); F. M. AUSUBEL et al. CURRENT PROTOCOLS IN MOLECULAR BIOLOGY (Green Publishing Associates, Inc. and John Wiley & Sons, Inc., New York).

All publications, patent applications, patents, nucleotide sequences, amino acid sequences and other references mentioned herein are incorporated by reference in their entirety.

Definitions

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

Moreover, the present invention also contemplates that in some embodiments of the invention, any feature or combination of features set forth herein can be excluded or omitted.

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units is also disclosed. For example, if 10 and 15 are disclosed, then 11, 12, 13, and 14 are also disclosed.

The transitional phrase "consisting essentially of" means that the scope of a claim is to be interpreted to encompass the specified materials or steps recited in the claim, "and those that do not materially affect the basic and novel characteristic(s)" of the claimed invention. See, In re Herz, 537 F.2d 549, 551-52, 190 USPQ 461, 463 (CCPA 1976) (emphasis in the original); see also MPEP § 2111.03.

As used herein, the term "polypeptide" encompasses both peptides and proteins, unless indicated otherwise.

A "nucleic acid" or "nucleotide sequence" is a sequence of nucleotide bases, and may be RNA, DNA or DNA-RNA hybrid sequences (including both naturally occurring and non-naturally occurring nucleotide), but is preferably either single or double stranded DNA sequences.

As used herein, an "isolated" antibody means an antibody separated or substantially free from at least some of the other components of the naturally occurring organism or virus, for example, the cell structural components or other polypeptides or nucleic acids commonly found associated with the antibody. The term also encompasses antibodies that have been prepared synthetically.

By the terms "treat," "treating," or "treatment of" (or grammatically equivalent terms) it is meant that the severity of the subject's condition is reduced or at least partially improved or ameliorated and/or that some alleviation, mitigation or decrease in at least one clinical symptom is achieved and/or there is a delay in the progression of the condition.

As used herein, the terms "prevent," "prevents," or "prevention" and "inhibit," "inhibits," or "inhibition" (and grammatical equivalents thereof) are not meant to imply complete abolition of disease and encompasses any type of prophylactic treatment that reduces the incidence of the condition, delays the onset of the condition, and/or reduces the symptoms associated with the condition after onset.

An "effective," "prophylactically effective," or "therapeutically effective" amount as used herein is an amount that is sufficient to provide some improvement or benefit to the subject. Alternatively stated, an "effective," "prophylactically effective," or "therapeutically effective" amount is an amount that will provide some delay, alleviation, mitigation, or decrease in at least one clinical symptom in the subject. Those skilled in the art will appreciate that the effects need not be complete or curative, as long as some benefit is provided to the subject.

As used herein, the term "trapping potency" refers to the ability of an antibody that specially binds to a target pathogen or sperm to inhibit movement of the pathogen or sperm through mucus. Trapping potency can be measured by methods known in the art and as disclosed herein. Trapping potency can be quantitated, e.g., as the amount of antibody (e.g., concentration of antibody in mucus) needed to reduce the mobility of at least 50% of the pathogen or sperm within the mucus gel to at least one-tenth of its mobility in solution (e.g., saline). Mobility in mucus can be measured using techniques well known in the art and described herein. Alternatively, trapping potency can be quantitated as the reduction in percentage of pathogens or sperm that penetrate mucus.

The term "enhances trapping potency" refers to an antibody comprising an oligosaccharide that provides an increased trapping potency relative to the trapping potency of antibodies as found in nature and/or antibodies prior to any modification and/or selection.

As used herein, the term "bind specifically" or "specifically binds" in reference to an antibody of the presently-disclosed subject matter means that the antibody of the invention will bind with an epitope (including one or more epitopes) of a target pathogen or sperm, but does not substantially bind to other unrelated epitopes or molecules. In certain embodiments, the term refers to an antibody that exhibits at least about 60% binding, e.g., at least about 70%, 80%, 90%, or 95% binding, to the target epitope relative to binding to other unrelated epitopes or molecules.

Antibodies and Compositions

The presently-disclosed subject matter includes antibodies, compositions, and methods for inhibiting and/or treating pathogen infection, eliminating pathogen from a mucosal surface, providing contraception, and/or monitoring the effectiveness of vaccines. In particular, the presently-disclosed subject matter relates to antibodies and compositions capable of trapping pathogens and sperm in mucus, thereby inhibiting transport of pathogens or sperm across or through mucus secretions.

The prevailing view of how antibodies protect a subject at mucosal surfaces assumes that neutralization of the pathogen is the primary mechanism of protection. Surprisingly and unexpectedly, in light of this widespread view, the present inventors disclose herein that neutralization is not necessary to protect against infection at mucosal surfaces in a subject. Indeed, it is demonstrated herein that sub-neutralization doses of antibodies to neutralizing epitopes of pathogens can be quite effective at inhibiting infection. Furthermore, it is demonstrated herein that use of antibodies to non-neutralizing epitopes of pathogens can also be quite effective at inhibiting infection.

Antibodies are naturally found in mucus. The current thoughts on antibody-mediated mucosal protection are that secretory IgA (sIgA) antibodies are important for protection because very large amounts of this isotype are found in the gastrointestinal tract. It is further thought that IgG does not play a role in mucosal protection. However, IgG is the dominant isotype in genital secretions and there is approximately a 50:50 ratio of IgG:IgA in respiratory mucus secretions. In contrast to the prevailing thought in the scientific community, it is shown herein that certain antibodies, e.g., IgG, found in CVM can diffuse rapidly through the CVM, slowed only slightly by weak, transient adhesive interactions with mucins within the mucus. This rapid diffusion allows antibodies to accumulate rapidly on pathogen or sperm surfaces. When a plurality of antibodies have accumulated on the surface of a pathogen, the adhesive interactions between the plurality of antibodies and the mucus become sufficient to trap the bound pathogen or sperm in the mucus, thereby preventing infection/providing contraception. Pathogens or sperm trapped in CVM cannot reach their target cells in the mucosal surface, and will instead be shed with post-coital discharge and/or inactivated by spontaneous thermal degradation as well as additional protective factors in mucus, such as defensins (Cole, Curr. Top. *Microbiol. Immunol.* 306:199 (2006); Doss et al., *J. Leukoc. Biol.* 87:79 (2010). As disclosed herein, this pathogen trapping activity provides for protection without neutralization, and can effectively inhibit infection at sub-neutralization doses and/ or using antibodies to non-neutralizing epitopes of a pathogen.

The present invention additionally provides the discovery that the low-affinity interactions that an antibody forms with mucins are not only Fe-dependent, but also influenced by antibody glycosylation.

Accordingly, the presently-disclosed subject matter includes an isolated antibody comprising an oligosaccharide at a glycosylation site, the oligosaccharide comprising, consisting essentially of, or consisting of a pattern correlating with (providing) enhanced trapping potency of the antibody in mucus, and wherein the antibody specifically binds an epitope of a target pathogen or sperm. The unique glycosylation pattern/unique oligosaccharide component of the antibody is designed to maximize trapping potency of the antibody once a plurality of antibodies are bound to the target pathogen or sperm, without unduly hindering the ability of the unbound antibody to diffuse readily through mucus to rapidly bind a target pathogen or sperm. In certain embodiments, the antibody is one that exhibits a mobility in mucus that is reduced no more than about 50%, e.g., no more than about 40%, 30, 20%, 10%, or 5%, relative to its mobility in solution (e.g., saline or water) and effectively traps a target pathogen or sperm in mucus based on a plurality of bound antibodies (e.g., at least 50% of pathogens or sperm slowed by at least 90%). In some embodiments, the antibody reduces the mobility of at least 50%, e.g., at least 60%, 70%, 80%, or 90% or more of the pathogen or sperm by at least 90%, e.g., at least 95%, 96%, 97%, 98%, or 99% or more. In other embodiments, the antibody reduces the percentage of pathogens or sperm that can penetrate mucus by at least 10%, e.g., at least 20%, 30%, 40%, 50%, 60%, 70%, 80%, 90%, or more. Based on the disclosure herein, one of skill in the art can readily identify/design oligosaccharide patterns that provide the desired trapping potency. In other embodiments, the antibody has a sufficient binding rate to an epitope of the target pathogen or sperm to accumulate on the surface of the target pathogen or sperm at sufficient levels to trap the target pathogen or sperm in mucus within one hour (e.g., within 30 minutes or 15 minutes) at an antibody concentration in the mucus of less than 5 µg/mL (e.g., less than 1 µg/mL or 0.1 µg/mL).

In some embodiments, the oligosaccharide component is bound to an N-linked glycosylation site in an Fc region of the antibody. The N-linked glycosylation site can be an asparagine residue on the Fc region of the antibody, for example, the Asn 297 asparagine residue. The amino acid numbering is with respect to the standard amino acid structure of a human IgG molecule.

Figure 12:
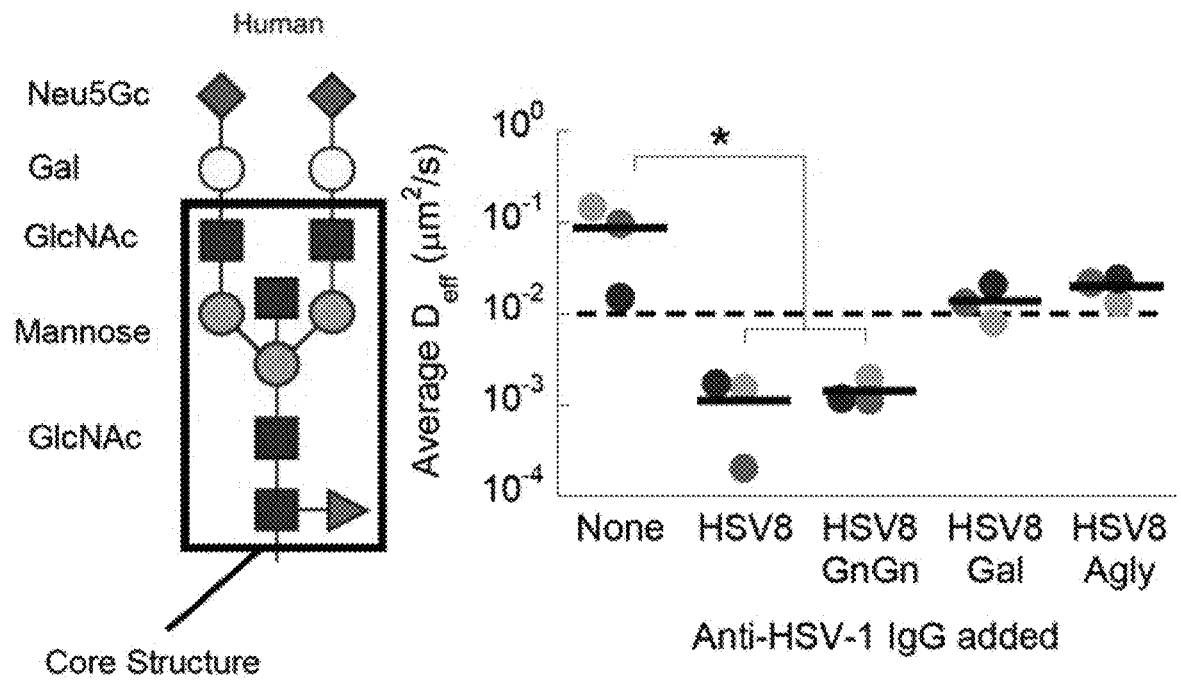
FIG. 12 shows the role of N-glycans in IgG-mucin interactions. In the oligosaccharide structure, the square is N-acetylglucosamine (GlcNAc), the triangle is fucose, the diamond is sialic acid (Neu5Gc), the light gray circle is galactose (Gal), and the dark gray circle is mannose.

The N-glycan structure on human IgG-Fc is typically dominated by a biantennary core structure that shares a common core sugar sequence (as shown in FIG. 12), Manα1-6(Manα1-3)Manβ1-4GlcNAcβ1-4GlcNAcβ1-Asn-X-Ser/Thr, with "antennae" initiated by N-acetylglucosaminyltransferases (GlcNAcTs) that help attach additional sugars to the core. In IgG found in human serum, the most common structures are those that contain both N-acetylglucosamine on each branch with one terminal galactose (39%), two terminal galactose (20%), or one terminal galactose and one terminal sialic acid (15%). Together, antibodies that comprise at least one terminal galactose represents about 74% of the IgG-Fc glycoforms. A pure GnGn form (with terminal N-acetylglucosamine on each branch without terminal galactose or sialic acid) represents about 26% of the IgG-Fc glycoforms.

In some embodiments, the oligosaccharide component, i.e., the glycan, attached to the antibody comprises, consists essentially of, or consists of the core structure depicted in FIG. 12. In some embodiments, the glycan attached to the antibody comprises, consists essentially of, or consists of the core structure depicted in FIG. 12 minus the fucose residue. In some embodiments, the glycan comprises, consists essentially of, or consists of the full structure depicted in FIG. 12. In other embodiments, the glycan does not contain any galactose residues. In certain embodiments, the glycan comprises the core structure as depicted in FIG. 12 and additional saccharide residues that do not include galactose. Without being limited by theory, it is believed that the presence of galactose compromises trapping potency. Antibodies with glycoforms that do not contain galactose represent just a small fraction of the entire repertoire of glycoforms found in nature. The use of a population of antibodies enriched with desirable glycoforms (whether naturally occurring or modified glycans) is advantageously used for trapping pathogens and sperm in mucus.

In some embodiments, the antibody of the invention is a mixture of antibodies having different oligosaccharide components. In some embodiments, the mixture of antibodies comprises at least about 30% antibodies having the core glycan structure depicted in FIG. 12 with or without the fucose residue, e.g., at least about 40%, 50%, 60%, 70%, 80%, 90% or more. In other embodiments, the mixture of antibodies comprises at least about 5% antibodies having the full glycan structure depicted in FIG. 12, e.g., at least about 10%, 20%, 30%, 40%, 50%, 60%, 70%, 80%, 90% or more. In some embodiments, the mixture of antibodies comprises at least about 30% antibodies having the core glycan structure depicted in FIG. 12, e.g., at least about 40%, 50%, 60%, 70%, 80%, 90% or more and at least about 5% antibodies having the full glycan structure depicted in FIG. 12, e.g., at least about 10%, 20%, 30%, 40%, 50%, 60%, 70%, 80%, 90% or more.

In some embodiments, the mixture of antibodies is the mixture generated in a human cell line, e.g., a 293 cell line, e.g., a 293T cell line.

The antibody is useful for binding target pathogens to trap the pathogen in mucus to inhibit infection by the pathogen. Target pathogens of the antibody can include any pathogen that can infect a subject through a mucus membrane. Pathogens can be in the categories of algae, bacteria, fungi, parasites (helminths, protozoa), viruses, and subviral agents. Target pathogens further include synthetic systems comprising an antigen having an epitope, for example particles or particulates (e.g., polystyrene beads) comprising attached proteins, e.g., as might be used for bioterrorism.

Pathogens include those that cause sexually-transmitted diseases (listed with the diseases caused by such pathogens), including, without limitation, *Neisseria gonorrhoeae* (gonorrhea); *Chlamydia trachomatis* (chlamydia, lymphogranuloma venereum); *Treponema pallidum* (syphilis); *Haemophilus ducreyi* (chancroid); *Klebsiella granulomatis* or *Calymmatobacterium granulomatis* (donovanosis), *Mycoplasma genitalium, Ureaplasma urealyticum* (mycoplasmas); human immunodeficiency virus HIV-1 and HIV-2 (HIV, AIDS); HTLV-1 (T-lymphotrophic virus type 1); herpes simplex virus type 1 and type 2 (HSV-1 and HSV-2); Epstein-Barr virus; cytomegalovirus; human herpesvirus 6; varicella-zoster virus; human papillomaviruses (genital warts); hepatitis A virus, hepatitis B virus, hepatitis C virus (viral hepatitis); molluscum contagiosum virus (MCV); Trichomona *vaginalis* (trichomoniasis); and yeasts, such as *Candida albicans* (vulvovaginal candidiasis). The antibodies and compositions may also be active against other diseases that are transmitted by contact with bodily fluids that may also be transmissible by sexual contact and are capable of being prevented by administration of the compositions according to this invention. Accordingly, the phrase, "sexually transmitted diseases (STDs)," is to be interpreted herein as including any disease that is capable of being transmitted in the course of sexual contact, whether or not the genital organs are the site of the resulting pathology.

Pathogens also include those that cause respiratory diseases, including, without limitation, influenza (including influenza A, B, and C); severe acute respiratory syndrome (SARS); respiratory syncytial virus (RSV); parainfluenza; adenovirus; human rhinovirus; coronavirus; and norovirus.

Other pathogens include, without limitation, *Salmonella* and *Escherichia coli*.

Pathogens include those that affect non-human animals, such as livestock, e.g., swine (e.g., porcine epidemic diarrhea virus (PEDV), transmissible gastroenteritis virus (TGEV), rotavirus, classical swine fever virus (CSFV), porcine circovirus type 2 (PCV2), encephalomyocarditis virus (EMCV), porcine reproductive and respiratory syndrome virus (PRRSV), porcine parvovirus (PPV), pseudorabies virus (PRV), Japanese encephalitis virus (JEV), *Brucella, Leptospira, Salmonella*, and *Lawsonia intracellularis, Pasteurella multocida, Brachyspira hyodysenteriae, Mycoplasma hyopneumoniae*), ruminants (e.g., bovine virus diarrhoea virus (BVDV), border disease virus (BDV), bovine papular stomatitis virus (BPSV), pseudocowpox virus (PCPV), *Pasteurella haemolytica, Pasteurella multocida, Haemophilus somnus, Haemophilus agnii, Moraxella bovis, Mycoplasma mycoides, Theileria annulata, Mycobacterium avium* paratuberculosis), ungulates (e.g., *Brucella abortus, Mycobacterium bovis, Theileria parva*, Rift Valley fever virus, foot-and-mouth disease virus, lumpy skin disease virus), horses (e.g., *Rhodococcus equi, Salmonella choleraesuis, Pasteurella multocida*, equine herpesvirus-1, equine herpesvirus-4, equine influenza virus, *Streptococcus equi*), poultry (e.g., fowl pox virus, Newcastle disease virus, Marek's disease virus, avian influenza virus, infectious bursal disease virus (IBDV), avian infectious bronchitis virus (IBV)), and the like.

The terms virus and viral pathogen are used interchangeably herein, and further refer to various strains of virus, e.g., influenza is inclusive of new strains of influenza, which would be readily identifiable to one of skill in the art. The terms bacterium, bacteria, and bacterial pathogen are used interchangeably herein, and further refer to antibiotic-resistant or multidrug resistant strains of bacterial pathogens. As used herein when referring to a bacterial pathogen, the term "antibiotic-resistant strain" or "multidrug resistant strain" refers to a bacterial pathogen that is capable of withstanding an effect of an antibiotic or drug used in the art to treat the bacterial pathogen (i.e., a non-resistant strain of the bacterial pathogen).

In some embodiments, it is contemplated that an antibody according to the presently-disclosed subject matter is capable of broadly binding to viruses containing lipid envelopes, which are not necessarily specific to one virus.

As noted above, it was surprisingly discovered that sub-neutralization doses of an antibody can be used to effectively trap a target pathogen or sperm in mucus. As such, in some embodiments, wherein the antibody specifically binds a neutralizing epitope of the target pathogen, a sub-neutralization dose can be used. A sub-neutralization doses is a dose below that which would be needed to achieve effective neutralization. For example, in the case of polyclonal anti-HSV gG antibodies targeting HSV, as described hereinbelow, an effective neutralization dose is approximately 5 µg/mL. However, effective trapping using the antibody can be achieved at a dose below 5 µg/mL, and even below a dose of 1 µg/mL.

As will be recognized by one of skill in the art, doses appropriate for trapping bacterial pathogens can be higher in some embodiments than the doses appropriate for trapping viral pathogens. It will further be recognized that appropriate doses may differ between pathogens, between mucosal surfaces, and also between individuals. It will also be recognized that different subjects and different mucosal surfaces may have different optimal glycan patterns and optimal antibody-mucin affinities, contributing to different optimal doses.

It is further proposed herein that antibodies that selectively bind non-neutralizing epitopes of a target pathogen can be used to effectively trap the target pathogen in mucus. As such, in some embodiments, the antibody specifically binds a non-neutralizing epitope, e.g., one or more non-neutralizing epitopes.

The presently-disclosed subject matter further includes an antibody that selectively binds a conserved epitope of a target pathogen, A benefit of targeting a conserved epitope would be to preserve efficacy of the antibody as against new strains of the pathogen. Targeting such epitopes has been avoided at times in the past because they were viewed as being ineffective targets; however, in view of the disclosure herein that non-neutralizing epitopes can serve as effective targets and/or that sub-neutralization doses can be effective for inhibiting infection, previously dismissed conserved epitopes of target pathogens can be seen as effective targets.

Antibodies of the invention are useful for binding sperm to trap the sperm in mucus to inhibit fertilization of an egg by the sperm. Sperm specific antigens that can be used as antibody targets are well known in the art. See, e.g., U.S. Pat. Nos. 8,211,666, 8,137,918, 8,110,668, 8,012,932, 7,339,029, 7,230,073, and 7,125,550, each incorporated by reference in its entirety.

As noted above, it was determined that the low-affinity binding interactions that an antibody forms with mucins are influenced by antibody glycosylation, and are also Fc-dependent. As such, the presently-disclosed subject matter includes antibodies having a preserved and/or engineered Fc region. Such antibodies can be, for example, one or more of IgG, IgA, IgM, IgD, or IgE. In certain embodiments, the antibodies are IgG. In some embodiments, the antibodies are one or more subclasses of IgG, e.g., IgG$_1$, IgG$_2$, IgG$_3$, IgG$_4$, or any combination thereof.

In some embodiments, the antibody has a sufficient binding rate and/or binding affinity to an epitope of the target pathogen or sperm to accumulate on the surface of the pathogen or sperm at sufficient levels to trap the pathogen or sperm within one hour after administration of the antibody at an antibody concentration of less than about 5 µg/mL. The term "trap" in this instance refers to reduction of further movement through the mucus. In some embodiments, the target pathogen or sperm is trapped within about 30 minutes, e.g., about 25, 20, 15, or 10 minutes after administration of the antibody. In some embodiments, the antibody traps the target pathogen or sperm at an antibody concentration of less than about 4, 3, 2, or 1 µg/mL.

The following discussion is presented as a general overview of the techniques available for the production of antibodies; however, one of skill in the art will recognize that many variations upon the following methods are known.

The term "antibody" or "antibodies" as used herein refers to all types of immunoglobulins, including IgG, IgM, IgA, IgD, and IgE. The antibody can be monoclonal or polyclonal and can be of any species of origin, including (for example) mouse, rat, rabbit, horse, goat, sheep, camel, or human, or can be a chimeric or humanized antibody. See, e.g., Walker et al., *Molec. Immunol.* 26:403 (1989). The antibodies can be recombinant monoclonal antibodies produced according to the methods disclosed in U.S. Pat. No. 4,474,893 or 4,816,567, The antibodies can also be chemically constructed according to the method disclosed in U.S. Pat. No. 4,676,980.

Antibody fragments included within the scope of the present invention include, for example, Fab, Fab', F(ab)$_2$, and Fv fragments; domain antibodies, diabodies; vaccibodies, linear antibodies; single-chain antibody molecules; and multispecific antibodies formed from antibody fragments. Such fragments can be produced by known techniques. For example, F(ab')$_2$ fragments can be produced by pepsin digestion of the antibody molecule, and Fab fragments can be generated by reducing the disulfide bridges of the F(ab')$_2$ fragments. Alternatively, Fab expression libraries can be constructed to allow rapid and easy identification of monoclonal Fab fragments with the desired specificity (Huse et al., *Science* 254:1275 (1989)). In some embodiments, the term "antibody fragment" as used herein may also include any protein construct that is capable of binding a target pathogen or sperm and associate with mucin to trap the target pathogen or sperm in mucus.

Antibodies of the invention may be altered or mutated for compatibility with species other than the species in which the antibody was produced. For example, antibodies may be humanized or camelized. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementarity determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework (FR) regions (i.e., the sequences between the CDR regions) are those of a human immunoglobulin consensus sequence. The humanized antibody optimally also will comprise at least a portion of an immunoglobulin constant region (Fe), typically that of a human immunoglobulin (Jones et al., *Nature* 321:522 (1986); Riechmann et al., *Nature,* 332:323 (1988); and Presta, *Curr. Op. Struct. Biol.* 2:593 (1992)).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can essentially be performed following the method of Winter and co-workers (Jones et al., *Nature* 321:522 (1986); Riechmann et al., *Nature* 332:323 (1988); Verhoeyen et al., *Science* 239:1534 (1988)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues (e.g., all of the CDRs or a portion thereof) and possibly some FR residues are substituted by residues from analogous sites in rodent antibodies.

Human antibodies can also be produced using various techniques known in the art, including phage display libraries (Hoogenboom and Winter, *J. Mol. Biol.* 227:381 (1991); Marks et al., *J. Mol. Biol.* 222:581 (1991)). The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.* 147:86 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10:779 (1992); Lonberg et al., *Nature* 368:856 (1994); Morrison, *Nature* 368:812 (1994); Fishwild et al., *Nature Biotechnol.* 14:845 (1996); Neuberger, *Nature Biotechnol.* 14:826 (1996); Lonberg and Huszar, *Intern. Rev. Immunol.* 13:65 (1995).

Immunogens (antigens) are used to produce antibodies specifically reactive with target polypeptides. Recombinant or synthetic polypeptides and peptides, e.g., of at least 5 (e.g., at least 7 or 10) amino acids in length, or greater, are the preferred immunogens for the production of monoclonal or polyclonal antibodies. In one embodiment, an immunogenic polypeptide conjugate is also included as an immunogen. The peptides are used either in pure, partially pure or impure form. Suitable polypeptides and epitopes for target pathogens and sperm are well known in the art. Polynucleotide and polypeptide sequences are available in public sequence databases such as GENBANK®/GENPEPT®. Large numbers of neutralizing and non-neutralizing antibodies that specifically bind to target pathogens and sperm have been described in the art and can be used as starting material to prepare the antibodies of the present invention. Alternatively, new antibodies can be raised against target pathogens and sperm using the techniques described herein and well known in the art.

Recombinant polypeptides are expressed in eukaryotic or prokaryotic cells and purified using standard techniques. The polypeptide, or a synthetic version thereof, is then injected into an animal capable of producing antibodies. Either monoclonal or polyclonal antibodies can be generated for subsequent use in immunoassays to measure the presence and quantity of the polypeptide.

Methods of producing polyclonal antibodies are known to those of skill in the art. In brief, an immunogen, e.g., a purified or synthetic peptide, a peptide coupled to an appropriate carrier (e.g., glutathione-S-transferase, keyhole limpet hemocyanin, etc.), or a peptide incorporated into an immunization vector such as a recombinant vaccinia virus is optionally mixed with an adjuvant and animals are immunized with the mixture. The animal's immune response to the immunogen preparation is monitored by taking test bleeds and determining the titer of reactivity to the peptide of interest. When appropriately high titers of antibody to the immunogen are obtained, blood is collected from the animal and antisera are prepared. Further fractionation of the antisera to enrich for antibodies reactive to the peptide is performed where desired. Antibodies, including binding fragments and single chain recombinant versions thereof, against the polypeptides are raised by immunizing animals, e.g., using immunogenic conjugates comprising a polypeptide covalently attached (conjugated) to a carrier protein as described above. Typically, the immunogen of interest is a polypeptide of at least about 10 amino acids, in another embodiment the polypeptide is at least about 20 amino acids in length, and in another embodiment, the fragment is at least about 30 amino acids in length. For example, the polypeptide can comprise amino acids acid residues 1 through 200 from the N-terminal of the papillomavirus L2 protein. The immunogenic conjugates are typically prepared by coupling the polypeptide to a carrier protein (e.g., as a fusion protein) or, alternatively, they are recombinantly expressed in an immunization vector.

Monoclonal antibodies are prepared from cells secreting the desired antibody. These antibodies are screened for binding to normal or modified peptides, or screened for agonistic or antagonistic activity. Specific monoclonal and polyclonal antibodies will usually bind with a $K_D$ of at least about 50 mM, e.g., at least about 1 mM, e.g., at least about 0.1 mM or better. In some instances, it is desirable to prepare monoclonal antibodies from various mammalian hosts, such as mice, rodents, primates, humans, etc. Description of techniques for preparing such monoclonal antibodies are found in Kohler and Milstein 1975 *Nature* 256:495-497. Summarized briefly, this method proceeds by injecting an animal with an immunogen, e.g., an immunogenic peptide either alone or optionally linked to a carrier protein. The animal is then sacrificed and cells taken from its spleen, which are fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Alternative methods of immortalization include transformation with Epstein Barr Virus, oncogenes, or retroviruses, or other methods known in the art. Colonies arising from single immortalized cells are screened for production of antibodies of the desired specificity and affinity for the antigen, and yield of the monoclonal antibodies produced by such cells is enhanced by various techniques, including injection into the peritoneal cavity of a vertebrate (preferably mammalian) host. The polypeptides and antibodies of the present invention are used with or without modification, and include chimeric antibodies such as humanized murine antibodies. Other suitable techniques involve selection of libraries of recombinant antibodies in phage or similar vectors. See, Huse et al. 1989 *Science* 246:1275-1281; and Ward et al. 1989 *Nature* 341:544-546.

Antibodies specific to the target polypeptide can also be obtained by phage display techniques known in the art.

Antibodies can sometimes be labeled by joining, either covalently or noncovalently, a substance which provides a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Such antibodies are useful for detecting or diagnosing the presence of a microbe on which an antigen is found.

Method of making antibodies with a glycosylation pattern of interest can be achieved by any method known to those or skill in the art. For example, in some embodiments, mammalian cells can be used, such as, Chinese hamster ovary (CHO) cells, baby hamster kidney (BHK) cells, and NS0- and SP2/0-mouse myeloma cells, to produce antibodies having the desired glycosylation pattern. In certain embodiments, human cell lines can be used, e.g., 293 cells. In some embodiments, non-mammalian cells can be used. The cell line can be genetically engineered to produce the antibodies with the desired oligosaccharide. Such cell lines can have altered expression, for example, of one or more enzymes affecting glycosylation patterns, e.g., glycosyltransferases. Glycosyltransferases include, without limitation, a galactosyltransferase, a fucosyltransferase, a glucosyltransferase, an N-acetylgalactosaminyltransferase, an N-acetylglucosaminyltransferase, a glucuronyltransferase, a sialyltransferase, a mannosyltransferase, a glucuronic acid transferase, a galacturonic acid transferase, an oligosaccharyltransferase, or any combination thereof. Specific examples include, without limitation, oligosaccharyltransferase, UDP-N-acetyl-D-galactosamine:polypeptide N-acetylgalactosaminyltransferase, GDP-fucose protein:O-fucosyltransferase 1, GDP-fucose protein:O-fucosyltransferase 2, protein:O-glucosyltransferase, UDP-N-acetylglucosamine:peptide N-acetylglucosaminyltransferase, protein:O-mannosyltransferase, β1,4 galactosyltransferase, and any combination thereof. Enzymes involved in glycosylation of proteins are well known in the art and can be manipulated using routine techniques. See, for example, U.S. Pat. Nos. 8,383,106, 8,367,374, 8,080,415, 8,025,879, 8,021,856, 7,906,329, and 7,846,434, each incorporated herein by reference in its entirety. In other embodiments, glycans can be synthesized in specific patterns and linked to antibodies. In further embodiments, antibodies with mixed glycosylation patterns can be separated to isolate antibodies with the desired glycosylation pattern.

As would be recognized by one skilled in the art, the antibodies of the presently-disclosed subject matter can also be formed into suitable compositions, e.g., pharmaceutical compositions for administration to a subject in order to treat or prevent an infection caused by a target pathogen or a disease or disorder caused by infection by a target pathogen or to provide contraception. In one embodiment, the compositions comprise, consist essentially of, or consist of an antibody of the invention in a prophylactically or therapeutically effective amount and a pharmaceutically-acceptable carrier.

Pharmaceutical compositions containing the antibodies as disclosed herein can be formulated in combination with any suitable pharmaceutical vehicle, excipient or carrier that would commonly be used in this art, including such conventional materials for this purpose, e.g., saline, dextrose, water, glycerol, ethanol, and combinations thereof. As one skilled in this art would recognize, the particular vehicle, excipient or carrier used will vary depending on the subject and the subject's condition, and a variety of modes of administration would be suitable for the compositions of the invention. Suitable methods of administration of any pharmaceutical composition disclosed in this application include, but are not limited to, topical, oral, intranasal, buccal, inhalation, anal, and vaginal administration, wherein such administration achieves delivery of the antibody to a mucus membrane of interest.

The composition can be any type of composition suitable for delivering antibody to a mucosal surface and can be in various forms known in the art, including solid, semisolid, or liquid form or in lotion form, either oil-in-water or water-in-oil emulsions, in aqueous gel compositions. Compositions include, without limitation, gel, paste, suppository, douche, ovule, foam, film, spray, ointment, pessary, capsule, tablet, jelly, cream, milk, dispersion, liposomes, powder/talc or other solid, suspension, solution, emulsion, microemulsion, nanoemulsion, liquid, aerosol, microcapsules, time-release capsules, controlled release formulation, sustained release formulation or bioadhesive gel (e.g., a mucoadhesive thermogelling composition) or in other forms embedded in a matrix for the slow or controlled release of the antibody to the surface onto which it has been applied or in contact.

If topical administration is desired, the composition may be formulated as needed in a suitable form, e.g., an ointment, cream, gel, lotion, drops (such as eye drops and ear drops), or solution (such as mouthwash). The composition may contain conventional additives, such as preservatives, solvents to promote penetration, and emollients. Topical formulations may also contain conventional carriers such as cream or ointment bases, ethanol, or oleyl alcohol. Other formulations for administration, including intranasal administration, etc., are contemplated for use in connection with the presently-disclosed subject matter. All formulations, devices, and methods known to one of skill in the art which are appropriate for delivering the antibody or composition containing the antibody to one or more mucus membranes of a subject can be used in connection with the presently-disclosed subject matter.

The compositions used in the methods described herein may include other agents that do not negatively impact or otherwise affect the inhibitory and/or contraceptive effectiveness of the components of the composition, including antibodies, antimicrobial agents, and/or sperm-function inhibitors. For example, solid, liquid or a mixture of solid and liquid pharmaceutically acceptable carriers, diluents, vehicles, or excipients may be employed in the pharmaceutical compositions. Suitable physiologically acceptable, substantially inert carriers include water, a polyethylene glycol, mineral oil or petrolatum, propylene glycol, hydroxyethyl-cellulose, carboxymethyl cellulose, cellulosic derivatives, polycarboxylic acids, linked polyacrylic acids, such as carbopols; and other polymers such as poly(lysine), poly(glutamic acid), poly(maleic acid), polylactic acid), thermal polyaspartate, and aliphatic-aromatic resin; glycerin, starch, lactose, calcium sulphate dihydrate, terra alba, sucrose, talc, gelatin, pectin, acacia, magnesium stearate, stearic acid, syrup, peanut oil, olive oil, saline solution, and the like.

The pharmaceutical compositions described herein useful in the methods of the present invention may further include diluents, fillers, binding agents, colorants, stabilizers, perfumes, gelling agents, antioxidants, moisturizing agents, preservatives, acids, and other elements known to those skilled in the art. For example, suitable preservatives are well known in the art, and include, for example, methyl paraben, propyl paraben, butyl paraben, benzoic acid and benzyl alcohol.

For injection, the carrier will typically be a liquid, such as sterile pyrogen-free water, pyrogen-free phosphate-buffered saline solution, bacteriostatic water, or Cremophor EL® (BASF, Parsippany, N.J.). For other methods of administration, the carrier can be either solid or liquid.

For oral administration, the antibody can be administered in solid dosage forms, such as capsules, tablets, and powders, or in liquid dosage forms, such as elixirs, syrups, and suspensions. Compositions can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that can be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Compositions suitable for buccal (sub-lingual) administration include tablets or lozenges comprising the antibody in a flavored base, usually sucrose and acacia or tragacanth; and pastilles comprising the antibody in an inert base such as gelatin and glycerin or sucrose and acacia. The composition can comprise an orally dissolvable or degradable composition. Alternately, the composition can comprise a powder or an aerosolized or atomized solution or suspension comprising the antibody. Such powdered, aerosolized, or atomized compositions, when dispersed, preferably have an average particle or droplet size in the range from about 0.1 to about 200 nanometers.

Compositions of the present invention suitable for parenteral administration comprise sterile aqueous and non-aqueous injection solutions of the antibody, which preparations are preferably isotonic with the blood of the intended recipient. These preparations can contain anti-oxidants, buffers, bacteriostats and solutes which render the composition isotonic with the blood of the intended recipient. Aqueous and non-aqueous sterile suspensions can include suspending agents and thickening agents. The compositions can be presented in unit/dose or multi-dose containers, for example sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, in one aspect of the present invention, there is provided an injectable, stable, sterile composition comprising an antibody, in a unit dosage form in a sealed container. The antibody is provided in the form of a lyophilizate which is capable of being reconstituted with a suitable pharmaceutically acceptable carrier to form a liquid composition suitable for injection thereof into a subject.

Compositions suitable for rectal administration are preferably presented as unit dose suppositories. These can be prepared by admixing the antibody with one or more conventional solid carriers, for example, cocoa butter, and then shaping the resulting mixture.

The antibody can alternatively be formulated for nasal administration or otherwise administered to the lungs of a subject by any suitable means, e.g., administered by an aerosol suspension of respirable particles comprising the antibody, which the subject inhales. The respirable particles can be liquid or solid. The term "aerosol" includes any gas-borne suspended phase, which is capable of being inhaled into the bronchioles or nasal passages. Specifically, aerosol includes a gas-borne suspension of droplets, as can be produced in a metered dose inhaler or nebulizer, or in a mist sprayer. Aerosol also includes a dry powder composition suspended in air or other carrier gas, which can be delivered by insufflation from an inhaler device, for example. See Ganderton & Jones, *Drug Delivery to the Respiratory Tract*, Ellis Harwood (1987); Gonda (1990) *Critical Reviews in Therapeutic Drug Carrier Systems* 6:273-313; and Raeburn et al., *J. Pharmacol. Toxicol. Meth.* 27:143 (1992). Aerosols of liquid particles comprising the antibody can be produced by any suitable means, such as with a pressure-driven aerosol nebulizer or an ultrasonic nebulizer, as is known to those of skill in the art. See, e.g., U.S. Pat. No. 4,501,729. Aerosols of solid particles comprising the antibody can likewise be produced with any solid particulate medicament aerosol generator, by techniques known in the pharmaceutical art.

Alternatively, one can administer the antibody in a local rather than systemic manner, for example, in a depot or sustained-release formulation.

One aspect of the invention relates to devices coated or impregnated with the antibodies and compositions of the invention. The device can be for delivery of the antibodies and compositions of the invention to a mucus membrane, e.g., to the vagina or uterus. In one embodiment, a device includes a solid support adapted to be inserted into the vagina. The support can be impregnated with or coated with a composition. The release of antibodies from the devices may be controlled by the material composing these devices, such as silicone elastomers, ethylene vinyl acetate and polyurethane polymers. Devices, such as cervicovaginal and rectal devices, include, without limitation, a ring, rod, applicator, sponge, cervical cap, tampon, diaphragm, or intrauterine device. Applicators can be those currently used commercially to deliver spermicidal gels or anti-yeast compounds and include, without limitation, plunger-type applicators, pessaries, sprays, squeezable tubes, vaginal rings, cervical rings, sponges, and the like. All such means for delivery are intended to be encompassed by the present invention.

As noted herein, antibodies of the presently-disclosed subject matter are capable of diffusing through mucus when they are unbound, to allow the antibody to bind a target pathogen or sperm at a desirable rate. It is also desirable that, when antibodies are bound to the pathogen or sperm, the cumulative effect of the antibody-mucin interactions effectively traps the pathogen or sperm in the mucus. To facilitate this goal, in some embodiments, it can be desirable to provide a composition that includes more than one antibody, wherein each antibody specifically binds a different epitope of the target pathogen or sperm. Such a composition provides the ability for an increased number of antibodies to become bound to the pathogen or sperm, thereby strengthening the antibody-mucin interactions that serve to trap the pathogen or sperm in the mucus.

In some embodiments of the presently-disclosed subject matter, a composition includes a first antibody and a second antibody, as disclosed herein, wherein the first antibody specifically binds a first epitope of the target pathogen or sperm and the second antibody specifically binds a second epitope of the target pathogen or sperm, wherein said first epitope is distinct from the second epitope. In certain embodiments, the composition includes three or more different antibodies, e.g., 3, 4, 5, 6, 7, 8, 9, 10, or more different antibodies, wherein each antibody specifically binds a different epitope of the target pathogen or sperm.

In some embodiments of the presently-disclosed subject matter, a composition includes a first antibody that specifically binds a gG surface glycoprotein of HSV, a second antibody that specifically binds a gD surface glycoprotein of HSV, and/or a third antibody that specifically binds a gB surface glycoprotein of HSV.

It is also desirable to provide a composition that can provide treatment or prevention of infection due to more than one target pathogen. In some embodiments of the presently-disclosed subject matter, a composition includes a first antibody and a second antibody, as disclosed herein, wherein the first antibody specifically binds an epitope of a first target pathogen and the second antibody specifically binds an epitope of second target pathogen. In certain embodiments, the composition includes three or more different antibodies, e.g., 3, 4, 5, 6, 7, 8, 9, 10, or more different antibodies, wherein each antibody specifically binds an epitope of a different target pathogen.

In other embodiments, a composition provides both contraception and treatment or prevention of infection by one or more target pathogens. In some embodiments of the presently-disclosed subject matter, a composition includes a first antibody and a second antibody, as disclosed herein, wherein the first antibody specifically binds an epitope of sperm and the second antibody specifically binds an epitope of a target pathogen. In certain embodiments, the composition includes three or more different antibodies, e.g., 3, 4, 5, 6, 7, 8, 9, 10, or more different antibodies, wherein one or more antibodies bind different epitopes of sperm and one or more antibodies specifically binds an epitope of a target pathogen or multiple target pathogens.

In some embodiments, the pharmaceutical composition can further include an additional active agent, e.g., a prophylactic or therapeutic agent. For example, the additional active agent can be an antimicrobial agent, as would be known to one of skill in the art. The antimicrobial agent may be active against algae, bacteria, fungi, parasites (helminths, protozoa), viruses, and subviral agents. Accordingly, the antimicrobial agent may be an antibacterial, antifungal, antiviral, antiparasitic, or antiprotozoal agent. The antimicrobial agent is preferably active against infectious diseases.

Suitable antiviral agents include, for example, virus-inactivating agents such as nonionic, anionic and cationic surfactants, and C31 G (amine oxide and alkyl betaine), polybiguanides, docosanol, acylcarnitine analogs, octyl glycerol, and antimicrobial peptides such as magainins, gramicidins, protegrins, and retrocyclins. Mild surfactants, e.g., sorbitan monolaurate, may advantageously be used as antiviral agents in the compositions described herein. Other antiviral agents that may advantageously be utilized in the compositions described herein include nucleotide or nucleoside analogs, such as tenofovir, acyclovir, amantadine, didanosine, foscarnet, ganciclovir, ribavirin, vidarabine, zalcitabine, and zidovudine. Further antiviral agents that may be used include non-nucleoside reverse transcriptase inhibitors, such as UC-781 (thiocarboxanilide), pyridinones, TIBO, nevaripine, delavirdine, calanolide A, capravirine and efavirenz. From these reverse transcriptase inhibitors, agents and their analogs that have shown poor oral bioavailability are especially suitable for administration to mucosal tissue, in combination with antibodies and compositions of the invention, to prevent sexual transmission of HIV. Other antiviral agents that may be used are those in the category of HIV entry blockers, such as cyanovirin-N, cyclodextrins, carregeenans, sulfated or sulfonated polymers, mandelic acid condensation polymers, monoclonal antibodies, chemokine receptor antagonists such as TAK-779, SCH-C/D, and AMD-3100, and fusion inhibitors such as T-20 and 1249.

Suitable antibacterial agents include antibiotics, such as aminoglycosides, cephalosporins, including first, second and third generation cephalosporins; macrolides, including erythromycins, penicillins, including natural penicillins, penicillinase-resistant penicillins, aminopenicillins, extended spectrum penicillins; sulfonamides, tetracyclines, fluoroquinolones, metronidazole and urinary tract antiseptics.

Suitable antifungal agents include amphotericin B, nystatin, griseofulvin, flucytosine, fluconazole, potassium iodide, intraconazole, clortrimazole, miconazole, ketoconazole, and tolnaftate.

Suitable antiprotozoal agents include antimalarial agents, such as chloroquine, primaquine, pyrimethamine, quinine, fansidar, and mefloquine; amebicides, such as dioloxamide, emetine, iodoquinol, metronidazole, paromomycine and quinacrine; pentamidine isethionate, atovaquone, and eflornithine.

In certain embodiments, the additional active agent can be a sperm-function inhibitor, e.g., an agent that has the ability to inhibit the function of sperm, to otherwise inhibit fertilization of an egg by sperm and/or to otherwise prevent pregnancy, such as by killing and/or functionally inactivating sperm or by other effects on the activity of the sperm. In some embodiments, the active agent may have at least dual functions, such as acting as a sperm-function inhibitor and as an antimicrobial agent.

Sperm-function inhibitors include, without limitation, surfactants, including nonionic surfactants, cationic surfactants, and anionic surfactants; spermicides, such as nonoxynol-9 (α-(4-Nonylphenyl)-ω-hydroxynona(oxyethylene); other sperm-inactivators such as sulfated or sulfonated polymers such as polystyrene sulfonate, mandelic acid condensation polymers, cyclodextrins; antimicrobial peptides such as gramicidins, magainins, indolicidin, and melittin; and acid-buffering compositions, such as BufferGel and Acid-Form. Nonionic surfactants include, for example, sorbitan monolaurate, nonylphenoxypolyethoxy ethanol, p-diisobutyphenoxypolyethoxy ethanol, polyoxyethylene (10) oleyl ether and onyx-ol. Suitable anionic surfactants include, without limitation, sodium alkyl sulfonates and the sodium alkylbenzene sulfonates. Cationic surfactants include, for example, the quaternary ammonium surfactants, such as cetyl pyrimidinium chloride and benzalkonium chlorides. Zwitterionic surfactants such as acylcarnitine analogs and C31G are especially suitable for their mild skin and mucosal irritation properties.

The presently-disclosed subject matter further includes a kit, including the antibody or composition comprising the antibody as described herein; and optionally a device for administering the antibody or composition. In some embodiments, the kit can include multiple antibodies and/or compositions containing such antibodies. In some embodiments, each of multiple antibodies provided in such a kit can specifically bind to a different epitope of the target pathogen or sperm. In other embodiments, each of multiple antibodies provided in such a kit can specifically bind to an epitope of a different target pathogen or to an epitope of sperm. In some embodiments, the kit can further include an additional active agent, e.g., an antimicrobial, such as an antibiotic, an antiviral, or other antimicrobial, or a sperm-function inhibitor as would be known to one of skill in the art.

Prevention and Treatment of Infection

The presently-disclosed subject matter further includes methods of inhibiting or treating an infection by a target pathogen in a subject, including administering to a mucosa of the subject an antibody and/or composition as disclosed herein. The mucosa can be selected from, for example, a respiratory tract mucosa (e.g., a nasal mucosa, a lung mucosa), a reproductive tract mucosa (e.g., a genital mucosa, an uterine mucosa, a vaginal mucosa), an ocular mucosa, and a gastrointestinal mucosa (e.g., an oral mucosa, an anal mucosa), and any combination thereof. In certain embodiments, the methods comprise additional steps such as one or more of isolating the antibodies, preparing a composition of the isolated antibodies, determining the level of antibodies in the mucus of the subject before administering the antibodies, and determining the level of antibodies in the mucus of the subject after administering the antibodies.

The antibodies and compositions of the present invention according to the methods described herein are administered or otherwise applied by delivering the composition, typically to a site of infection. The site of infection may be one where an infection is already present (an actual site of infection) or where an infection is likely to occur (a potential site of site of infection in or on an uninfected individual). In some embodiments, the antibodies and compositions may be topically delivered. In other embodiments, the antibodies and compositions may be systemically delivered such that the antibodies are secreted into the mucus of the subject. Accordingly, the compositions as described above may be delivered to a mucosal surface, e.g., to the reproductive tract, e.g., to the vulva, including the vaginal cavity, and/or to the gastrointestinal tract, e.g., the ano-rectal and buccal cavities and/or to the respiratory tract, e.g., the nasal cavity and the lungs. In the vaginal cavity, the compositions may be applied to any portion of the uterus, including inside the uterus and on the cervix, including the mucosa and/or lining of the endo- and ecto-cervix. The ano-rectal cavity includes the perianal surface and the lining of the anus. Topical delivery to the gastrointestinal tract includes oral administration such that the antibodies reach, e.g., the small and/or large intestines. For example, oral administration of an enteric-coated solid oral dosage form (e.g., tablet or capsule) can effectively carry the antibodies through the stomach unharmed with release occurring in the intestines.

An effective amount of the antibody can be administered. As used herein, an "effective amount" of the antibody for inhibition of infection refers to a dosage sufficient to inhibit infection by the target pathogen. As used herein, an "effective amount" of the antibody for treatment of infection refers to a dosage sufficient to inhibit spread of the target pathogen from infected cells to non-infected cells in the subject and/or to inhibit spread of the target pathogen from the infected subject to another subject, e.g., a non-infected subject. The effective amount can be an amount sufficient to trap an amount of the target pathogen in mucus. As will be recognized by one of skill in the art, the amount can vary depending on the patient and the target pathogen. The exact amount that is required will vary from subject to subject, depending on the species, age, and general condition of the subject, the particular carrier or adjuvant being used, mode of administration, and the like. As such, the effective amount will vary based on the particular circumstances, and an appropriate effective amount can be determined in a particular case by one of skill in the art using only routine experimentation. In some instances, an effective amount of the antibody that specifically binds the target pathogen or sperm can be an amount that achieves a concentration of the antibody in the mucus of about 0.1 µg/mL to about 1000 µg/mL, e.g., about 0.5 µg/mL to about 100 µg/mL, e.g., about 1 µg/mL to about 50 µg/mL or any range therein. In some embodiments, the antibody may be administered in two or more stages with different doses in each stage. For example, higher doses can be administered initially in order to clear target pathogens that are present in the mucus of exposed or infected subjects and ensure that sufficient amounts of antibody remain in the mucus to provide protection, e.g., for about 24 hours. In later stages, lower doses can be administered to maintain protective levels of the antibody. In other embodiments, protective doses can be administered to subjects that are likely to be exposed to a pathogen and higher doses can be administered if infection occurs.

As will be recognized by one of skill in the art, the term "inhibiting" or "inhibition" does not refer to the ability to completely eliminate the possibility of infection in all cases. Rather, the skilled artisan will understand that the term "inhibiting" refers to reducing the chances of pathogens moving through mucus beyond the mucus membrane such that infection of a subject can occur, such as reducing chances of infection by a pathogen when such pathogen is bound to trapping antibodies in mucus. Such decrease in infection potential can be determined relative to a control that has not been administered the antibodies of the invention. In some embodiments, the decrease of inhibition potential relative to a control can be about a 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% decrease.

In some embodiments inhibiting or treating an infection in a subject can comprise trapping a pathogen in mucus. As such, in some embodiments a method of trapping a target pathogen in mucus is provided, which method includes administering to a mucosa of the subject an antibody or composition as described herein.

In some embodiments, a method of inhibiting or treating an infection in a subject, and/or trapping a pathogen in the mucus of a subject, involves administering to a mucosa of the subject a composition comprising an isolated antibody that specifically binds a non-neutralizing epitope of a target pathogen. The antibody can be a non-neutralizing antibody. In some embodiments, the non-neutralizing antibody is provided at a concentration above a predetermined amount.

In some embodiments, a method of inhibiting or treating an infection in a subject, and/or trapping a pathogen in the mucus of a subject, involves administering to a mucosa of the subject a composition comprising an isolated antibody that specifically binds a neutralizing epitope of a target pathogen, wherein the antibody is provided at a sub-neutralization dose.

As used herein, the term "subject" refers to humans and other animals. Thus, veterinary treatment is provided in accordance with the presently-disclosed subject matter. As such, the presently-disclosed subject matter provides for the treatment of mammals such as humans, as well as those mammals of importance due to being endangered, such as Siberian tigers; of economic importance, such as animals raised on farms; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Thus, also provided is the treatment of livestock, including, but not limited to, domesticated swine, ruminants, ungulates, horses (including race horses), poultry, and the like.

A subject in need of inhibiting an infection or a disease or disorder caused by an infection is a subject that has been identified as being at risk of infection. In some embodiments, the subject is identified as having been exposed to the target pathogen. In other embodiments, the subject is in contact with other subjects that are infected or are likely to become infected, e.g., a subject that is living with, working with, and/or attending school with infected subjects.

A subject in need of treating an infection or a disease or disorder caused by an infection is a subject that has been diagnosed as infected with a pathogen or is suspected of being infected with a pathogen, e.g., exhibiting symptoms of infection.

In particular embodiments of the invention, more than one administration (e.g., two, three, four, or more administrations) of the antibody, composition, or device comprising the composition can be employed over a variety of time intervals (e.g., hourly, daily, weekly, monthly, etc.) to achieve prophylactic and/or therapeutic effects.

In some embodiments, the method include administering an antibody, and further administering an additional active agent, e.g., prophylactic or therapeutic agent, e.g., an antimicrobial, such as an antibiotic, an antiviral, or other antimicrobial as would be known to one of skill in the art. The additional active agents can be delivered concurrently with the antibodies and compositions of the invention. The additional active agents can be delivered in the same composition as the antibody or in separate compositions. As used herein, the word "concurrently" means sufficiently close in time to produce a combined effect (that is, concurrently can be simultaneously, or it can be two or more events occurring within a short time period before or after each other).

Contraception

One aspect of the invention relates to methods of contraception. One embodiment relates to a method of providing contraception, e.g., inhibiting fertilization, in a female subject, comprising administering to the mucosa of the reproductive tract, e.g., the vaginal and/or cervical mucosa, of the subject an antibody or composition of the invention in an amount effective to inhibit sperm-egg fertilization, and thus prevent pregnancy. In an additional embodiment, the method can be practiced on a male subject to trap sperm in the epydidimal mucus. In certain embodiments, the methods comprise additional steps such as one or more of isolating the antibodies, preparing a composition of the isolated antibodies, determining the level of antibodies in the mucus of the subject before administering the antibodies, and determining the level of antibodies in the mucus of the subject after administering the antibodies.

The antibodies and compositions of the present invention according to the methods described herein are administered or otherwise applied by delivering the composition, typically to the reproductive tract. In some embodiments, the antibodies and compositions may be topically delivered. In other embodiments, the antibodies and compositions may be systemically delivered such that the antibodies are secreted into the mucus of the subject. Accordingly, the compositions as described above may be delivered to a mucosal surface of the reproductive tract, e.g., to the vulva, including the vaginal cavity. In the vaginal cavity, the compositions may be applied to any portion of the uterus, including inside the uterus and on the cervix, including the mucosa and/or lining of the endo- and ecto-cervix.

An effective amount of the antibody can be administered. As used herein, an "effective amount" of the antibody for contraception refers to a dosage sufficient to inhibit sperm from contacting an egg and fertilizing it. The effective amount can be an amount sufficient to trap an amount of the sperm in mucus. As will be recognized by one of skill in the art, the amount can vary depending on the subject. The exact amount that is required will vary from subject to subject, depending on the species, age, and general condition of the subject, the particular carrier or adjuvant being used, mode of administration, and the like. As such, the effective amount will vary based on the particular circumstances, and an appropriate effective amount can be determined in a particular case by one of skill in the art using only routine experimentation. In some instances, an effective amount of antibody can be an amount that achieves a concentration of antibody in the mucus of about 0.1 μg/mL to about 1000 μg/mL, e.g., about 0.5 μg/mL to about 100 μg/mL, e.g., about 1 μg/mL to about 50 μg/mL or any range therein.

As will be recognized by one of skill in the art, the term "inhibiting" or "inhibition" does not refer to the ability to completely eliminate the possibility of fertilization in all cases. Rather, the skilled artisan will understand that the term "inhibiting" refers to reducing the chances of sperm moving through mucus beyond the mucus membrane such that fertilization of a subject can occur, such as reducing chances of fertilization by a sperm when such sperm is bound to trapping antibodies in mucus. Such decrease in fertilization potential can be determined relative to a control that has not been administered the antibodies of the invention. In some embodiments, the decrease of fertilization potential relative to a control can be about a 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% decrease.

In some embodiments providing contraception in a subject can comprise trapping sperm in mucus. As such, in some embodiments a method of trapping sperm in mucus is provided, which method includes administering to a mucosa in the reproductive tract of the subject an antibody or composition as described herein.

As used herein, the term "subject" refers to humans and other animals. Thus, veterinary treatment is provided in accordance with the presently-disclosed subject matter. As such, the presently-disclosed subject matter provides for the treatment of mammals such as humans, as well as those mammals of importance due to being endangered, such as Siberian tigers; of economic importance, such as animals raised on farms; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Thus, also provided is the treatment of livestock, including, but not limited to, domesticated swine, ruminants, ungulates, horses (including race horses), poultry, and the like.

In particular embodiments of the invention, more than one administration (e.g., two, three, four, or more administrations) of the antibody, composition, or device comprising the composition can be employed over a variety of time intervals (e.g., hourly, daily, weekly, monthly, etc.) to achieve prophylactic/contraceptive effects. In some embodiments, the antibody, composition, or device is administered regularly or constantly. In other embodiments, the antibody, composition, or device is administered on an as needed basis, e.g., prior to sexual activity and/or following sexual activity.

In some embodiments, the method include administering an antibody, and further administering an additional active agent, e.g., prophylactic or therapeutic agent, e.g., a sperm-function inhibitor and/or an antimicrobial, such as an antibiotic, an antiviral, or other antimicrobial as would be known to one of skill in the art. The additional active agents can be delivered concurrently with the antibodies and compositions of the invention. The additional active agents can be delivered in the same composition as the antibody or in separate compositions. As used herein, the word "concurrently" means sufficiently close in time to produce a combined effect (that is, concurrently can be simultaneously, or it can be two or more events occurring within a short time period before or after each other).

Monitoring Vaccine Effectiveness

Having discovered the usefulness of the antibodies of the invention in preventing and treating infection by pathogens and/or diseases or disorders caused by infection by pathogens, another aspect of the invention relates to detecting the presence of such antibodies in a subject in order to determine how well the subject is protected against possible infection. For example, a subject that has been vaccinated against a particular pathogen can be monitored for the presence and level of antibodies that have trapping potency in mucus or other body fluids, e.g., saliva. If such antibodies do not appear in the mucus or appear at non-prophylactic or non-therapeutic levels, the subject can be administered a booster vaccination and/or a different vaccine in order to generate an effective amount of antibodies. For example, subjects can be monitored to ensure a level of antibodies in mucus that at least equal to the level of antibodies observed in a subject that has been exposed previously to a pathogen.

Thus, one embodiment relates to a method of monitoring the effectiveness of a vaccination in a subject that has been vaccinated against a target pathogen, comprising determining in a mucus sample from said subject the amount of an antibody comprising an oligosaccharide at a glycosylation site, the oligosaccharide having a glycosylation pattern that enhances trapping potency of the antibody in mucus, wherein the antibody specifically binds an epitope of said target pathogen, wherein the amount of said antibody is indicative of the effectiveness of the vaccination.

The mucus to be sampled can be from the appropriate mucosal surface where the antibody is expected to be found. Samples of mucus can be obtained from a subject by methods routinely used in the art. Similarly, samples of other body fluids such as saliva can be obtained from a subject by methods routinely used in the art.

A variety of assays can be employed for detection and/or quantitation of the antibody. For example, various immunoassays can be used to detect antibodies of this invention. Such immunoassays typically involve the measurement of antigen/antibody complex formation between a protein or peptide (i.e., an antigen) and its specific antibody.

The immunoassays of the invention can be either competitive or noncompetitive and both types of assays are well-known and well-developed in the art. In competitive binding assays, antigen or antibody competes with a detectably labeled antigen or antibody for specific binding to a capture site bound to a solid surface. The concentration of labeled antigen or antibody bound to the capture agent is inversely proportional to the amount of free antigen or antibody present in the sample.

Noncompetitive assays of this invention can be, for example, sandwich assays, in which, for example, the antigen is bound between two antibodies. One of the antibodies is used as a capture agent and is bound to a solid surface. The other antibody is labeled and is used to measure or detect the resultant antigen/antibody complex by e.g., visual or instrument means. A number of combinations of antibody and labeled antibody can be used, as are well known in the art. In some embodiments, the antigen/antibody complex can be detected by other proteins capable of specifically binding human immunoglobulin constant regions, such as protein A, protein L or protein G. These proteins are normal constituents of the cell walls of streptococcal bacteria. They exhibit a strong nonimmunogenic reactivity with immunoglobulin constant regions from a variety of species. (See, e.g., Kronval et al., *J. Immunol.*, 111:1401 (1973); Akerstrom et al., *J. Immunol.*, 135:2589 (1985)).

In some embodiments, the non-competitive assays need not be sandwich assays. For instance, the antibodies or antigens in the sample can be bound directly to the solid surface. The presence of antibodies or antigens in the sample can then be detected using labeled antigen or antibody, respectively.

In some embodiments, antibodies and/or proteins can be conjugated or otherwise linked or connected (e.g., covalently or noncovalently) to a solid support (e.g., bead, plate, slide, dish, membrane or well) in accordance with known techniques. Antibodies can also be conjugated or otherwise linked or connected to detectable groups such as radiolabels (e.g., $^{35}S$, $^{125}I$, $^{32}P$, $^{13}H$, $^{14}C$, $^{131}I$), enzyme labels (e.g., horseradish peroxidase, alkaline phosphatase), gold beads, chemiluminescence labels, ligands (e.g., biotin) and/or fluorescence labels (e.g., fluorescein) in accordance with known techniques.

A variety of organic and inorganic polymers, both natural and synthetic can be used as the material for the solid surface. Nonlimiting examples of polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, nitrocellulose, and the like. Other materials that can be used include, but are not limited to, include paper, glass, ceramic, metal, metalloids, semiconductive materials, cements and the like. In addition, substances that form gels, such as proteins (e.g., gelatins), lipopolysaccharides, silicates, agarose and polyacrylamides can be used. Polymers that form several aqueous phases, such as dextrans, polyalkylene glycols or surfactants, such as phospholipids, long chain (12-24 carbon atoms) alkyl ammonium salts and the like are also suitable. Where the solid surface is porous, various pore sizes can be employed depending upon the nature of the system.

A variety of immunoassay systems can be used, including but not limited to, radio-immunoassays (RIA), enzyme-linked immunosorbent assays (ELISA) assays, enzyme immunoassays (EIA), "sandwich" assays, gel diffusion precipitation reactions, immunodiffusion assays, agglutination assays, immunofluorescence assays, fluorescence activated cell sorting (FACS) assays, immunohistochemical assays, protein A immunoassays, protein G immunoassays, protein L immunoassays, biotin/avidin assays, biotin/streptavidin assays, immunoelectrophoresis assays, precipitation/flocculation reactions, immunoblots (Western blot; dot/slot blot); immunodiffusion assays; liposome immunoassay, chemiluminescence assays, library screens, expression arrays, immunoprecipitation, competitive binding assays and immunohistochemical staining. These and other assays are described, among other places, in Hampton et al. (*Serological Methods, a Laboratory Manual*, APS Press, St Paul, Mimi (1990)) and Maddox et al. (*J. Exp. Med.* 158:1211 (1993); the entire contents of which are incorporated herein by reference for teachings directed to immunoassays).

The methods of this invention can also be carried out using a variety of solid phase systems, such as described in U.S. Pat. No. 5,879,881, as well as in a dry strip lateral flow system (e.g., a "dipstick" system), such as described, for example, in U.S. Patent Publication No. 2003/0073147, the entire contents of each of which are incorporated by reference herein.

The detection and/or quantitation of the antibody in the mucus sample can further comprise characterization of the glycosylation pattern of the antibody. Determination of the glycosylation pattern can be carried out using methods well known in the art and described herein, including glycan sequencing and separation techniques such as gel electrophoresis, fluorescence-activated sorting, and mass spectrometry.

Having described the present invention, the same will be explained in greater detail in the following examples, which are included herein for illustration purposes only, and which are not intended to be limiting to the invention.

Example 1

Materials and Methods

Culture and Purification of Fluorescent HSV-1: The HSV-1 mutant 166v (Elliott et al., *J. Virol.* 73:4110 (1999)), encoding a VP22-Green Fluorescent Protein (GFP) tegument protein packaged into HSV-1 at relatively high copy numbers (Heine et al., *J. Virol.* 14:640 (1974)), was kindly provided by Richard Courtney and used in all microscopy and ELISA studies, besides those for in vivo experiments. The addition of GFP to the VP22 protein appears to have no deleterious effects on viral replication (Elliott et al., *J. Virol.* 73:4110 (1999)), and the fluorescence of 166v was consistently more intense than that of HSV-1 mutants encoding other GFP fusion proteins. 166v was expanded at an MOI of 3 on confluent monolayers of HaCat cells maintained in DMEM (Life Technologies, Grand Island, N.Y.) supplemented with 5% FBS, 1×L-glutamine and 1× Penicillin/Streptomycin. Culture medium was collected 16-18 hr post-infection and twice centrifuged at 1000×g for 5 min to remove cell debris. The resulting supernatant was split into 30 mL aliquots and precipitated overnight with a polyethylene glycol (PEG)/salt solution. Briefly, 10 mL of 1.55 M NaCl was added to 30 mL of crude virus supernatant, followed by 10 mL of 40% PEG 8000 (Sigma, St. Louis, Mo.). After an overnight incubation at 4° C. the virus/PEG solution was centrifuged at 2555×g and 4° C. for 1 hr. The virus pellet was then resuspended in 1×PBS and centrifuged through a continuous 20-50% (w/w) sucrose in PBS gradient for 1 hr at 74,119×g. The resulting virus band was collected, diluted 1:5 in PBS, layered over 30% (w/w) sucrose in PBS, and centrifuged for 1.5 hr at 83,472×g to pellet virus for further purification. Purified virus pellet was resuspended in PBS and stored as single use aliquots at −80° C.

Cervicovaginal Mucus (CVM) Collection and Characterization: CVM collection was performed as published previously (Lai et al., *J. Virol.* 83:11196 (2009); Lai et al., *Proc. Natl. Acad. Sci. U.S.A.* 107:598 (2010)). Briefly, undiluted CVM secretions, averaging 0.3 g per sample, were obtained from women of reproductive age, ranging from 20 to 32 years old (27.4±0.9 years, mean±SEM), by using a self-sampling menstrual collection device following protocols approved by the Institutional Review Board of the University of North Carolina Chapel Hill. Informed consent of participants was obtained after the nature and possible consequences of the study were explained. Participants inserted the device into the vagina for at least 30 s, removed it, and placed it into a 50 mL centrifuge tube. Samples were centrifuged at 230×g for 2 min to collect the secretions. Aliquots of CVM for lactic acid and Ab measurements (diluted 1:5 with 1×PBS and stored at −80° C.) and slides for gram staining were prepared immediately, and the remainder of the sample was stored at 4° C. until microscopy, typically within a few hours. Samples were collected at random times throughout the menstrual cycle, and cycle phase was estimated based on the last menstrual period date normalized to a 28 day cycle. No samples were ovulatory based on visual observation (none exhibited spinnbarkeit). Samples that were non-uniform in color or consistency were discarded. Donors stated they had not used vaginal products nor participated in unprotected intercourse within 3 days prior to donating. All samples had pH<4.5; none had bacterial vaginosis (BY) based on Gram staining and Nugent scoring, following scoring criteria described previously (Nugent et al., *J. Clin. Microbiol.* 29:297 (1991)). For lactic acid and Ab measurements, CVM aliquots were thawed and centrifuged for 2 min at 21,130×g to obtain cell-free supernatant containing lactic acid and Ab. Lactic acid content was measured using a DA-lactic acid kit (R-Biopharm, Darmstadt, Germany) according to manufacturer protocol, but adapted to a 96-well format.

Total immunoglobulin levels in CVM were quantified using the Human Isotyping Kit (HGAMMAG-301K; Millipore, Billerica, Mass.) according to manufacturer protocol. Briefly, 20× stock isotyping beads were vortexed, sonicated, diluted to lX, and incubated with 50 L of serially diluted CVM supernatant at 1:2 beads:CVM volume ratio. After 1 hr, the beads were separated from CVM supernatant using a magnetic plate, and washed twice with wash buffer. The beads were then incubated with 25 L of 1× anti-Human Kappa and Lambda-PE for 1 hr, washed twice, and resuspended in Luminex Drive fluid. Fluorescence intensities indicative of immunoglobulin levels present in CVM were measured using the Luminex MAGPIX system, and data analysis was performed using Milliplex Analyst (v3.5.5.0; Vigene Tech Inc., Carlisle, Mass.). All incubations were carried out at room temperature in the dark with vigorous agitation.

Whole-virus ELISA was used to quantify HSV-1 specific IgG. Briefly, high-affinity 96-well half-area plates (Thermo Scientific, Rockford, Ill.) were coated overnight at 4° C. with 25 L per well of affinity-purified intact HSV-1 at 20 µg/mL (measured using BCA assay). The plates were washed four times with 0.05% Tween in PBS (PBS-T), blocked with 5% milk for at least 1 hr followed by PBS-T washes, then incubated for at least 1 hr with serial dilutions of CVM supernatant. Following PBS-T washes, virion-bound IgG was quantified using F(ab')$_2$ anti-human IgG Fc (Goat)-HRP conjugate (709-1317; Rockland, Gilbertsville, Pa.) and 1-Step Ultra TMB substrate (Thermo Scientific, Rockford, Ill.), and compared to a standard generated on the same plate using twice-purified anti-HSV-1 IgG, which was assumed to be >90% pure. TMB conversion was terminated with 2 N sulfuric acid, and absorbance was measured at 450 nm using a BioTek Synergy 2 plate reader. HSV-1 specific IgA and IgM levels were too low to be detected by this assay.

Preparation and Characterization of Anti-HSV-1 IgG: Anti-HSV-1 IgG was purified from intravenous immunoglobulin (IVIg, Privigen®; ≥98% IgG; CSL Behring, King of Prussia, Pa.) by affinity column purification. Briefly, HSV glycoproteins were extracted from purified HSV-1 by overnight incubation with Triton X-100 (final concentration 0.05%) at 4° C., followed by centrifugation at 21,130×g and 4° C. for 1.5 hr. The resulting supernatant containing HSV glycoproteins was coupled to AminoLink Plus Coupling Resins (Thermo Scientific, Rockford, Ill.) according to manufacturer protocol, and stored at 4° C. until use. To extract HSV-1 specific IgG, the column was first warmed to room temperature and washed twice with 3 mL of equilibrium buffer (150 mM NaCl, 0.05% Tween, 10 mM sodium phosphate at pH 6). The column was then loaded with 2 mL of IVIg buffer exchanged into equilibrium buffer using a 50 kDa MWCO concentrator (Corning, Tewksbury, Mass.), and incubated at room temperature for at least 45 min with end-over-end mixing. Unbound, non-specific Ab was removed by washing with 1 mL of equilibrium buffer followed by three additional rounds of wash buffer (4 mL each round; 500 mM NaCl, 0.05% Tween, 10 mM sodium phosphate at pH 6). Bound Ab was then eluted using IgG Elution Buffer (Thermo Scientific, Rockford, Ill.); each elution consisted of three 3 mL volumes of elution buffer, and was collected into tubes containing 100 L of 10 mM sodium phosphate pH 6 to neutralize the elutions. Elutions from multiple runs were pooled together, concentrated and buffer exchanged into PBS using a 30 kDa MWCO concentrator tube, supplemented with sodium azide (final concentration 0.03%) and stored at 4° C. until use. A single purification round removed over 99% of non-specific IgG, tested by spiking IVIg with mouse IgG. Final concentration of purified IgG was measured via sandwich ELISA, with plates coated with 2 µg/mL of anti-human IgG Fc (Alpha Diagnostics, San Antonio, Tex.) followed by detection with F(ab')$_2$ anti-human IgG Fc (Goat)-HRP, and compared to a standard curve generated with serial dilutions of stock IVIg.

Figures 3A, 3B, 3C:
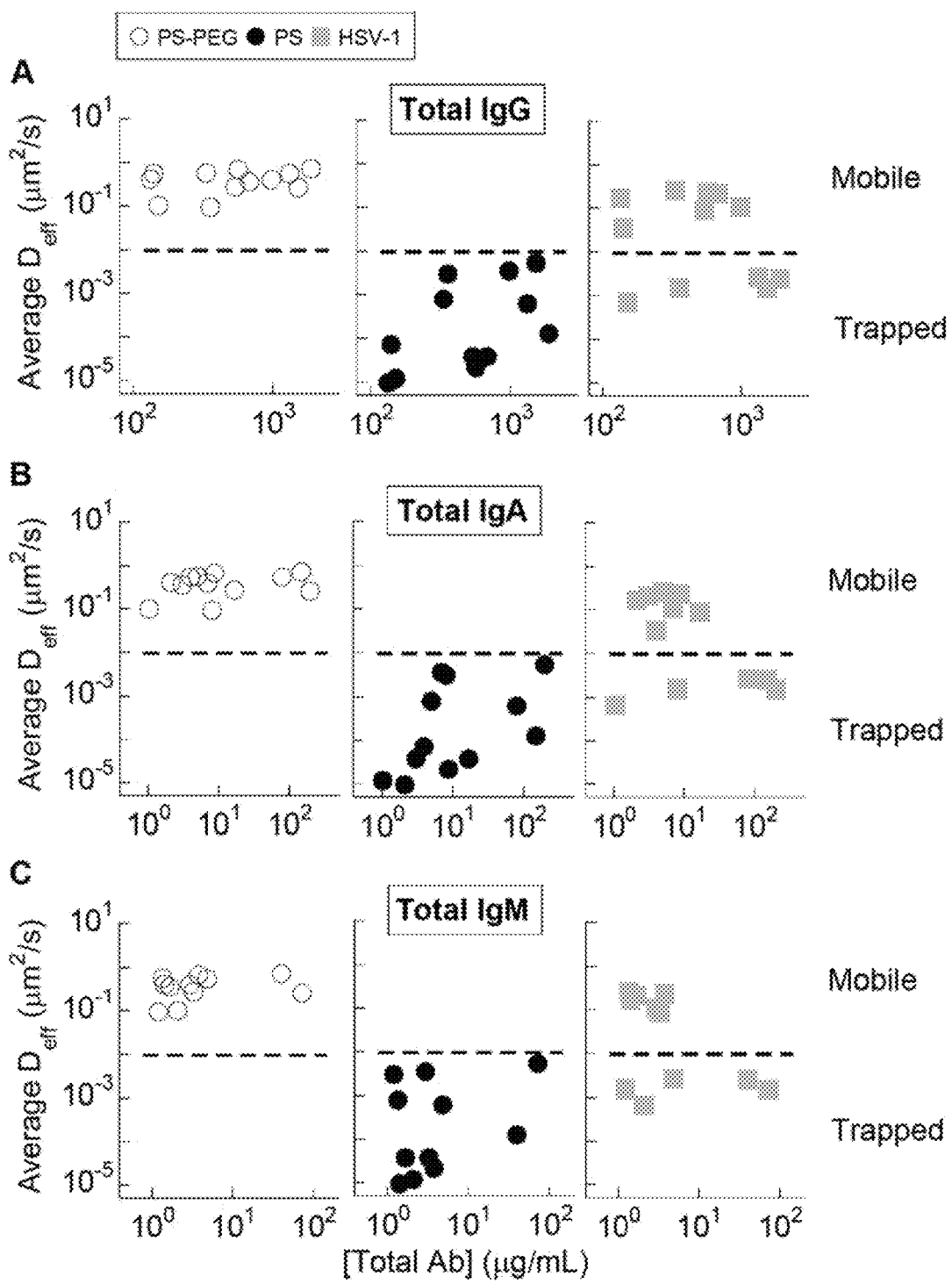
FIGS. 3A-3C show HSV-1 immobilization in CVM samples with elevated endogenous anti-HSV-1 IgG does not correlate with total IgG, IgA or IgM content. Geometric average $D_{eff}(\tau=1\text{ s})$ for PS-PEG, PS and HSV-1 in individual CVM samples from unique donors (n=12) as a function of total endogenous (A) IgG, (B) IgA or (C) IgM. Dashed lines represent the $D_{eff}$ cutoff below which particles are permanently trapped (moving less than their diameter within 1 s).

Preparation and Characterization of Anti-HSV-1 F(Ab')$_2$: HSV-1 specific IgG was fragmented using a F(ab')$_2$ Preparation Kit (Thermo Scientific, Rockford, Ill.). Briefly, IgG was desalted into IgG Digestion Buffer using 3 kDa MWCO concentrator tubes (Amicon 0.5 mL; Millipore, Billerica, Mass.) and incubated with pepsin at 37° C. for 3.5 hr with end-over-end mixing, followed by purification using a Protein A column (0.2 mL resin; Thermo Scientific, Rockford, Ill.) and PBS washes to remove undigested IgG. Fragmentation was confirmed using a non-reducing 4-12% Bis-Tris gel with MOPS running buffer. The gel was stained with Coomassie Blue for imaging; note that the gel image presented in FIG. 3 was desaturated and contrast-adjusted using Pixlr photo editor to produce a black and white image (same settings applied across entire image). A competitive inhibition ELISA was also performed to confirm that the purified F(ab')$_2$ blocked binding of intact anti-HSV-1 IgG. HSV-1 coated wells were incubated with either 1% milk or different dilutions of anti-HSV-1 F(ab')$_2$ for 1 hr, followed by incubation with intact HSV-1 specific IgG for 1 hr and quantification of bound IgG using F(ab)$_2$ anti-human IgG Fc (Goat)-HRP conjugate. Total amounts of anti-HSV-1 F(ab')$_2$ were quantified via sandwich ELISA with plates coated with HSV-1 virions as described above, but with detection by anti-human IgG F(ab')$_2$ (Goat)-HRP conjugate (Rockland 209-1304).

Preparation and Characterization of Deglycosylated Anti-HSV-1 IgG: N-linked oligosaccharides on purified anti-HSV-1 IgG were cleaved by incubating 200 g of IgG with 10 µL of PNGase and 11 µL of 10×G7 reaction buffer (New England Biolabs, Ipswich, Mass.) for at least 24 hr at 37° C. IgG was then recovered using a Protein A column, eluted with IgG Elution Buffer into 100 µL of 10 mM sodium phosphate pH 6 and buffer exchanged into PBS using a 30 kDa MWCO concentrator tube. The deglycosylated IgG was further purified using a 0.8 mL spin column immobilized with Con A-agarose slurry (Vector Labs, Burlingame, Calif.) and washed thrice with equilibrium buffer (10 mM HEPES with 0.15 M NaCl at pH 7.5) prior to incubation with end-over-end mixing for 45 min at room temperature. Following the incubation, the column was spun at 5000×g for 1 min to collect the flow through, which contains the deglycosylated IgG, and washed thrice with equilibrium buffer to maximize recovery. The flow through and the washes were pooled, buffer exchanged into PBS using a 30 kDa MWCO concentrator tube, supplemented with sodium azide (final concentration 0.03%) and stored at 4° C. until use. Total amounts of deglycosylated IgG were measured as described above. Deglycosylation was confirmed using a lectin-ELISA assay. Briefly, high-affinity 96-well plates were coated overnight at 4° C. with 50 µL per well of 1 µg/mL purified deglycosylated HSV-1 IgG. The plates were washed 4× with PBS-T, blocked with 300 µL/well of 1× Carbo Free solution (Vector Labs, Burlingame, Calif.) for at least 1 hr followed by PBS-T washes, then incubated with 50 L/well of 1 µg/mL biotinylated Con A lectin (Vector Labs, Burlingame, Calif.) for at least 2 hr. Following PBS-T washes, IgG-bound lectin was quantified using anti-biotin-HRP conjugate (Vector Labs, Burlingame, Calif.) and 1-Step Ultra TMB substrate, and compared to wells coated with affinity-purified HSV-1 IgG or IVIg. TMB conversion was terminated with 2 N sulfuric acid, and absorbance was measured at 460 nm using a BioTek Synergy 2 plate reader and normalized to the amount of IgG bound to coated wells quantified using F(ab')$_2$ anti-human IgG Fc (Goat)-HRP conjugate.

Neutralization Assay: Purified HSV-1 (~550 PFU; 5 µL) was incubated with 95 µL of HSV-1 specific IgG solution at different final concentrations for 1 hr with end-over-end mixing. The mixture was then diluted with 210 L of media, of which duplicate 150 µL aliquots were transferred to confluent Vero cell monolayers in a 6-well plate. Plates were incubated at 37° C. for 1 hr with periodic rocking to ensure that the plates did not dry out, before the HSV-1/Ab mixture was aspirated off and wells were washed with 2 mL of PBS. The plates were then incubated for 3 days at 37° C. in 2% carboxymethyl cellulose in EMEM supplemented with 1×L-glutamine and 1× Penicillin/Streptomycin, before staining with 1% crystal violet solution, and the resulting plaques were manually counted and compared to control wells to determine the extent of neutralization.

Multiple Particle Tracking of HSV-1 in CVM: To mimic neutralization of CVM by alkaline seminal fluid, we titrated CVM to pH 6.8-7.1 using small volumes (~3% v/v) of 3 N NaOH, and confirmed pH using a micro pH electrode (Microelectrodes, Inc., Bedford, N.H.) calibrated to pH 4, 7 and 10 buffers. Samples were either untreated or treated by addition of known amounts of purified anti-HSV-1 IgG or control (anti-biotin) IgG. Control beads consisted of red or green fluorescent 200 nm carboxyl-modified polystyrene particles (Molecular Probes, Eugene, Oreg.), either uncoated (PS; muco-adhesive) or covalently conjugated with low molecular weight (2 kDa), amine-functionalized polyethylene glycol (PEG; Rapp Polymere, Tuebingen, Germany) to produce coated particles (PS-PEG; muco-inert), as previously described (Lai et al., *Proc. Natl. Acad. Sci. U.S.A.* 104:1482 (2007)). Fluorescent virions or control beads (approximately $10^8$-$10^9$ particles/mL) were added at 5% v/v to 20 µL of CVM placed in a custom-made glass chamber, and incubated for 1 hr at 37° C. prior to microscopy. The translational motions of the particles were recorded using an EMCCD camera (Evolve 512; Photometrics, Tucson, Ariz.) mounted on an inverted epifluorescence microscope (AxioObserver D1; Zeiss, Thornwood, N.Y.), equipped with an Alpha Plan-Apo 100×/1.46 NA objective, environmental (temperature and CO$_2$) control chamber and an LED light source (Lumencor Light Engine DAPI/GFP/543/623/690). Videos (512×512, 16-bit image depth) were captured with MetaMorph imaging software (Molecular Devices, Sunnyvale, Calif.) at a temporal resolution of 66.7 ms and spatial resolution of 10 nm (nominal pixel resolution 0.156 m/pixel) for 20 s. The tracking resolution was determined by tracking the displacements of particles immobilized with a strong adhesive, following a previously described method (Apgar et al., *Biophys. J.* 79:1095 (2000)). Particle trajectories were analyzed using MetaMorph software as described previously (Lai et al., *Proc. Natl. Acad. Sci. U.S.A.* 104:1482 (2007); Lai et al., *J Virol.* 83:11196 (2009); Lai et al., *Proc. Natl. Acad. Sci. U.S.A.* 107:598 (2010)); image contrast was adjusted to improve particle visibility, but the same contrast level was applied throughout the entire video and did not bias toward any particle population. Sub-pixel tracking resolution is obtained by determining the precise location of the particle centroid by light-intensity-weighted averaging of neighboring pixels. Trapped particles were defined as those with effective diffusivity ($D_{eff}$)<0.01 µm$^2$/s at a time scale (t) of 1 s (i.e., particles move less than their diameter within 1 s). In a subset of experiments, it was confirmed that particles defined as trapped over the course of 20 s based on this criterion remain confined to the same locations over more than 15 min. The slope a of the log-log mean square displacement (<MSD>) vs. time scale plot provides a further measure of particle mobility: α=1 for pure unobstructed Brownian diffusion, e.g., particles in water, becomes smaller as obstruction to particle diffusion increases, and a is zero for permanently trapped particles. At least five independent experiments in CVM from different donors, with n≥100 particles per experiment, were performed for each condition. For a subset of donors, similar observations were made at least twice in samples obtained on separate days to ensure reproducibility, but only one sample was used for analysis.

Mouse Vaginal HSV-2 Challenge Model: All experiments conducted with mice were performed in accordance with protocols approved by the Johns Hopkins University Animal Care and Use Committee satisfying the requirements of the E.E.C. Guidelines (1986) and U.S. Federal Guidelines (1985). Female CF-1 mice (6-8 weeks old; Harlan, Frederick, Md.) were treated with Depo-Provera' (medroxyprogesterone acetate, 2.5 mg/mouse) by subcutaneous injection into the right flank 6-8 days prior to use, Depo-Provera® synchronizes mice in a prolonged diestrus-like state, in which the vaginal epithelium thins and susceptibility of the tissue to infection increases (Cone et al., BMC Infect. Dis. 6:90 (2006)). Depo-Provera®-treated mice were randomly divided into groups of ten. The mouse vagina is pH neutral (Meysick et al., J. Parasitol. 78:157 (1992)); therefore, no attempt was made to modify vaginal pH prior to inoculation. Inocula were prepared by mixing HSV-2 (final dose 2 $ID_{50}$; strain G, ATCC, Manassas, Va.) with medium or different concentrations of control (anti-biotin) or anti-gG IgG (8.F.141; Santa Cruz Biotechnology, Inc., Santa Cruz, Calif.), and incubating for 1 hr at 37° C. Mice were inoculated with 20 L of HSV-2 solution, delivered to the vagina using a 50 μL Wiretrol (Drummond, Broomall, Pa.), fire-polished to avoid damage to the vaginal epithelium. In some studies, the mouse vagina was gently washed with ~10 mL of normal saline delivered at 1 mL/min through a smooth ball-tipped gavage needle connected to a syringe pump, prior to HSV-2 challenge. Removal of mucus by this process was measured using a fluorimetrie mucin assay, as previously described (Crowther et al., Anal. Biochem. 163: 170 (1987)). Importantly, the gentle wash did not damage the vaginal epithelium, as confirmed by microscopy with a fluorescence-based dead cell stain (YOYO-1) that assesses membrane integrity (Cone et al., 2006), compared to conventional lavage and/or vaginal swabbing with a cotton tip, which induced significant epithelial damage. YOYO-1 has been previously used to reveal toxicity caused by detergent-based microbicides that led to increased susceptibility to HSV infection (Cone et al., BMC Infect. Dis. 6:90 (2006)). Tissue sectioning and H&E staining was performed by the Animal Histopathology lab at the University of North Carolina-Chapel Hill. Infection was assayed three days post-inoculation by detection of virus in vaginal lavages. Briefly, 50 L of medium was pipetted in and out of the vagina 20 times, diluted to 0.2 mL and placed on target cells (ELVIS® HSV Test System; Diagnostic Hybrids, Athens, Ohio); infected cells (foci) were identified one day later, following manufacturer protocol. Scores for virus shedding were assigned on a scale of 0-4 based on the approximate density of foci observed ("0": 0; "0.5": <100; "1": 100-500; "2": 500-1000; "3": 1000+; "4"; saturated). At least three independent experiments were performed for each condition, with n=10 animals per experimental group (n≥30 total).

Statistical Analysis: correlation between endogenous anti-HSV-1 IgG levels and average particle or virus $D_{\it{eff}}$ in individual CVM samples was measured using Pearson's correlation coefficient (r). Statistical comparisons were limited to two groups (test group compared with the appropriate control group performed during the same experiment). Fisher's exact test was used to determine the statistical significance of reductions in % mice infected. A two-tailed Student's t-test (paired for comparisons of Ab-treated vs, native CVM for the same CVM samples) was used for all other comparisons. Differences were deemed significant at an alpha level of 0.05. All values are reported as mean±SEM unless otherwise indicated.

Example 2

Trapping of HSV in Cervicovaginal Mucus

The hypothesis of trapping-in-mucus was explored using HSV-1 (d¯180 nm), a highly prevalent sexually transmitted virus. Fresh, undiluted CVM was obtained predominantly from donors with normal *lactobacillus*-dominated vaginal microbiota, as confirmed by Nugent scoring (Table 1). HSV-1 virions expressing a VP22-GFP tegument protein construct, packaged at high copy numbers while maintaining native viral envelope integrity, were mixed into CVM pH-neutralized to mimic neutralization by alkaline seminal fluid. Time-lapse microscopy of virion motions in real-time was then performed with high spatiotemporal resolution, and virion mobility was quantified using multiple particle tracking over a long time scale. Substantial differences in HSV-1 mobility were observed in CVM samples from different donors (FIG. 1A) in 7 of 12 CVM samples, most virions diffused distances spanning several microns over the course of 20 s, whereas in the remaining 5 CVM samples, the majority of virions were essentially trapped, moving less than their diameter (<200 nm) in 20 s.

TABLE 1

Characterization of CVM samples: menstrual cycle phase, Nugent score and % lactic acid.

| Donor ID | Cycle day[1] | Cycle phase[3] | Nugent score[4] | % Lactic acid[5] |
|---|---|---|---|---|
| F10 | 17 | Luteal | 1 | 2.4 ± 0.039 |
| F12 | 25 | Luteal | 2 | 0.81 ± 0.081 |
| F14 | 26 | Luteal | 2 | 0.95 ± 0.10 |
| F18 | 11 | Follicular | 4 | 0.56 ± 0.022 |
| F9 | N/A[2] | N/A | 0 | 0.93 ± 0.062 |
| F13 | 9 | Follicular | 0 | 1.1 ± 0.031 |
| F15 | 25 | Luteal | 0 | 1.1 ± 0.042 |
| F17 | N/A | N/A | 1 | 1.2 ± 0.088 |
| F2 | 15 | Luteal | 2 | 0.74 ± 0.073 |
| F21 | N/A | N/A | 0 | 1.5 ± 0.081 |
| F5 | 10 | Follicular | 0 | 1.4 ± 0.074 |
| F8 | 19 | Luteal | 0 | 1.9 ± 0.15 |
| Median | | | 0.5 | 1.10 |
| SEM | | | 0.37 | 0.15 |

[1]Cycle day calculated as the number of days from the first day of the last menstrual period normalized by the cycle length to a 28 day cycle.
[2]N/A = hormonal contraceptive.
[3]Cycle phase estimated based on normalized cycle day; no samples were ovulatory based on absence of spinnbarkeit by visual inspection.
[4]A Nugent score of 0-3 corresponds to "normal" (lactobacilli-dominated) microflora, 4-6 to "intermediate", and 7-10 to "bacterial vaginosis" (BV)-a condition associated with greater risk of STI acquisition. Assessment of Nugent scores was independently confirmed by the Clinical Microbiology and Immunology Lab at UNC.
[5]Values are expressed as a mean ± SEM.
Grey highlight indicates CVM samples containing sufficient native levels of anti-HSV-1 IgG to immobilize virions.

Figures 6A, 6B:
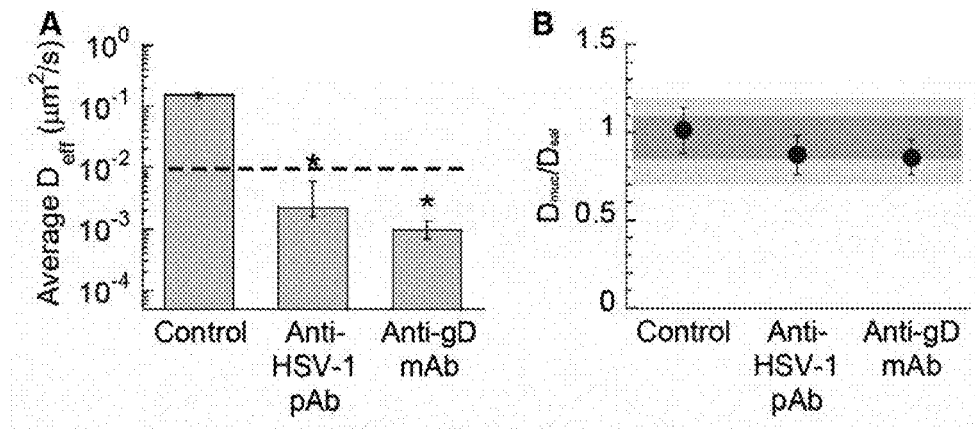
FIGS. 6A-6B show trapping HSV virions with polyclonal anti-HSV-1 and monoclonal anti-gD human IgG based on weak IgG-mucus interactions. (A) HSV-1 mobility in native CVM samples with low endogenous anti-HSV-1 IgG treated with 1 µg/mL polyclonal anti-HSV-1 IgG ("Anti-HSV-1 pAb"), monoclonal anti-gD IgG produced in 293 cells ("Anti-gD mAb") or anti-biotin monoclonal IgG produced in 293 cells ("Control"). Dashed line represents the $D_{eff}$ cutoff below which particles are permanently trapped (moving less than their diameter within 1 s). * indicates statistically significant difference compared to the Control group (p<0.01); the difference between the Anti-HSV-1 pAb and Anti-gD mAb groups was not statistically significant. (B) Ratio of diffusion coefficients in CVM vs. saline ($D_{muc}/D_{sal}$) for different Ab measured by fluorescence recovery after photobleaching (FRAP). For comparison, FITC-labeled human IgG ("Control") is included. Shaded regions indicate the range of values (dark grey=averages and light grey=average±standard deviation, respectively).

Since IgG is the predominant immunoglobulin in human CVM (Usala et al., J. Reprod. Med. 34:292 (1989)), it was examined whether virion mobility correlated with endogenous virus-specific IgG in all 12 CVM samples using a whole-virus ELISA assay (Table 2). In good agreement with the hypothesis, HSV-1 diffused rapidly through all CVM samples that had little or no detectable endogenous anti-HSV-1 IgG (<0.2 μg/mL; detection limit 0.017 μg/mL) at rates only several-fold lower than their expected rates in water (FIGS. 1 and 2A). In contrast, in samples with elevated levels of endogenous anti-HSV-1 IgG (≥0.6 g/mL), most HSV-1 virions were effectively trapped. HSV-1 that was trapped in place over the first 20 s observation remained trapped in the same locations for at least 15 min (FIG. 2B). In the same CVM samples, control latex nanoparticles comparable in size to HSV-1 and engineered with muco-inert coatings (PS-PEG; d~200 nm) exhibited rapid diffusion (FIGS. 1 and 2A), in good agreement with previous observations of the large pores present in human CVM (average ~340 nm) ((Lai et al., *Proc. Natl. Acad. Sci. U.S.A.* 104:1482 (2007); Lai et al., *Proc. Natl. Acad. Sci. U.S.A.* 107:598 (2010)). Thus, the mucus mesh spacing was large enough for IgG-coated HSV-1 (at most 15-20 nm larger diameter even at saturation) to diffuse relatively unimpeded in the absence of adhesive interactions with mucin gel. Muco-adhesive latex nanoparticles of the same size (PS; d~200 nm) were markedly slowed or immobilized in the same CVM secretions (FIGS. 1 and 2A). Importantly, observations with PS-PEG and PS control particles confirmed that the general barrier properties of all samples, including those with low levels of endogenous anti-HSV-1 IgG, remained intact. HSV-1 mobility correlated only with endogenous HSV-1 specific IgG, and did not correlate with total IgG, IgA or IgM content (FIG. 3), After removal of ~90-95% of total IgG from these samples by dialysis at constant sample volume, HSV-1 became readily mobile (FIG. 4A), whereas PS beads remained immobilized (FIG. 4A).

component in mucus that might be associated with elevated endogenous anti-HSV-1 IgG, HSV-1 specific IgG was affinity-purified from human intravenous immunoglobulin (starting with a pure clinical IgG preparation), and the purified IgG was mixed into CVM samples that had low endogenous anti-HSV-1 IgG. It was found that addition of 1 μg/mL anti-HSV-1 IgG trapped HSV-1 with a potency comparable to that of endogenous anti-HSV-1 IgG (FIGS. 5A-5C; $p<0.05$ compared to native specimen without addition of anti-HSV-1 IgG). Lower anti-HSV-1 IgG doses were tested, and potent trapping of virions was observed when ~333 ng/mL anti-HSV-1 IgG was added ($p<0.05$), and partial trapping at 100 and 33 ng/mL anti-HSV-1 IgG added (both $p<0.05$). As controls, muco-adhesive PS remained markedly slowed or immobilized and muco-inert PS-PEG freely diffusive in CVM samples treated with the highest anti-HSV-1 IgG doses (FIG. 4B), confirming that the IgG did not cause HSV-1 trapping by altering mucus viscoelasticity or mesh spacing. Affinity-purified anti-HSV-1 IgG exhibited little neutralizing activity at 1 g/mL and ~333 ng/mL (FIG. 5B), based on reduction of plaque formation in Vero cells, suggesting that multiple low-affinity bonds between IgG and CVM can trap virions at IgG levels lower than those needed to neutralize. HSV-1 was also trapped by a humanized monoclonal anti-gD IgG in CVM (FIG. 6A) but not by control, non-specific IgG (FIG. 6A), underscoring the specificity of trapping via particular antibody-virus pairs, rather than a non-specific interaction or alteration of general mucus

TABLE 2

Characterization of CVM samples: Ab content. Anti-HSV-1 IgG

| Donor ID | Average | % of total | $IgG_1$ | $IgG_2$ | $IgG_3$ | $IgG_4$ | Total IgG | Total IgA | Total IgM |
|---|---|---|---|---|---|---|---|---|---|
| F10 | 0.92 ± 0.20 | 0.60% | 90% | 6.7% | 3.4% | N.D.[2] | 150 ± 12 | 1.0 ± 0.22 | 2.1 ± 1.7 |
| F12 | 0.66 ± 0.037 | 0.19% | 65% | 28% | 8.1% | 0.66% | 360 ± 36 | 8.1 ± 1.1 | 1.2 ± 0.91 |
| F14 | 1.9 ± 0.20 | 0.14% | 78% | 19% | 4.2% | 1.0% | 1300 ± 130 | 79 ± 9.3 | 4.8 ± 0.11 |
| F18 | 8.5 ± 0.31 | 0.56% | 71% | 20% | 6.1% | 4.5% | 1500 ± 110 | 200 ± 15 | 72 ± 6.9 |
| F9 | 23 ± 1.4 | 1.2% | 83% | 11% | 4.0% | 1.5% | 1900 ± 250 | 150 ± 21 | 39 ± 5.5 |
| Median | 1.9 | 0.56% | 78% | 19% | 4.2% | 1.0% | 1300 | 79 | 4.8 |
| SEM | 4.3 | 0.19% | 4.3% | 3.7% | 0.88% | 0.77% | 340 | 38 | 14 |
| F13 | 0.026 ± 0.00049 | 0.027% | 76% | 18% | 5.7% | 0.28% | 980 ± 79 | 7.0 ± 0.45 | 2.9 ± 1.3 |
| F15 | 0.080 ± 0.0011 | 0.024% | 68% | 29% | 4.1% | 0.28% | 330 ± 43 | 5.0 ± 0.91 | 1.4 ± 0.92 |
| F17 | 0.19 ± 0.023 | 0.036% | 49% | 34% | 20% | 0.67% | 540 ± 33 | 17 ± 1.5 | 3.3 ± 0.59 |
| F2 | 0.025 ± 0.0055 | 0.0044% | 67% | 27% | 9.2% | 0.0044% | 560 ± 40 | 8.9 ± 0.48 | 3.8 ± 0.44 |
| F21 | 0.018 ± 0.0063 | 0.013% | 70% | 27% | 4.0% | 0.056% | 140 ± 7.6 | 4.0 ± 0.16 | 0.085 ± 0.037 |
| F5 | 0.070 ± 0.011 | 0.010% | 91% | 6.4% | 1.9% | 0.41% | 680 ± 49 | 3.0 ± 0.31 | 1.7 ± 1.2 |
| F8 | 0.048 ± 0.030 | 0.036% | 67% | 28% | 5.0% | 0.021% | 130 ± 9.8 | 2.1 ± 0.20 | 1.4 ± 1.2 |
| Median | 0.048 | 0.013% | 68% | 27% | 5.0% | 0.28% | 540 | 5.0 | 1.7 |
| SEM | 0.023 | 0.0053% | 4.7% | 3.4% | 2.3% | 0.092% | 110 | 1.9 | 0.49 |

A well-recognized mechanism of mucosal immune defense is 'immune exclusion' in which microorganisms in the gut are agglutinated by secreted polyvalent IgA and IgM into clusters too large to diffuse through mucus (Hamburger et al., *Curr. Top. Microbiol. Immunol.* 308:173 (2006); Mantis et al., *Mucosal Immunol.* 4:603 (2011)). However, little to no agglutinated HSV-1 was in these experiments, consistent with previous findings that IgG is a relatively poor agglutinator (Berzofsky et al., In Fundamental Immunology. W. E. Paul, editor The Raven Press, New York, N.Y. 421 (1993)). Together, these observations suggest that individual HSV-1 virions in samples with elevated endogenous levels of anti-HSV-1 IgG are slowed or trapped by multiple low-affinity bonds with CVM rather than by physical (steric) obstruction.

To confirm that trapping of HSV-1 in CVM was mediated specifically by IgG bound to virions and not by any other barrier properties. In good agreement with previous studies (Olmsted et al., *Biophys. J.* 81:1930 (2001); Saltzman et al., *Biophys. J.* 66:508 (1994)), both polyclonal anti-HSV-1 IgG and monoclonal anti-gD IgG were only slightly slowed in CVM compared to saline (FIG. 6B), suggesting both antibodies form only transient, low-affinity bonds with CVM as individual molecules, yet facilitate effective trapping of virions once they accumulate on the viral surface by forming low-affinity but polyvalent IgG-mucin bonds.

Figures 7A, 7B, 7C:
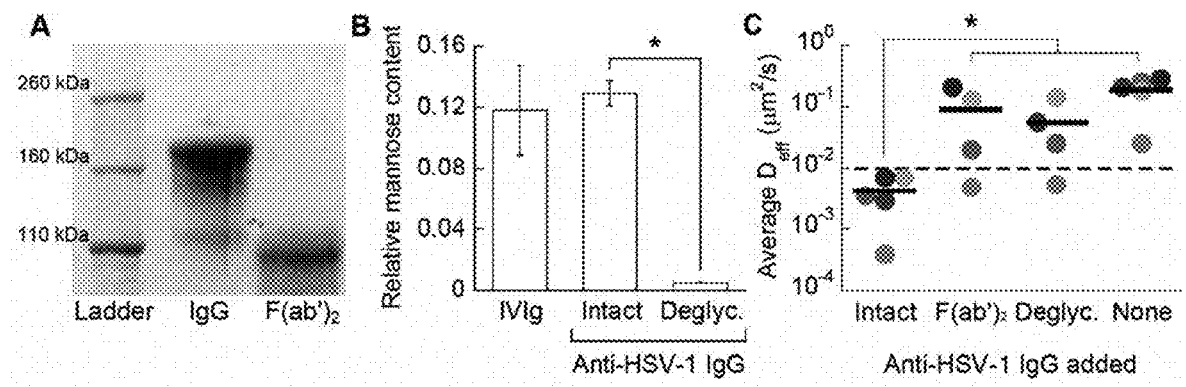
FIGS. 7A-7C show IgG-mucus interaction is Fc- and glycosylation-dependent. (A) Preparation of anti-HSV-1 F(ab')$_2$ confirmed by SDS-PAGE, (B) Preparation of deglycosylated anti-HSV-1 IgG confirmed by lectin-binding assay (absorbance of IgG-bound ConA normalized to amount of IgG). Error bars represent SEM. (C) Mobility (D$_{eff}$; τ=1 s) of HSV-1 in CVM with low endogenous anti-HSV-1 IgG incubated with various HSV-1 specific Ab: 1 µg/mL affinity-purified native IgG ("Intact"), 667 ng/mL F(ab')$_2$, and 1 deglycosylated IgG compared to HSV-1 in native CVM ("None"). Distinct samples (n=4-5, each experiment performed independently) are indicated with different color circles; averages are indicated by solid lines. Dashed line represents the D$_{eff}$ cutoff below which particles are permanently trapped (moving less than their diameter within 1 s). * indicates statistically significant difference (p<0.05).

It was next sought to determine the biochemical basis of the low-affinity bonds between IgG and CVM, The Fc domain of all IgGs harbors a conserved N-glycosylation site at Asn297, and many IgG effector functions are Fc- and Asn297 glycan-dependent (Ha et al., *Glycobiology* 21:1087 (2011)). Thus, F(ab')$_2$ fragments (FIG. 7A) and deglycosylated IgG (FIG. 7B) were prepared from the same affinity-purified anti-HSV-1 IgG to minimize any changes in HSV-1 binding avidity (confirmed by ELISA), and the mobility of HSV-1 premixed with these modified analogs prior to addition to CVM (premixed to minimize interference by endogenous HSV-1 specific IgG) was measured. It was found that both F(ab')$_2$ and deglycosylated IgG exhibited substantially reduced trapping potency compared to intact IgG (FIG. 7C; p<0.05), suggesting that the low-affinity bonds IgG forms with mucins are not only Fc-dependent, but also influenced by Fc glycosylation.

Figures 8A, 8B, 8C:
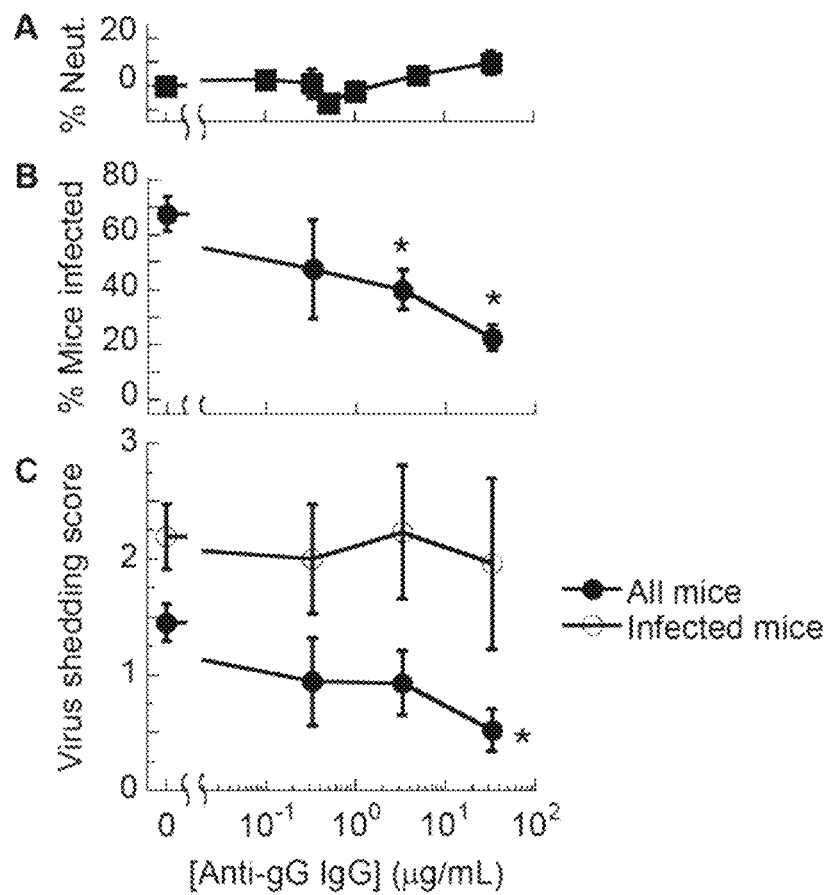
FIGS. 8A-8C show a non-neutralizing monoclonal IgG$_1$ against the gG epitope protects against vaginal HSV-2 infection in mice, without decreasing the extent of infection in mice that became infected. (A) In vitro neutralization of (% Neut.) vs. (B) in vivo protection against HSV-2. Neutralization was assayed based on reduction of HSV plaque formation in Vero cells. Depo-Provera®-treated mice were inoculated with HSV-2 mixed with control or anti-gG IgG. Infection was assayed three days post-inoculation by detection of virus in vaginal lavages using the ELVIS® HSV Test System. (C) Degree of HSV-2 shedding detected in vaginal lavages of all mice (filled circles), or of infected mice only (open circles). In vivo protection by 33 µg/mL anti-gG IgG is lost when mouse CVM is removed by gentle washing using a syringe pump. Data represent four independent experiments, each with n=10 mice per group. Error bars represent SEM. * indicates statistically significant difference compared to control (p<0.05).

To determine whether trapping viruses in mucus can protect against infection in vivo, the ability of a non-neutralizing monoclonal IgG$_1$ to reduce HSV-2 transmission in the pH neutral mouse vagina was evaluated. This monoclonal IgG$_1$ binds to the relatively sparse gG surface glycoprotein, and exhibited no neutralization activity across all concentrations tested in vitro (FIG. 8A); mouse IgG$_1$ also possesses little to no complement (Ey et al., Mol. Immunol. 17:699 (1980); Michaelsen et al., Scand. J. Immunol. 59:34 (2004); Neuberger et al., Eur. J. Immunol, 11:1012 (1981)) and ADCC (Akiyama et al., Cancer Res. 44:5127 (1984); Kipps et al., J Exp. Med. 161:1 (1985)) activity. Mice were challenged vaginally with 2 ID$_{50}$ HSV-2 with and without anti-gG IgG$_1$, and HSV infection was assayed by detection of virus shedding in vaginal lavages three days post inoculation, a more sensitive assay of infection than visual observation of lesions, viral isolation from sacral ganglia, or death (Zeitlin et al., Contraception 56:329 (1997)). Anti-gG IgG$_1$, at a concentration of 3.3 µg/mL and above, significantly protected against infection and reduced the average viral load compared to either medium alone or control, non-specific IgG (FIGS. 8B and 8C, p<0.05). Interestingly, anti-gG IgG$_1$ appeared to only reduce the rate of successful vaginal HSV transmission; in mice that became infected, the extent of vaginal infection was comparable to that in mice receiving control IgG, suggesting that the anti-gG IgG dosed did not elicit effector functions that reduced the extent of virus spread in infected mice compared to control IgG (FIG. 8C), Protection was also evaluated in mice that received a gentle vaginal wash to remove mucus without detectable trauma to the epithelium (FIG. 9A). The removal of CVM increased susceptibility to HSV-2 in control mice from ~70% to ~100% (FIG. 9B) but not the degree of HSV shedding in mice that became infected (FIG. 9C). This moderate (~30%) increase in susceptibility is likely attributed to loss of innate protection by CVM itself: a CVM layer prevents immediate direct contact between viruses and the epithelium, and contains factors, such as defensins, that may further contribute to overall reduction infectious HSV flux to the epithelium. More importantly, removal of CVM completely abolished the ~50% extra protection (from ~0% to ~20% infection) afforded by anti-gG IgG$_1$ in native mice that cannot be attributed to innate immunity (FIG. 9B). Consistent with the hypothesis that trapping in mucus may facilitate protection, these results together suggest much of the observed synergistic enhancement in protection by anti-gG IgG$_1$ when CVM is present most likely occurred prior to HSV reaching target cells, rather than by immune mechanisms that can facilitate protection at the cellular level (e.g., complement or ADCC). These observations are also consistent with the poor complement and ADCC activity of mouse IgG$_1$, as well as numerous previous studies that have shown HSV can evade complement and other classical immune protective mechanisms (Brockman et al., Vaccine 26 Suppl 8:194 (2008); Hook et al., J. Virol. 80:4038 (2008); Lubinski et al., J. Exp. Med. 190:1637 (1999); Yuan et al., Nature Immunol. 7:835 (2006)). Since even a non-neutralizing monoclonal IgG against a relatively sparse surface antigen can afford substantial protection, monoclonals against more abundant surface antigens, such as gD and gB, or those optimized to maximize interactions with mucus are likely to provide even more potent protection at mucosal surfaces in vivo.

The first evidence of antibody-mucin affinity can be traced back more than 30 years, when Kremer and Jager noted that infertility in humans is often caused by anti-sperm antibodies (Jager et al., Fertil. Steril. 36:792 (1981); Kremer et al., Fertil. Steril. 27:335 (1976)). In cervical mucus samples with high levels of anti-sperm Ab, they found that both individual and agglutinated sperm make no forward progress and shake in place for hours until they die, despite vigorous flagellar motility. More recently, Phalipon et al. suggested secretory IgA can aggregate pathogenic Shigella flexneri in mouse nasal mucus secretions via the secretory component, anchoring the bacteria to the mucus gel and thereby 'excluding' them from infectious entry (Phalipon et al., Immunity 17:107 (2002)).

In both of the above instances, the authors assumed that the antibodies were attached firmly to the mucins. Similarly, the mucin-like Fcy binding protein (FcγBP) has been proposed to serve an immunological role in mucus through its ability to bind strongly to IgG Fc (Kobayashi et at, Gut 51:169 (2002)). Nevertheless, more recent evidence indicates the primary function of FcγBP is instead to stabilize gastrointestinal mucus gel by covalently cross-linking Muc2 mucins (Johansson et at, Proc. Natl. Acad. Set. U.S.A. 108 Suppl 1:4659 (2011); Johansson et at, J. Proteome Res. 8:3549 (2009)). An IgG Fc-FcγBP-mucin crosslinking mechanism also directly contradicts numerous prior efforts that have failed to detect any significant binding of individual Ab to mucins (Clamp, Biochem. Soc. Trans. 5:1579 (1977); Cone, In Handbook of Mucosal Immunology. P. L. Ogra et al., editors. Academic Press, San Diego, Calif. 43-64 (1999); Crowther et al., Fed. Proc. 44:691 (1985); Olmsted et al., Biophys. J. 81:1930 (2001); Saltzman et al., Biophys. J. 66:508 (1994)). Indeed, previous FRAP experiments (Olmsted et al., Biophys. J. 81:1930 (2001)) and those here demonstrate that IgG and other Ab diffuse rapidly in human genital mucus, slowed only slightly compared to their diffusion in water. This can only be explained by weak and short-lived adhesive interactions between IgG and the mucin mesh, and not by the strong binding of IgG by FcγBP (Kobayashi et al., J. Immunol. 143:2567 (1989)). FcγBP also binds broadly to all IgG, and the interaction is thus subject to competitive inhibition (Kobayashi et at, J. Immunol. 143:2567 (1989)). In the present experiments where exogenous HSV-1 specific IgG was added to CVM, total levels of IgG already present in the samples were hundreds- to thousands-fold higher than the HSV-1 specific IgG doses added. Thus, for FcγBP to be responsible for the observed trapping phenomena, FcγBP must have been present in greater molar quantities than native IgG, which is unlikely given that the protein has not been routinely identified in proteomic screens of human genital tract fluid (see (Andersch-Bjorkman et al., Mol. Cell. Proteomics 6:708 (2007)) vs. (Dasari et al., J. Proteome Res. 6:1258 (2007); Shaw et al., J. Proteome Res. 6:2859 (2007); Tang et at, J. Proteome Res. 6:2874 (2007)). In contrast to previous studies, by examining the effect of IgG on virions in mucus gel rather than probing directly for interactions between individual IgG molecules and mucins, the present results document not only the potent trapping of individual virions by multiple surface-bound IgG, but also that the IgG-mucin interactions are Fc- and glycan-dependent.

Trapping virions in genital tract mucus should markedly reduce heterosexual transmission of viral infections. Women acquire many of the major sexually transmitted viral infections (e.g., HIV, HPV, and HSV) at rates on the order of 1 per 100 to 1,000 sex acts on average. This suggests few if any of these virions are able to infect target cells per intercourse, and therefore any reduction in the flux of virions that reach target cells should proportionally reduce transmission rates. Blocking initial infection altogether, rather than attempting to clear initial infections, may be especially critical for infections that are difficult, if not impossible, to cure once established (e.g., HSV, HIV). In the recent gD2-AS04 HSV vaccine trial (Belshe et al., *New Engl J. Med.* 366:34 (2012)), protective efficacy was initially observed in seronegative women but not in men or seropositive women, and a larger study of seronegative women revealed only moderate efficacy against HSV-1 (~35% efficacy against HSV-1 infection and 58% efficacy against HSV-1 genital disease) but interestingly no protection against HSV-2. In both studies, the vaccine elicited neutralizing serum Ab against HSV as well as HSV-specific cellular immune responses in all women and men. However, because mucosal levels of Ab were not monitored, it remains unclear whether what little protection was observed could have correlated with mucosal Ab response. It is likely that generating sufficient mucosal Ab levels remains a major bottleneck to an effective HSV vaccine. Inducing secreted Ab that bind to 'non-neutralizing' surface epitopes should trap pathogens as effectively as those that bind to neutralizing epitopes, a prospect that may broaden potential antigen targets for vaccine development, especially against virions with rapidly evolving neutralizing epitopes.

Example 3

Trapping of *Salmonella typhimurium* in Gastrointestinal Mucus

Figures 10A, 10B:
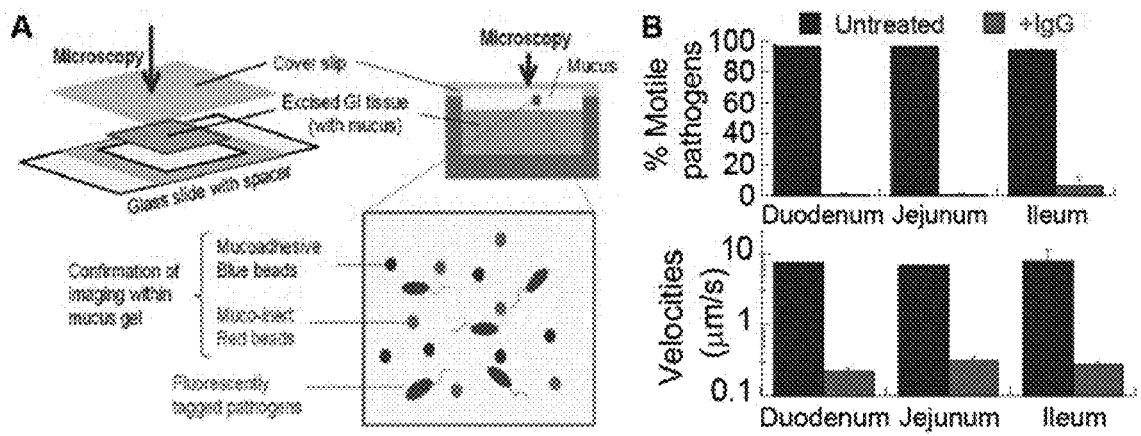
Figures 11A, 11B:
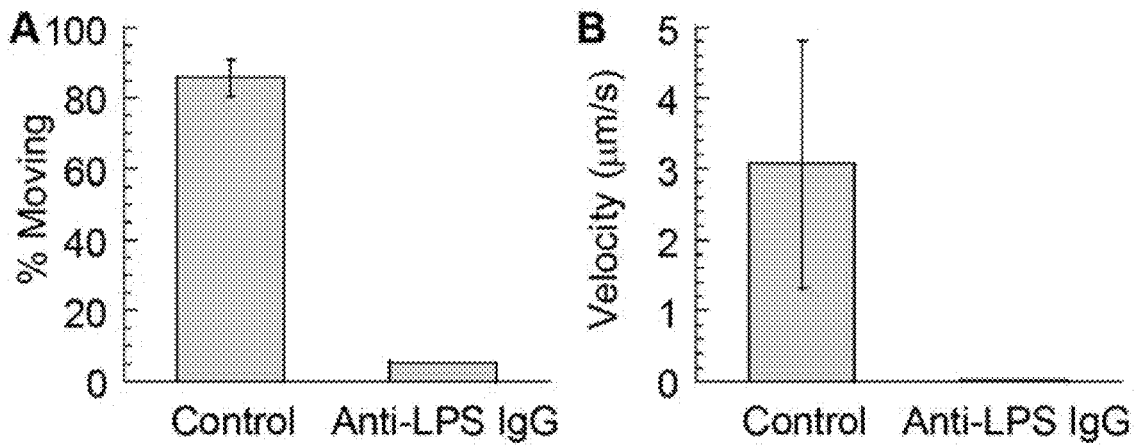
FIGS. 11A-11B show mobility of individual Salmonella typhimurium bacteria in control or anti-LPS monoclonal IgG-treated mouse gastrointestinal mucus. (A) Fraction moving and (B) average velocity. Note that average velocity for the anti-LPS IgG group is 0.036 µm/s, 85-fold lower than the average velocity for the control group.

Fc-mediated trapping of pathogens in mucus, which directly blocks infections at the portals of entry, may represent an exceptionally potent mechanism by which the immune system can rapidly adapt and reinforce multiple mucosal surfaces against diverse and rapidly evolving pathogens. A microscopy setup was developed that enables measuring bacterial mobility in real time directly in mucus overlaying intestinal epithelial tissue excised from mice (FIG. 10A). It was found that *Salmonella typhimurium* can readily penetrate undiluted mucus secretions coating the mouse gastrointestinal tract (duodenum, jejunum and ileum), but was effectively immobilized by topically applied anti-LPS and anti-flagella IgG (FIG. 10B). This immobilization occurred without inhibiting the flagella beating apparatus (Ab-coated *Salmonella* remained highly mobile in buffer) and without causing aggregation (i.e., independent of the classical, aggregation-based mechanism of immune exclusion (FIGS. 11A-11B). Furthermore, deglycosylated anti-LPS antibodies failed to trap the *Salmonella*, again highlighting the dependence of IgG-mucin interactions on Fc-N-glycans. These studies highlight the ability for IgG-mucin interactions to function at different mucosal surfaces, and act effectively on not just viral pathogens but also bacterial pathogens. The observed trapping in both CVM (predominantly Muc5b mucins) and gastrointestinal mucus (Muc2 mucins) suggests the molecular basis for Fc-mucin affinity is likely common among major secreted mucins—the long densely glycosylated fibers that form mucus gels—and possibly mediated by glycans, since sugars represent the major constituent of mucins (up to 80% by dry weight (Lai et al., *Adv. Drug Deliv. Rev.* 61:158 (2009))).

Example 4

Role of N-Glycans on IgG-Mucin Interactions

To further evaluate the role of N-glycans on IgG-mucin interactions, a number of anti-gD antibodies ("HSV8") with distinct glycosylation patterns were tested in the CVM assay of Example 1. Antibodies with distinct glycosylation profiles were produced in *Nicotiana benthamiana* plants using a viral-based transient expression system (magnICON). Transgenic *Nicotiana benthamiana*, in which plant-specific N-glycans (with core α1,3 fucose and β1,2 xylose) are reduced by RNAi inhibition of plant-specific glycosyltransferases and specific glycosyltransferases were over-expressed (e.g., β1,4 galactosyltransferase, see www.jbc.org/content/284/31/20479.full), were used as the host plant. Extract was clarified and IgG purified by protein A chromatography. Antibodies that were tested include HSV8-GnGn, in which contains about 95% of the antibodies contain the core structure with GlcNAc, mannose and terminal GlcNAc; HSV8-Gal, in which about 63% of the antibodies have either one or two terminal galactose sugar residues and about 5% have the GnGn core structure; HSV8-Agly, which is free of any glycosylation; and HSV8 produced in 293 cell cultures, which have the general diversity in glycosylation profiles found in humans. Note that HSV8-Gal represents the major serum IgG glycoform. We found that surprisingly, HSV8-Gal were substantially less potent at trapping viruses as HSV8-GnGn, which suggests antibodies that are engineered to have greater amount/extent of GnGn glycosylation vs. the naturally found Gal-terminated glycosylation is expected to be more potent at trapping virions. This observation not only further confirms the dependence on glycosylation, but underscores the importance of the precise nature of the glycosylation pattern.

Figure 13:
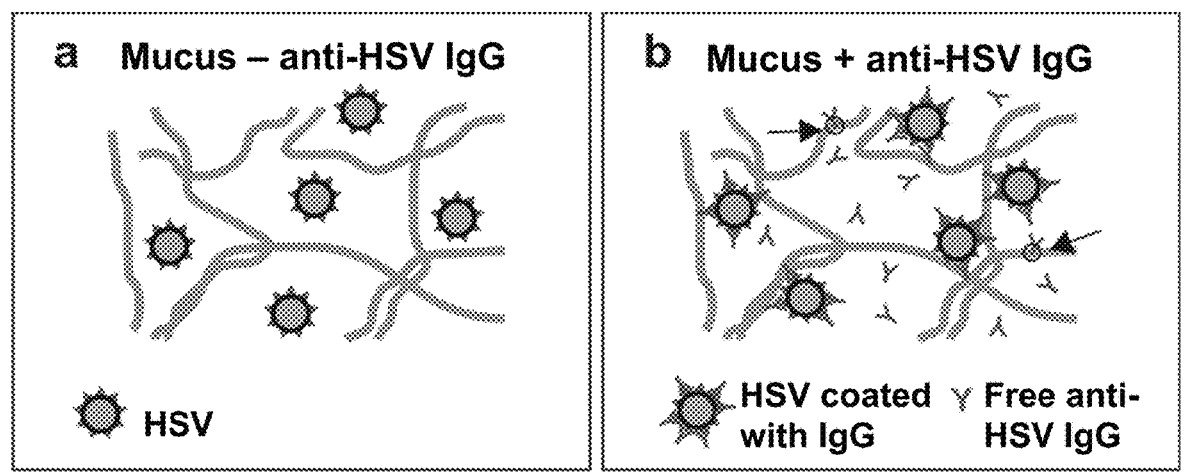
FIG. 13 shows the proposed mechanism of Ab-mediated trapping of viruses in mucus. Schematic showing (panel a) HSV readily penetrates native CVM with little to no endogenous anti-HSV IgG, and (panel b) anti-HSV IgG traps HSV in CVM by multiple transient, low affinity bonds with mucins. By forming only short-lived, low-affinity bonds with mucus, free Ab, such as IgG, are able to diffuse rapidly through mucus and binds to viruses. As IgG molecules accumulate on the virus surface, they form multiple low-affinity bonds between the virus and mucus gel. A sufficient number of these transient low-affinity bonds ensure viruses are effectively trapped in mucus at any given time, thereby reducing the flux of infectious virions that can reach target cells. Arrows indicate the small fraction of free (not virus-bound) IgG (~10-20%) that will interact with mucins at any moment in time.

As discussed above, the present invention is also based, in part, on the discovery and characterization of weak binding interactions between antibodies and mucins and the ability of such antibodies to stop the penetration of virions through mucus layers of the respiratory tract, as generally illustrated in FIG. 13. The antibody-mucin interaction can be used advantageously in methods for preventing and treating respiratory infection an entry of virions into a subject.

As mentioned above, the presently-disclosed subject matter includes antibodies, compositions, and methods for inhibiting and/or treating viral infection, and/or eliminating virions from a mucosal surface of the respiratory tract. In particular, the presently-disclosed subject matter relates to antibodies and compositions capable of trapping virions in mucus, thereby inhibiting transport of virions across or through mucus secretions.

One aspect of the invention relates to an antibody, e.g., a recombinant monoclonal antibody molecule, comprising a human Fc portion and a set of CDRs with specific affinity for a virion present in the lung of a subject.

In some embodiments, the antibody binds specifically to a single epitope on a single virion. In some embodiments, the antibody is a multimeric construct, e.g., wherein 2 or more Fabs (e.g., 2, 3, 4, 5, or more) are associated with a single Fc domain. The Fabs may be the same or different, and may recognize the same epitope on a virion, different epitopes on the same virion, or epitopes on different virions. The multimeric constructs are expected to facilitate more effective agglutination of both virus and/or virus-infected cells, resulting in more effective elimination from mucosal surfaces. Such multimeric antibody constructs can be prepared by linking multiple Fab domains via a flexible peptide linker. The heavy- and light-chain gene sequences for IgG control antibodies and each of the Fab-based multimeric antibodies may first be optionally codon-optimized, then synthesized and cloned into mammalian expression vectors (such as those offered by, e.g., Integrated DNA Technologies). For each format, Fab-components may be separated by a flexible peptide linker (e.g., amino acids comprising about 6 repeated units of GSSSS (SEQ ID NO:13), e.g., 2, 3, 4, 5, 6, 7, or 8 repeated units).

In some embodiments, the antibody may be a bispecific or multispecific construct against more than one virion. In one example, the construct may bind both RSV and metapneumovirus (MPV). In some embodiments, a bispecific antibody (e.g., Fab-IgG1, where an extra Fab is introduced in the N-terminus immediately adjacent to the native Fab of IgG) can be produced, e.g., by introducing separate orthogonal mutation sets (Lewis et al., *Nature Biotechnol.* 2014) into Fab A versus Fab B to ensure proper pairing of heavy and light chains. Fab A and Fab B may be combined with CH1/CL and Fc regions of human IgG1 Ab.

The CDRs may be any set of CDRs known in the art or later identified that specifically bind a virion.

In some embodiments, the virus is Ebola virus and the CDRs are selected from any combination of the CDRs found in known anti-Ebola virus antibodies.

In some embodiments, the virus is RSV and the CDRs are selected from any combination of the CDRs found in known anti-RSV antibodies. In some embodiments, the CDRs are from any of the antibody sequences disclosed in U.S. Pat. No. 8,562,996 (referred to as palivizumab, or SYNAGIS), incorporated by referenced herein in its entirety, or derivatives thereof (e.g., motavizumab, Wu H et al, 2007, J. Mol. Biol. 368, 652-665). In some embodiments, the CDRs may be one or more of the CDRs found in any of the heavy and light chain sequences below.

Heavy Chain Variable Region:
(SEQ ID NO: 1)
QVQLVQSGAEVKKPGSSVMVSCQASGGPLRNYIINWLRQAPGQGPEWMGGI

IPVLGTVHYAPKFQGRVTITADESTDTAYIHLISLRSEDTAMYYCATETAL

VVSTTYLPHYFDNWGQGTLVTVSS

Light Chain Variable Region:
(SEQ ID NO: 2)
DIQMTQSPSSLSAAVGDRVTITCQASQDIVNYLNWYQQKPGKAPKLLIYVA

SNLETGVPSRFSGSGSGTDFSLTISSLQPEDVATYYCQQYDNLPLTFGGGT

KVEIKRTV

Heavy Chain Variable Region:
(SEQ ID NO: 3)
QVTLRESGPALVKPTQTLTLTCTFSGFSLS TSGMSVG

WIRQPPGKALEWLA
              A
              A
              A

DIWWDDKKDYNPSLKS RLTISKDTSKNQVVLKVTNMDPADTATYYCAR
   H     D
   H     D

SMITNWYFDV WGAGTTVTVSS
(SEQ ID NO: 4)
        Q
(SEQ ID NO: 5)
  F      Q
(SEQ ID NO: 6)
D F F     Q
(SEQ ID NO: 7)
D F F     Q

Light Chain Variable Region:
(SEQ ID NO: 8)
DIQMTQSPSTLSASVGDRVTITC KCQLSVGYMH WYQQKPGKAPKLLIY
                      SASS
                      SASS
                      SASSR
                      SASSR DTSKLAS GVPSRFSGSGSGTEFTLTISSLQPDDFATYYC FQGSGYPFT
  F                                             F
  FF D FGGGTKLEIK
(SEQ ID NO: 9)
      V
(SEQ ID NO: 10)
      V
(SEQ ID NO: 11)
      V
(SEQ ID NO: 12)
      V Any of the antibodies described herein may be muco-trapping antibodies, configured to transiently bind to mucus, as described above. For example, in some embodiments, the antibody comprises an oligosaccharide at a glycosylation site, the oligosaccharide comprising, consisting essentially of, or consisting of a pattern correlating with (providing) enhanced trapping potency of the antibody in mucus, and wherein the antibody specifically binds an epitope of a target virion. The unique glycosylation pattern/unique oligosaccharide component of the antibody is designed to maximize trapping potency of the antibody once a plurality of antibodies are bound to the target virion, without unduly hindering the ability of the unbound antibody to diffuse readily through mucus to rapidly bind a target virion. In certain embodiments, the antibody is one that exhibits a mobility in mucus that is reduced no more than about 50%, e.g., no more than about 40%, 30, 20%, 10%, or 5%, relative to its mobility in solution (e.g., saline or water) and effectively traps a target virion in mucus based on a plurality of bound antibodies (e.g., at least 50% of virions slowed by at least 90%). In some embodiments, the antibody reduces the mobility of at least 50% of the virions, e.g., at least 60%, 70%, 80%, or 90% or more of the virions by at least 90%, e.g., at least 95%, 96%, 97%, 98%, or 99% or more. In other embodiments, the antibody reduces the percentage of virions that can penetrate mucus by at least 10%, e.g., at least 20%, 30%, 40%, 50%, 60%, 70%, 80%, 90%, or more. Based on the disclosure herein, one of skill in the art can readily identify/design oligosaccharide patterns that provide the desired trapping potency. In other embodiments, the antibody has a sufficient binding rate to an epitope of the target virion to accumulate on the surface of the target virion at sufficient levels to trap the target virion in mucus within one hour (e.g., within 30 minutes or 15 minutes) at an antibody concentration in the mucus of less than 5 µg/mL (e.g., less than 1 µg/mL or 0.1 µg/mL).

In some embodiments, the oligosaccharide component is bound to an N-linked glycosylation site in an Fc region of the antibody. The N-linked glycosylation site can be an asparagine residue on the Fc region of the antibody, for example, the Asn 297 asparagine residue. The amino acid numbering is with respect to the standard amino acid structure of a human IgG molecule.

As described in greater detail above, the N-glycan structure on human IgG-Fc is typically dominated by a biantennary core structure that shares a common core sugar sequence, Manα1-6(Manα1-3)Manβ1-4GlcNAcβ1-4GlcNAcβ1-Asn-X-Ser/Thr, with "antennae" initiated by N-acetylglucosaminyltransferases (GlcNAcTs) that help attach additional sugars to the core. In IgG found in human serum, the most common structures are those that contain both N-acetylglucosamine on each branch with one terminal galactose (39%), two terminal galactose (20%), or one terminal galactose and one terminal sialic acid (15%). Together, antibodies that comprise at least one terminal galactose represents about 74% of the IgG-Fc glycoforms. A pure GnGn form (with terminal N-acetylglucosamine on each branch without terminal galactose or sialic acid) may represent about 26% of the IgG-Fc glycoforms.

In some embodiments, the glycan does not contain any galactose residues. Without being limited by theory, it is believed that the presence of galactose compromises trapping potency. Antibodies with glycoforms that do not contain galactose represent just a small fraction of the entire repertoire of glycoforms found in nature. The use of a population of antibodies enriched with desirable glycoforms (whether naturally occurring or modified glycans) is advantageously used for trapping pathogens in mucus.

In some embodiments, the antibody of the invention is a mixture of antibodies having different oligosaccharide components. In some embodiments, the mixture of antibodies comprises at least about 20% (e.g., about 25%, about 30%, about 35%, about 40%, about 45%, about 50%, about 55%, about 60%, about 65%, etc.) antibodies having the core glycan structure described above (e.g., GnGn) with or without a fucose residue, e.g., at least about 40%, 50%, 60%, 70%, 80%, 90% or more.

In some embodiments, the mixture of antibodies is the mixture generated in a human cell line, e.g., a 293 cell line, e.g., a 293T cell line. In some embodiments, the mixture of antibodies is the mixture generated in a plant cell or in a plant.

The antibody may be useful for binding target virions to trap the pathogen in mucus of the respiratory tract to inhibit infection by the virions. Target virions of the antibody can include any virus that can infect a subject through a mucus membrane. Target virions further include synthetic systems comprising an antigen having an epitope, for example particles or particulates (e.g., polystyrene beads) comprising attached proteins, e.g., as might be used for bioterrorism.

Viruses include those that cause respiratory diseases, including, without limitation, influenza (including influenza A, B, and C); severe acute respiratory syndrome (SARS); respiratory syncytial virus (RSV); parainfluenza; adenovirus; human rhinovirus; coronavirus; and norovirus. Viruses also include those that do not necessarily cause respiratory disease but can infect a subject by entry through the respiratory tract, e.g., Ebola virus.

Viruses include those that affect non-human animals, such as livestock, e.g., swine (e.g., porcine reproductive and respiratory syndrome virus (PRRSV), swine influenza, porcine circovirus), ruminants (e.g., RSV, adenovirus, reovirus), ungulates (e.g., bocaparvovirus), horses (e.g., equine herpesvirus-1, equine herpesvirus-4, equine influenza virus), poultry (e.g., avian influenza virus, avian infectious bronchitis virus (IBV)), and the like.

The terms virus and viral pathogen are used interchangeably herein, and further refer to various strains of virus, e.g., influenza is inclusive of new strains of influenza, which would be readily identifiable to one of ordinary skill in the art.

In some embodiments, it is contemplated that an antibody according to the presently-disclosed subject matter is capable of broadly binding to viruses containing lipid envelopes, which are not necessarily specific to one virus.

It was surprisingly discovered that sub-neutralization doses of an antibody can be used to effectively trap a target virion in mucus. As such, in some embodiments, wherein the antibody specifically binds a neutralizing epitope of the target virion, a sub-neutralization dose can be used. A sub-neutralization dose is a dose below that which would be needed to achieve effective neutralization.

As will be recognized by one of skill in the art, appropriate doses may differ between virions, between mucosal surfaces, and also between individuals. It will also be recognized that different subjects and different mucosal surfaces may have different optimal glycan patterns and optimal antibody-mucin affinities, contributing to different optimal doses.

It is further proposed herein that antibodies that selectively bind non-neutralizing epitopes of a target virion can be used to effectively trap the target virion in mucus. As such, in some embodiments, the antibody specifically binds a non-neutralizing epitope, e.g., one or more non-neutralizing epitopes.

The presently-disclosed subject matter further includes an antibody that selectively binds a conserved epitope of a target virion. A benefit of targeting a conserved epitope would be to preserve efficacy of the antibody as against new strains of the virus. Targeting such epitopes has been avoided at times in the past because they were viewed as being ineffective targets; however, in view of the disclosure herein that non-neutralizing epitopes can serve as effective targets and/or that sub-neutralization doses can be effective for inhibiting infection, previously dismissed conserved epitopes of target virions can be seen as effective targets.

As noted above, it was determined that the low-affinity binding interactions that an antibody forms with mucins are influenced by antibody glycosylation, and are also Fc-dependent. As such, the presently-disclosed subject matter includes antibodies having a preserved and/or engineered Fc region. Such antibodies can be, for example, one or more of IgG, IgA, IgM, IgD, or IgE. In certain embodiments, the antibodies are IgG. In some embodiments, the antibodies are one or more subclasses of IgG, e.g., IgG1, IgG2, IgG3, IgG4, or any combination thereof.

In some embodiments, the antibody has a sufficient binding rate and/or binding affinity to an epitope of the target virion to accumulate on the surface of the virion at sufficient levels to trap the virion within one hour after administration of the antibody at an antibody concentration of less than about 5 µg/mL, although excess antibody may be used (e.g., about 5 µg/mL or more, 10 µg/mL or more, 15 µg/mL or more, 20 µg/mL or more, 25 µg/mL or more, 30 µg/mL or more, 40 µg/mL or more, 50 µg/mL or more, 60 µg/mL or more, 70 µg/mL or more, 80 µg/mL or more, 90 µg/mL or more, 100 µg/mL or more, etc.). The term "trap" in this instance refers to reduction of further movement through the mucus. In some embodiments, the target virion may be trapped within about 30 minutes, e.g., about 25, 20, 15, or 10 minutes after administration of the antibody. In some embodiments, the antibody traps the target virion at an antibody concentration of less than about 4, 3, 2, or 1 µg/mL.

As mentioned, formulations for administration, including intranasal administration, etc., are contemplated for use in connection with the presently-disclosed subject matter. All formulations, devices, and methods known to one of skill in the art which are appropriate for delivering the antibody or composition containing the antibody to one or more mucus membranes of the respiratory tract of a subject can be used in connection with the presently-disclosed subject matter. The antibody can be formulated for nasal administration or otherwise administered to the lungs of a subject by any suitable means, e.g., administered by an aerosol suspension of respirable particles comprising the antibody, which the subject inhales. The respirable particles can be liquid or solid. The term "aerosol" includes any gas-borne suspended phase, which is capable of being inhaled into the bronchioles or nasal passages. Specifically, aerosol includes a gas-borne suspension of droplets, as can be produced in a metered dose inhaler or nebulizer, or in a mist sprayer. Aerosol also includes a dry powder composition suspended in air or other carrier gas, which can be delivered by insufflation from an inhaler device, for example. See Ganderton & Jones, *Drug Delivery to the Respiratory Tract*, Ellis Horwood (1987); Gonda (1990) *Critical Reviews in Therapeutic Drug Carrier Systems* 6:273-313; and Raeburn et al., *J. Pharmacol. Toxicol. Meth.* 27:143 (1992). Aerosols of liquid particles comprising the antibody can be produced by any suitable means, such as with a vibrating mesh nebulizer, a pressure-driven aerosol nebulizer, or an ultrasonic nebulizer, as is known to those of skill in the art. See, e.g., U.S. Pat. No. 4,501,729. Aerosols of solid particles comprising the antibody can likewise be produced with any solid particulate medicament aerosol generator, by techniques known in the pharmaceutical art. In some embodiments, the nebulizer and nebulization conditions are selected to produce aerosol particles of a desired size. In one embodiment, the nebulized composition has a Mass Median Aerodynamic Diameter (MMAD) in the 2-5 mm range, as measured using a Next Generation Impactor.

In some embodiments of the presently-disclosed subject matter, a composition includes a first antibody and a second antibody, as disclosed herein, wherein the first antibody specifically binds a first epitope of the target virion and the second antibody specifically binds a second epitope of the target virion, wherein said first epitope is distinct from the second epitope. In certain embodiments, the composition includes three or more different antibodies, e.g., 3, 4, 5, 6, 7, 8, 9, 10, or more different antibodies, wherein each antibody specifically binds a different epitope of the target virion.

It may also be desirable to provide a composition that can provide treatment or prevention of infection due to more than one target virus. In some embodiments of the presently-disclosed subject matter, a composition includes a first antibody and a second antibody, as disclosed herein, wherein the first antibody specifically binds an epitope of a first target virion and the second antibody specifically binds an epitope of second target virion. In certain embodiments, the composition includes three or more different antibodies, e.g., 3, 4, 5, 6, 7, 8, 9, 10, or more different antibodies, wherein each antibody specifically binds an epitope of a different target virion.

In some embodiments, the pharmaceutical composition can further include an additional active agent, e.g., a prophylactic or therapeutic agent. For example, the additional active agent can be an antimicrobial agent, as would be known to one of skill in the art. The antimicrobial agent may be active against algae, bacteria, fungi, parasites (helminths, protozoa), viruses, and subviral agents. Accordingly, the antimicrobial agent may be an antibacterial, antifungal, antiviral, antiparasitic, or antiprotozoal agent. The antimicrobial agent is preferably active against infectious diseases. Examples of suitable antimicrobial agents (e.g., one or more antibacterial, antifungal, antiviral, antiparasitic, or antiprotozoal agents) include those described above.

The presently-disclosed subject matter further includes methods of treating, inhibiting, or preventing a viral infection in a subject in need thereof, the viral infection characterized by a virion in the lung of the subject, the method comprising administering, via an inhaled route, a recombinant monoclonal antibody molecule comprising a human Fc portion and a set of CDRs with specific affinity for the virion, thereby treating, inhibiting, or preventing the infection. The recombinant monoclonal antibody molecule can be an antibody and/or composition as disclosed herein. In certain embodiments, the methods comprise additional steps such as one or more of isolating the antibodies, preparing a composition of the isolated antibodies, determining the level of antibodies in the mucus of the subject before administering the antibodies, and determining the level of antibodies in the mucus of the subject after administering the antibodies.

The virion may be any virus as discussed herein. In some embodiments, the virion is Ebola virus. In some embodiments, the virion is RSV. In some embodiments, the antibody comprises any of the CDR sequences disclosed herein.

The antibodies and compositions of the present invention according to the methods described herein are administered or otherwise applied by delivering the composition, e.g., to the lungs, e.g., by inhalation. The subject may be one where an infection is already present in the lungs (an actual site of infection) or where an infection is likely to occur in the lungs (a potential site of site of infection in an uninfected individual). In some embodiments, the antibodies and compositions may be delivered to the respiratory tract, e.g., the nasal cavity and the lungs, by any method known in the art to be effective. In some embodiments, the antibodies and compositions may be delivered directly to the respiratory tract. In other embodiments, the antibodies and compositions may be systemically delivered such that the antibodies are secreted into the mucus of the subject. Accordingly, the compositions as described above may be delivered to a mucosal surface of the respiratory tract.

In some embodiments, the antibody is formulated for delivery to the respiratory tract. In some embodiments, the molecule is formulated as an aerosol composition. In some embodiments, the aerosol composition is suitable for nebulization. Any type of suitable nebulizer may be used. In one embodiment, the aerosol composition is nebulized by a vibrating mesh nebulizer. In some embodiments, the nebulizer and nebulization conditions are selected to produce aerosol particles of a desired size. In one embodiment, the nebulized composition has a Mass Median Aerodynamic Diameter (MMAD) in the 2-5 mm range, as measured using a Next Generation Impactor.

An effective amount of the antibody can be administered. As used herein, an "effective amount" of the antibody for inhibition or prevention of infection refers to a dosage sufficient to inhibit or prevent infection by the target virion. As used herein, an "effective amount" of the antibody for treatment of infection refers to a dosage sufficient to inhibit spread of the target virion from infected cells to non-infected cells in the subject and/or to inhibit spread of the target virion from the infected subject to another subject, e.g., a non-infected subject. The effective amount can bean amount sufficient to trap an amount of the target virion in mucus. As will be recognized by one of skill in the art, the amount can vary depending on the patient and the target virion. The exact amount that is required will vary from subject to subject, depending on the species, age, and general condition of the subject, the particular carrier or adjuvant being used, mode of administration, and the like. As such, the effective amount will vary based on the particular circumstances, and an appropriate effective amount can be determined in a particular case by one of skill in the art using only routine experimentation. In some instances, an effective amount of the antibody that specifically binds the target virion can be an amount that achieves a concentration of the antibody in the mucus of about 50 ng/mL to about 1000 μg/mL, e.g., about 0.1 μg/mL to about 100 μg/mL, about 0.5 μg/mL to about 100 μg/mL, about 1 μg/mL to about 50 μg/mL, about 5 μg/mL to about 500 μg/mL, about 5 μg/mL to about 300 μg/mL, about 20 μg/mL to about 200 μg/mL, or any range therein (e.g., between 0.5 μg/mL. to about 20 μg/mL).

In some embodiments, the antibody may be administered in two or more stages with different doses in each stage. For example, higher doses can be administered initially in order to clear target virions that are present in the mucus of exposed or infected subjects and ensure that sufficient amounts of antibody remain in the mucus to provide protection, e.g., for about 24 hours. In later stages, lower doses can be administered to maintain protective levels of the antibody. In other embodiments, protective doses can be administered to subjects that are likely to be exposed to a virus and higher doses can be administered if infection occurs.

In some embodiments, the antibody or composition is administered at regular intervals until an effect is achieved. The interval may be e.g., multiple times a day (e.g., every 1, 2, 3, 4, 5, 6, 8, 12, 18 or 24 hours, e.g., every 3-24 hours)), once every 24, 48, or 72 hours, or once a week.

As will be recognized by one of skill in the art, the term "inhibiting" or "inhibition" or "preventing" or "prevention" does not refer to the ability to completely eliminate the possibility of infection in all cases. Rather, the skilled artisan will understand that the term "inhibiting" or "preventing" refers to reducing the chances of virions moving through mucus beyond the mucus membrane such that infection of a subject can occur, such as reducing chances of infection by a virion when such virion is bound to trapping antibodies in mucus. Such decrease in infection potential can be determined relative to a control that has not been administered the antibodies of the invention. In some embodiments, the decrease of inhibition potential relative to a control can be about a 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% decrease.

In some embodiments inhibiting or treating an infection in a subject can comprise trapping a virion in mucus. As such, in some embodiments a method of trapping a target virion in mucus is provided, which method includes administering to a mucosa of the respiratory tract of the subject an antibody or composition as described herein.

In some embodiments, a method of inhibiting or treating an infection in a subject, and/or trapping a virion in the mucus of a subject, involves administering to a mucosa of the respiratory tract of the subject a composition comprising an isolated antibody that specifically binds a non-neutralizing epitope of a target virion. The antibody can be a non-neutralizing antibody. In some embodiments, the non-neutralizing antibody is provided at a concentration above a predetermined amount.

In some embodiments, a method of inhibiting or treating an infection in a subject, and/or trapping a virion in the mucus of a subject, involves administering to a mucosa of the respiratory tract of the subject a composition comprising an isolated antibody that specifically binds a neutralizing epitope of a target virion, wherein the antibody is provided at a sub-neutralization dose.

Having described the present invention, the same will be explained in greater detail in the following examples, which are included herein for illustration purposes only, and which are not intended to be limiting to the invention.

Example 5

Blocking Penetration of Ebola Viruses in Human Airway Mucus

Ebola virus, a member of the filovirus family of viruses that cause severe and often fatal hemorrhagic fevers, readily infects many cell types, including immune cells, fibroblasts, endothelial cells and epithelial cells. Given the broad tissue tropism of Ebola, effective treatments of systemic Ebola infection generally require high doses of therapeutic molecules administered systemically. For instance, ZMapp™, a cocktail of three chimeric monoclonal antibodies, was evaluated at 50 mg/kg in a randomized, controlled clinical trial in Guinea, Sierra Leone and Liberia during the 2014-2016 Ebola outbreak.

Rather than treating Ebola infections systemically, a potential alternative strategy is to block or treat infections at the portals of entry before virions proliferate and spread throughout the body. In addition to transmission by direct contact with the blood, bodily fluids, or skin of Ebola-positive individuals, it is possible that Ebola may be transmitted via virus-laden droplets generated from a heavily infected individual by coughing, sneezing, vomiting or medical procedures that are directly propelled onto the mucus membranes of a nearby person. The term droplet-based aerosol transmission may be used to differentiate this potential mechanism from strict airborne transmission of individual viruses, which is generally considered an unlikely mechanism of Ebola transmission. While aerosol transmission of Ebola has not been ascertained in humans, it has been demonstrated in multiple animal studies, including with non-human primates. Given the possibility of aerosol transmission of Ebola to humans, as well as the potential threat of aerosolized filovirus-based biowarfare agents, we sought to investigate the fate of Ebola deposited at mucosal surfaces.

Mucus membranes are characterized by a layer of mucus secretions that can trap diverse foreign particles and pathogens, facilitate their elimination via natural mucus clearance mechanisms, and consequently reduce the flux of pathogens reaching target cells. Human airway mucus (AM) is likely responsible in part for the relatively modest transmission rates of many respiratory viruses, but it is also likely that AM can be reinforced to further limit the flux of pathogens reaching the underlying epithelium. As described above, IgG antibodies (Ab) in cervicovaginal mucus can trap viruses in mucus via multiple low-affinity Fc-mucin bonds between IgG accumulated on the virus surface and mucins, akin to a Velcro® patch. Further, the immobilization of H1N1 and H3N2 influenza viruses in human AM may be correlated to the presence of influenza-binding IgG and IgA. Here, we investigate whether topically dosed IgG against Ebola may similarly trap Ebola in AM and facilitate their elimination from the airways.

Ebola virus-like particles (VLP) were prepared by transfecting 293T cells with plasmids encoding Gag-mCherry and Ebola GP. 293T cells were maintained in Dulbecco's Modified Eagle's Medium (DMEM; Sigma-Aldrich, St. Louis, MO) supplemented with 10% fetal calf serum (FBS) and 2 mM L-glutamine (DMEM-10). All cell cultures were maintained at 37° C. in a humidified 5% $CO_2$ atmosphere. 293T cells ($2.0\times10^6$) were seeded in a 25 $cm^2$ flask (Thermo Scientific, Rochester, NY) and transfected with the expression plasmids using X-tremeGENE HP DNA Transfection Reagent (Roche Diagnostics, Indianapolis, IN). Gag-mCherry and Ebola GP plasmids were mixed in a 1:1 ratio (1.5 μg of each), and added to 500 μL of serum free DMEM with 9 μL of X-tremeGENE HP DNA Transfection Reagent. The mixture was incubated at room temperature for 30 min before being added to the culture of 293T cells. After 3 to 5 hr incubation at 37° C. in 5% $CO_2$, transfected cells were washed extensively with DMEM and incubated for additional 24-48 hr with 2 mL of DMEM-10 at 37° C. in 5% $CO_2$. Supernatants from virus particle-producing cultures were then collected and clarified by centrifugation for 10 min at 300×g, filtered through a low protein binding 0.45 m syringe filter (Millipore, Bedford, MA) and partially purified through 25% w/v sucrose in Hepes-NaCl buffer by centrifugation at 221,630×g at 4° C. for 2.5 hr. The pellet was resuspended overnight at 4° C. in 10% sucrose in Hepes-NaCl buffer, aliquoted, and stored at −80° C.

Figures 14A, 14B:
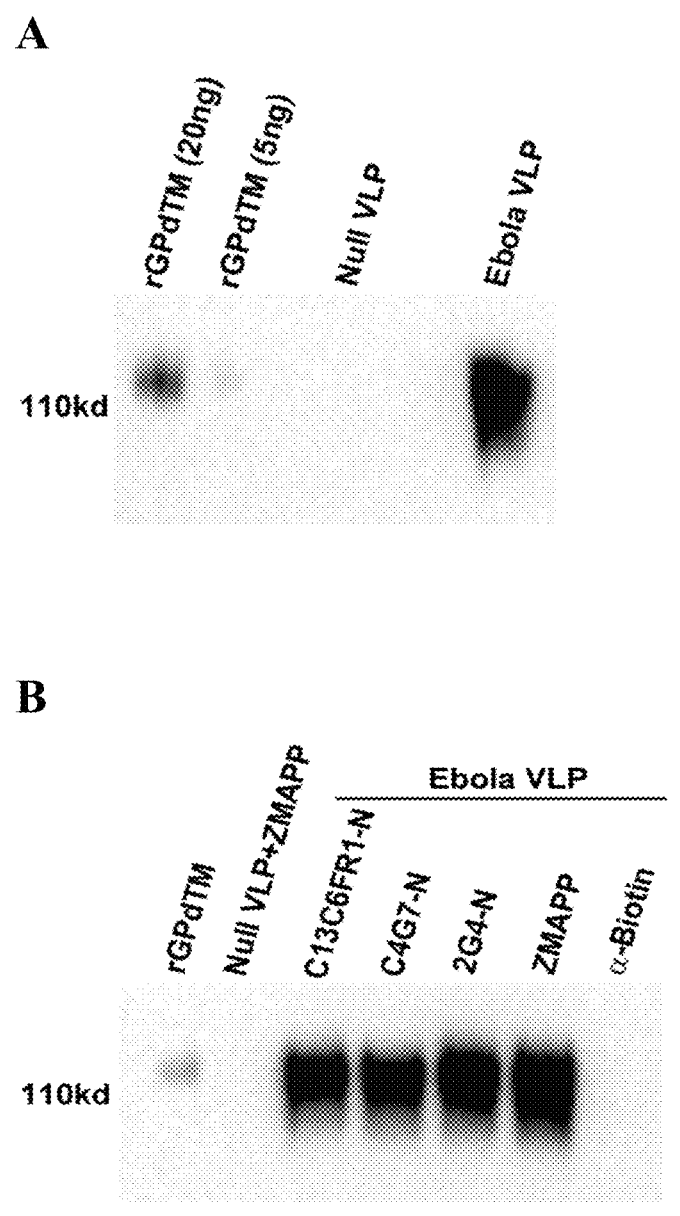

To measure incorporation of Ebola GP protein into the VLP, sucrose gradient-purified VLP were lysed in buffer containing 100 mM Tris-HCl (pH 8.0), 100 mM NaCl, 2% Triton X-100 and protease inhibitors at 4° C. for 30 min. Recombinant Ebola glycoprotein rGPdTM (#0501-001; IBT Bioservices, Rockville, MD) was run as a positive control. Samples were boiled in SDS-PAGE sample buffer with 2-mercaptoethanol and separated on 4%-12% Tris-Glycine gradient gels (Invitrogen, Grand Island, NY), transferred to nitrocellulose membranes, and probed with Mouse Ebola GPII Monoclonal Antibody (MyBioSource, San Diego, CA) at a concentration of 1:2,000, as shown in FIG. 14A. Specificity of ZMapp™ binding to Ebola VLP was demonstrated via immunoprecipitation. Ebola VLP were incubated with ZMapp™, individual Ebola-binding IgG, or α-Biotin at 4° C. for 3 hr. The antigen-antibody complex was pulled down using Protein G beads, and Ebola GP was probed as described above, and shown in FIG. 14B. The hydrodynamic diameter of Ebola VLP was measured using a NanoSight NS500 (Malvern Instruments, Malvern, UK). Samples were diluted to a concentration of $\sim 10^8$ particles/mL in 20 nm filtered PBS, and five 60 second videos were taken of each sample.

Both the ZMapp™ and any of the individual Ebola-binding mAbs used herein were modified to enhance musical binding, by enriching the population of Ebola-binding mAbs to include a majority (e.g., 50% or more, 55% or more, 60% or more, 65% or more, 70% or more 75% or more, 80% or more 85% or more, etc. such as 85%-95% etc.) having a G0 glycosylation pattern on the Fc region (e.g., a glycosylation pattern comprising the biantennary core glycan structure Manα1-6(Manα1-3)Manβ1-4GlcNAcβ1-4GlcNAcβ1 with terminal N-acetylglucosamine on each branch). Native anti-Ebola mAb (e.g., human anti-Ebola mAb) has a much lower G0 content.

Fluorescent, carboxyl-modified polystyrene beads (PS—COOH) and PEGylated nanoparticles (PS-PEG) sized approximately 100 nm were prepared and characterized. Fluorescent, carboxyl-modified polystyrene beads (PS—COOH) sized 100 nm were purchased from Molecular Probes (Eugene, OR). PEGylated nanoparticles (PS-PEG) were prepared by conjugating 2 kDa amine-modified PEG (Rapp Polymere, Tuebingen, Germany) to PS—COOH particles via a carboxyl-amine reaction. Particle size and ζ-potential were determined by dynamic light scattering and laser Doppler anemometry, respectively, using a Zetasizer Nano ZS (Malvern Instruments, Southborough, MA). Size measurements were performed at 25° C. at a scattering angle of 90°. Samples were diluted in 10 mM NaCl solution, and measurements were performed according to instrument instructions. PEG conjugation was confirmed by a near-neutral ζ-potential (Table 3).

TABLE 3

Characterization of PEG-modified nanoparticles. Size and ζ-potential values for carboxyl-modified beads are provided for comparison.

| Size (nm)* | Surface Chemistry | Diameter (nm) | ζ-potential (mV) |
|---|---|---|---|
| 100 | COOH | 109 ± 4 | −55 ± 5 |
| 100 | PEG | 132 ± 3 | −7 ± 3 |

*Provided by the manufacturer.

Fresh human airway mucus (AM) was obtained from healthy adult patients (Table 4) intubated for general anesthesia during elective surgery, following a protocol that was deemed non-human subjects research by the University of North Carolina at Chapel Hill Institutional Review Board. After surgery, the endotracheal tube was removed from the patient, and mucus coating the tube was collected by gentle centrifugation. AM that was non-uniform in color or consistency or had visible blood contamination was discarded. Samples were treated with protease inhibitor immediately after collection to minimize potential enzymatic degradation, and stored at 4° C. until microscopy, typically within 24 hr.

TABLE 4

Demographic information for donors of airway mucus specimens.

| Donor ID | Gender | Age | Smoker Status |
|---|---|---|---|
| AM01 | F | 28 | N |
| AM02 | M | 39 | N |
| AM03 | M | 22 | Y |
| AM04 | F | 48 | Y |
| AM05 | F | 59 | N |
| AM06 | F | 66 | N |
| AM07 | F | 66 | N |
| AM08 | F | 61 | N |
| AM09 | M | 26 | N |
| AM10 | F | 62 | N |
| AM11 | M | 88 | Y |
| AM12 | M | 55 | N |

Total immunoglobulin levels in AM were quantified by conventional ELISA and confirmed using the Human Isotyping Kit on Luminex (HGAMMAG-301K; Millipore, Billerica, MA) according to manufacturer protocol. Briefly, 20× stock isotyping beads were vortexed, sonicated, diluted to 1×, and incubated with 50 μL of serially diluted AM supernatant at 1:2 beads:AM volume ratio. After 1 hr, the beads were separated from AM supernatant using a magnetic plate, and washed twice with wash buffer. The beads were then incubated with 25 μL of 1× anti-Human Kappa and Lambda-PE for 1 hr, washed twice, and resuspended in Luminex Drive Fluid. Fluorescence intensities indicative of immunoglobulin levels present in AM were measured using the Luminex MAGPIX system, and data analysis was performed using Milliplex Analyst (v3.5.5.0; Vigene Tech Inc., Carlisle, Mass.). All incubations were carried out at room temperature in the dark with vigorous agitation. Total Ig and IgG isotypes levels are shown in (Table 5).

TABLE 5

Characterization of immunoglobulin levels in airway mucus.

| Donor ID | $IgG_1$ | $IgG_2$ | $IgG_3$ | $IgG_4$ | Total IgG (μg/mL) | Total IgA (μg/mL) | Total IgM (μg/mL) |
|---|---|---|---|---|---|---|---|
| AM01 | 57.4% | 33.0% | 8.3% | 1.2% | 559 | 730 | 107 |
| AM02 | 69.8% | 23.6% | 6.6% | 0.0% | 3,171 | 360 | 90 |
| AM03 | 11.0% | 78.9% | 7.6% | 2.4% | 109 | 28 | 14 |
| AM04 | 52.3% | 45.2% | 2.1% | 0.4% | 1,481 | 196 | 48 |
| AM05 | 9.8% | 88.0% | 1.6% | 0.6% | 6,138 | 123 | 465 |
| AM06 | 45.8% | 44.4% | 7.3% | 2.4% | 3,788 | 645 | 657 |
| AM07 | 45.4% | 47.9% | 2.3% | 4.3% | 3,927 | 1,005 | 416 |
| AM08 | 25.3% | 67.9% | 5.0% | 1.8% | 1,951 | 290 | 452 |
| AM09 | 24.6% | 65.9% | 5.7% | 3.8% | 158 | 36 | 25 |
| AM10 | 16.9% | 73.8% | 8.2% | 1.1% | 387 | 127 | 36 |
| AM11 | 57.3% | 33.6% | 7.0% | 2.1% | 110 | 339 | 24 |
| AM12 | 39.9% | 51.6% | 8.4% | 0.2% | 481 | 602 | 115 |
| Median | 42.6% | 49.7% | 6.8% | 1.5% | 1,020 | 315 | 99 |
| SEM | 5.8% | 5.8% | 0.7% | 0.4% | 550 | 85 | 63 |

Dilute particle solutions (~$10^8$-$10^9$ particles/mL, 1 μL) and different Ab (2 μL, to a final concentration of 22 μg/mL) were added to 20 μL of fresh, undiluted AM in custom-made chambers, and samples were incubated 1 hr at 37° C. before microscopy for Multiple particle tracking analysis. All conditions were tested in aliquots of the same AM samples, allowing direct comparison between conditions. The trajectories of the fluorescent particles in AM were recorded using an EMCCD camera (Evolve 512; Photometrics, Tucson, AZ) mounted on an inverted epifluorescence microscope (AxioObserver D1; Zeiss, Thornwood, NY), equipped with an Alpha Plan-Apo 100×/1.46 NA objective, environmental (temperature and $CO_2$) control chamber and an LED light source (Lumencor Light Engine DAPI/GFP/543/623/690). Videos (512×512, 16-bit image depth) were captured with MetaMorph imaging software (Molecular Devices, Sunnyvale, CA) at a temporal resolution of 66.7 ms and spatial resolution of 10 nm (nominal pixel resolution 0.156 μm/pixel). The tracking resolution was determined by tracking the displacements of particles immobilized with a strong adhesive. Particle trajectories were analyzed using Video SpotTracker (University of North Carolina, Chapel Hill, NC). Sub-pixel tracking resolution was achieved by determining the precise location of the particle centroid by light-intensity-weighted averaging of neighboring pixels. Trajectories of n≥130 particles per frame on average (typically corresponding to n≥300 total traces) were analyzed for each experiment, and 8-9 independent experiments for each condition were performed in AM collected from unique subjects. The coordinates of particle centroids were transformed into time-averaged mean squared displacements (MSD), calculated as $<\Delta r^2(\tau)>=[x(t+\tau)-x(t)]^2+[y(t+\tau)-y(t)]^2$ (where τ=time scale or time lag), from which distributions of MSDs and $D_{eff}$ were calculated. Mobile particles were defined as those moving more than approximately 200 nm (i.e. roughly twice the particle diameter) within 0.2667 s.

MSD may also be expressed as $MSD=4D_0\tau^\alpha$, where α, the slope of the curve on a log-log scale, is a measure of the extent of impediment to particle diffusion (α=1 for pure unobstructed Brownian diffusion; α<1 indicates increasing impediment to particle movement as a decreases). A limitation with 15D particle tracking is the inability to track rapidly diffusing species due to diffusion out of the focal plane, particularly with sub 200 nm species. Consequently, MSD calculations at longer time scales will underestimate the true mobility of these species. Therefore, a was calculated only over the linear portion of the log-log MSD curve (here, up to τ=0.6 s). Calculating a to span τ=1 s results in a value of 0.71 vs. 0.80 for Ebola VLP in AM with no Ab, but had negligible impact on a values for Ebola VLP in AM treated with ZMapp™ or individual mAb.

In order to predict particle population behavior, we performed a first passage time analysis, calculating the expected time for 10% and 50% of a particle population to pass through a 50 μm thick layer of mucus. Given the diffusivity D of a particle, the probability that the particle has not passed through a layer of thickness L as of a given time t may be described by an explicit "survival function". Using T to denote the time it takes for the particle to pass through the layer, the formula for this "survival function" is $$P(T > t | D) = \frac{4}{\pi} \sum_{k=0}^{\infty} \frac{(-1)^k}{2k+1} \exp\left(\frac{-(2k+1)^2 \pi^2 Dt}{4L^2}\right).$$

Suppose that a heterogeneous population of particles have individual diffusivities $\{D_i\}$ with respective weights $\{w_i\}$ where i ranges from 1 to the number of particles N. The expected fraction of particles that remain in the fluid layer as of time t is then equivalent to the following weighted survival function:

$$P(T > t) = \frac{\sum_{i=1}^{N} P(T > t | D_i) w_i}{\sum_{i=1}^{N} w_i}.$$

We set $w_j$ to be the number of frames in which the $i^{th}$ particle is present. For each weighting, we calculated the times $\tau_{10}$ and $\tau_{50}$ for which $P(T>\tau_{10})=0.9$ and $P(T>\tau_{50})=0.5$.

A slightly hypotonic buffer, prepared by diluting Gibco@ 1×PBS with an equal volume of Milli-Q® water to ~150 mOsm/kg, was used to deliver Ebola VLP to the mouse lung (hypotonic solutions were found to promote advective flow to the epithelium, allowing us to more rigorously evaluate whether ZMapp™ Ab can prevent Ebola from crossing the AM layer). ZMapp™ cocktail (c2G4, c116C6FR1 and c4G7 mixed at a 1:1:1 ratio, total 25 μL per mouse) or hypotonic PBS was first loaded into a Penn Century Microsprayer (FMJ-250; Penn Century, Inc., Wyndmoor, PA), aerosolized and delivered to the airways of Balb/c mice (female, 8-10 weeks) anesthetized in an isoflurane chamber. After 15 min, Ebola VLP prepared in hypotonic PBS were instilled using the microsprayer at 25 μL per mouse, for both ZMapp™-treated and control mice. A third set of mice were treated with two instillations of hypotonic PBS to measure the autofluorescence of mouse lung tissue. Experimental and control groups had n=3 mice each. All experimental protocols were approved by the University of North Carolina at Chapel Hill Institutional Animal Care and Use Committee, and conform to the Declaration of Helsinki conventions for the use and care of animals.

To investigate the distribution of Ebola VLP, mice were euthanized 30 min after the final microsprayer instillation and the entire lung, including trachea, was dissected. The dissected lung was kept intact, washed with 1×PBS, and embedded in 100% optimal cutting temperature (OCT) compound before freezing at −80° C. After overnight freezing, 10 μm thick transverse cross sections of the upper airways were obtained via cryosectioning at −20° C. and stained with DAPI. Cryosections were imaged using an Olympus FV1000 MPE laser scanning confocal microscope (Olympus Life Science Solutions, Center Valley, PA) at 20× magnification and the following excitation/emission spectrum: TRITC (559/603 nm) and DAPI (405/422 nm). Fluorescence intensity was quantified using ImageJ (National Institutes of Health, Bethesda, MD) for on average 10 cross sections per mouse, and background fluorescence was subtracted.

Data averages are presented as means with standard error of the mean (SEM) indicated. Statistical comparisons were limited to two groups. A one-tailed, paired Student's-test was used for all comparisons, since different conditions were tested in aliquots of the same mucus samples. Differences were deemed significant at an alpha level of 0.05.

The Ebola virus-like particles were found to quickly penetrate human airway mucus. Wild-type Ebola virus requires Biosafety Level 4 containment that few laboratories have access to. Therefore, to investigate the fate of Ebola in mucus, we prepared fluorescent, non-infectious Ebola VLP comprised of HIV-1 Gag-mCherry capsid proteins in the core and the Zaire glycoprotein (GP), from the same species as in the West Africa epidemic in 2014-2016, on the surface. The same strategy was previously used to prepare both HIV and influenza VLP. GP incorporation into Ebola VLP was confirmed via Western blot (FIG. 14A), and dynamic light scattering showed that the VLP possessed a hydrodynamic diameter of 102±3 nm. All three IgGs of the ZMapp™ cocktail bound specifically to the VLP, confirming the presence of structurally-intact GP (FIG. 14B).

Figures 15A, 15B, 15C, 15D:
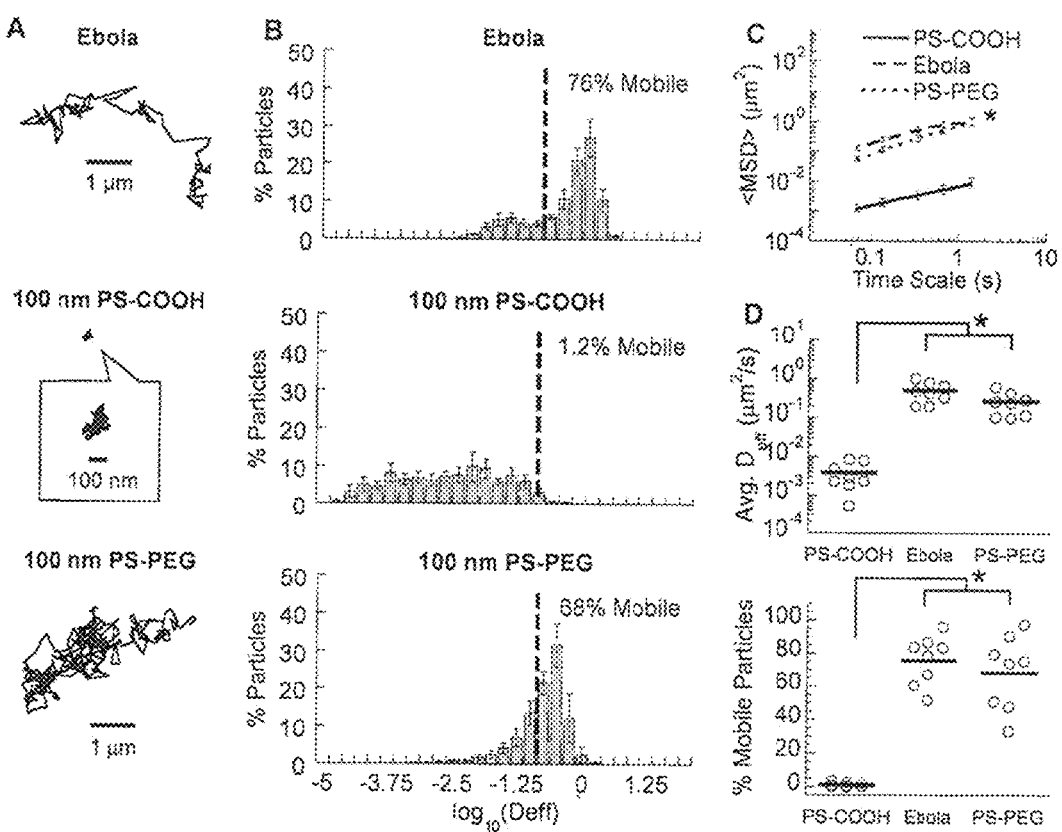
FIGS. 15A-15D show diffusion in human airway mucus (AM) of Ebola VLP and comparably sized polystyrene nanoparticles that are either carboxylated and mucoadhesive (PS—COOH) or modified with polyethylene glycol and muco-inert (PS-PEG). (A) Representative trajectories for VLP and particles exhibiting effective diffusivities within one SEM of the ensemble average at a time scale of 0.2667 s. (B) Distributions of the logarithms of individual particle effective diffusivities (D$_{eff}$) at a time scale of 0.2667 s. Log D$_{eff}$ values to the left of the dashed line correspond to particles with displacements of less than approximately 200 nm (i.e., roughly twice the particle diameter) within 0.2667 s or D$_{eff}$ approximately 20-fold reduced from theoretical diffusivity in water. (C) Ensemble-averaged geometric mean square displacements (<MSD>) as a function of time scale. (D) Ensemble geometric D$_{eff}$ at a timescale of 0.2667 s and fraction of mobile particles are plotted for distinct samples with averages indicated by solid lines. Data represent the ensemble average of 8 independent AM specimens. Error bars represent standard error of the mean (SEM). * indicates a statistically significant difference compared to PS—COOH (p<0.05) based on a one-tailed, paired Student's t-test.

To avoid the effects of dilution with using hypertonic saline to induce sputum expectoration, we obtained undiluted human airway mucus directly from freshly extubated endotracheal tubes. Ebola VLP were readily diffusive in all AM secretions tested, as shown in FIG. 15A, exhibiting diffusive motion comparable to that of similarly-sized, polyethylene glycol-coated polystyrene (PS-PEG) nanoparticles engineered to evade adhesion to mucins and penetrate various mucus secretions. In the same AM secretions, similarly sized carboxyl-modified polystyrene (PS—COOH) nanoparticles that are muco-adhesive were extensively immobilized, confirming that the rapid diffusivity observed for Ebola VLP was not due to a degraded mucin matrix. Nearly all Ebola VLP (>75% in all samples, on average ~90%) possessed diffusivities in excess of approximately 200 nm, or twice the particle diameter, at a time scale of 0.2667 s, as shown in FIG. 15B. The geometrically averaged ensemble mean squared displacement (<MSD>) of Ebola was only ~10-fold reduced compared to their theoretical speeds in buffer (FIG. 15C; at a time scale of 0.2667 s), with a slope a of 0.80 for the log <MSD> vs. log time scale plot ($\alpha$=1 for pure unobstructed Brownian diffusion, e.g., particles in water, and a becomes smaller and approaches zero as obstruction to Brownian diffusion increases). The geometrically averaged effective diffusivity (<$D_{eff}$>) for Ebola VLP was 0.43 μm$^2$/s, about 150-fold higher than that of PS—COOH nanoparticles (FIG. 15D).

Figure 17A:
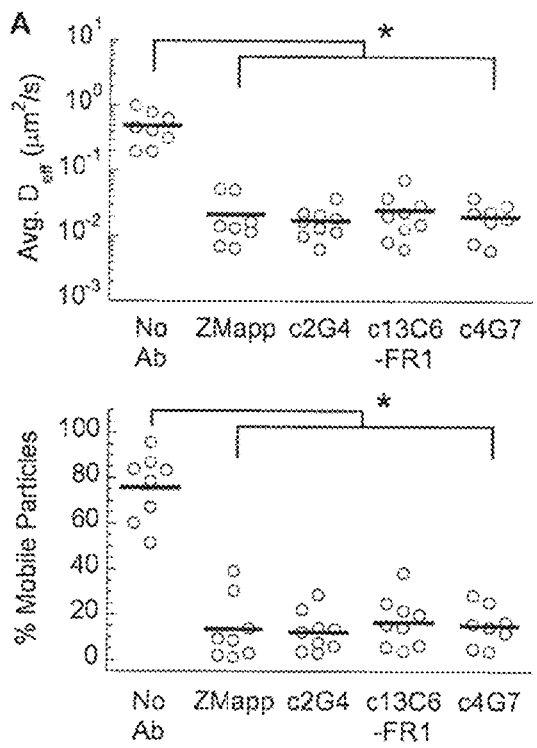
FIGS. 17A-17B show diffusion and first passage time of Ebola VLP in human AM that is untreated (No Ab) or treated with either ZMapp™ or individual Ebola-binding IgG (c2G4, c116C6FR1, c4G7). (A) Ensemble geometric average $D_{eff}$ at a timescale of 0.2667 s and fraction of mobile particles. (B) Estimated time for 10% and 50% of VLP and particles to diffuse through a 50 µm thick mucus layer. Data represent the ensemble average of 8-9 independent AM specimens. Error bars represent standard error of the mean (SEM). * indicates a statistically significant difference compared to No Ab (p<0.05) based on a one-tailed, paired Student's t-test.
Figure 17B:
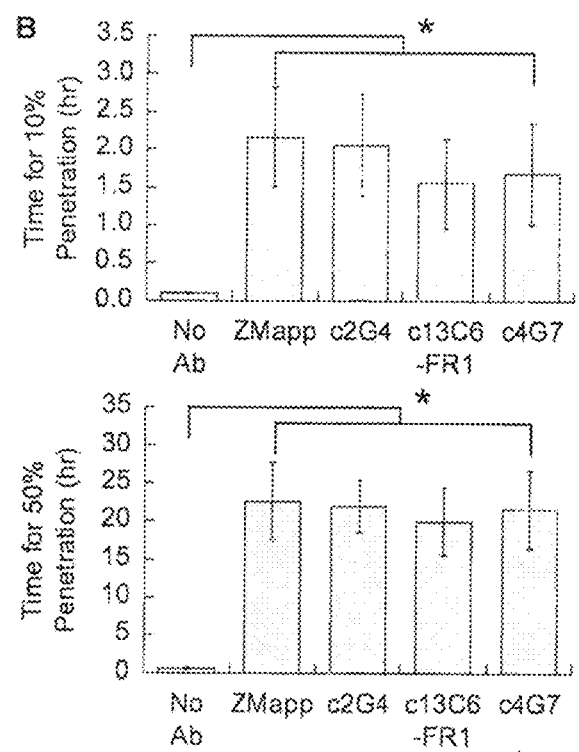

Along the major conducting airways, the approximate thickness of mucus lining the bronchial airways is ~50 μm, and the entire mucus blanket can be renewed in as little as 15-30 minutes. Therefore, we performed a first passage time estimate, using the measured diffusivities of individual VLP in AM to determine the time needed for viruses to diffuse across a 50 μm thick AM layer. We found that upon airway deposition, nearly 10% of Ebola virions can penetrate the luminal AM layer within approximately 5 minutes, and nearly 50% can penetrate the AM layer in as little as 30 minutes (FIG. 17B). These results suggest limiting rapid Ebola penetration of AM may be an important strategy to reduce Ebola infection by decreasing the flux of virions reaching the underlying airway epithelium.

Figures 16A, 16B, 16C:
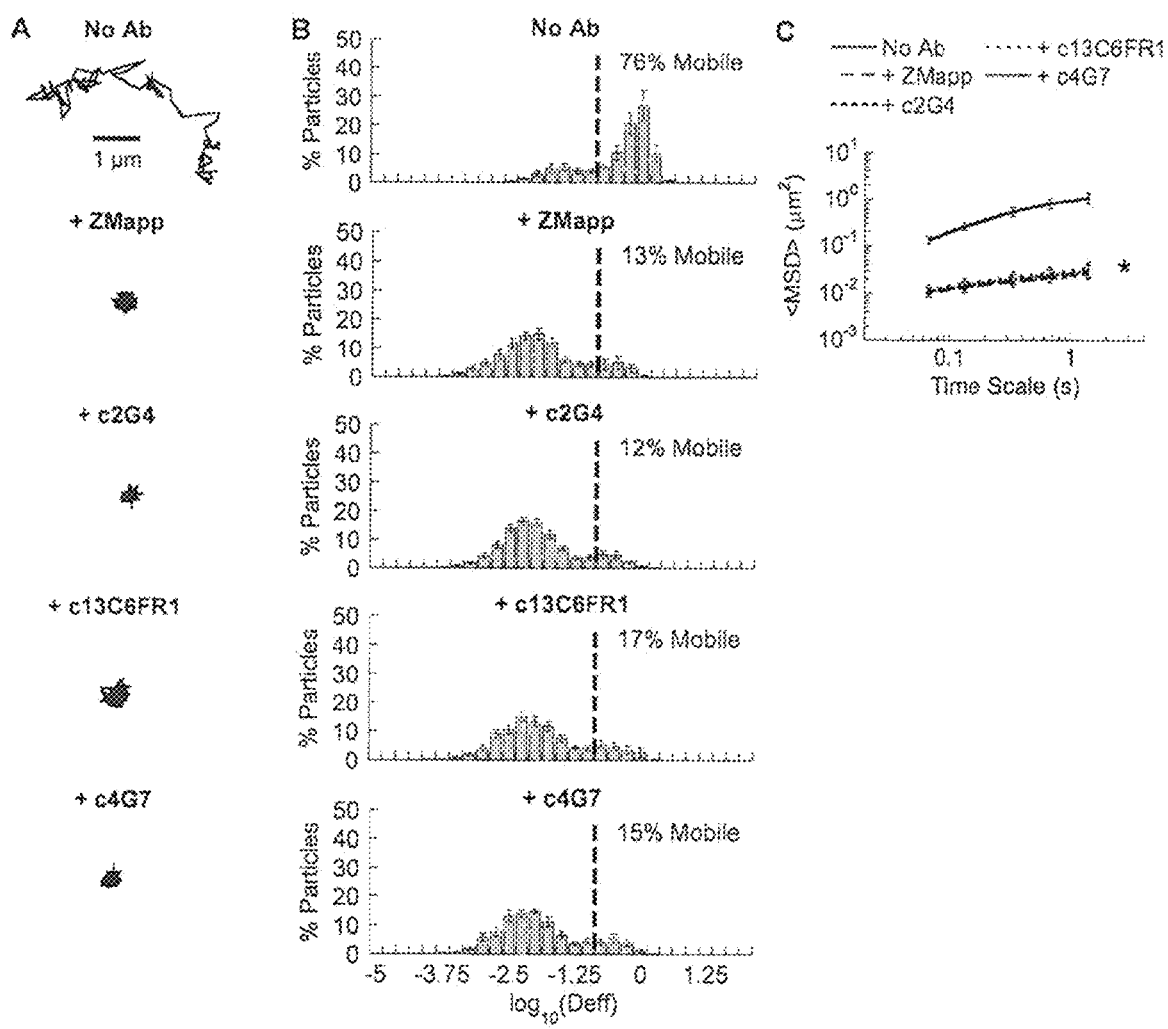
FIGS. 16A-16C show diffusion of Ebola VLP in human AM that is untreated (No Ab) or treated with either ZMapp™ or individual Ebola-binding IgG (c2G4, c16C6FR1, c4G7). (A) Representative trajectories for VLP exhibiting effective diffusivities within one SEM of the ensemble average at a time scale of 0.2667 s. (B) Ensemble-averaged geometric mean square displacements (<MSD>) as a function of time scale. (C) Distributions of the logarithms of individual particle effective diffusivities ($D_{eff}$) at a time scale of 0.2667 s. Log $D_{eff}$ values to the left of the dashed line correspond to particles with displacements of less than approximately 200 nm (i.e., roughly twice the particle diameter) within 0.2667 s or $D_{eff}$ approximately 20-fold reduced from theoretical diffusivity in water. Data represent the ensemble average of 8-9 independent AM specimens. Error bars represent standard error of the mean (SEM). * indicates a statistically significant difference compared to No Ab (p<0.05) based on a one-tailed, paired Student's t-test.

The treatment of human airway mucus with ZMapp™ may immobilize Ebola virus-like particles. While total Ig and IgG isotype levels varied substantially across AM samples (Table 5), the rapid diffusion of Ebola VLP in AM was remarkably consistent, suggesting endogenous antibody did not impact Ebola VLP mobility. We next evaluated whether Ebola-binding IgG, in the form of the three chimeric monoclonal antibody (mAb) cocktail ZMapp™, could enhance the diffusional barrier properties of AM against Ebola. The addition of modest levels of Ebola-binding IgG into AM effectively reduced the mobility of Ebola VLP, with the majority of VLP moving much less than their diameters over at least 20 s (FIG. 16A). Indeed, the <$D_{eff}$> of Ebola VLP in ZMapp™-treated AM decreased by ~27-fold compared to <$D_{eff}$> in the same native AM secretions without Ab (FIG. 17A). Likewise, the fraction of mobile VLP was reduced from 90% to 29% (FIG. 16B), while <MSD> was over 260-fold lower than theoretical VLP speeds in buffer (FIG. 16C; at a time scale of 0.2667 s). The increased hindrance to rapid diffusion is also evident from the log <MSD> vs. log time scale slope a of 0.34. Fluorescence of VLP in both native (i.e., Ab-free) and ZMapp™-treated AM appeared identical in both size and brightness, suggesting ZMapp™ did not induce agglutination (i.e., agglomeration of multiple Ebola VLP). Thus, the decrease in measured Ebola VLP mobility is most likely attributed to immobilization of individual VLP due to polyvalent interactions between the array of VLP-bound Ab and mucins.

To determine whether any particular mAb (c2G4, c116C6FR1, c4G7) within the ZMapp™ cocktail may confer superior "muco-trapping" potency, we measured the mobility of Ebola VLP in different aliquots of the same AM specimens treated with the individual mAb. Interestingly, all three mAb, including one with poor neutralizing activity against Ebola, were similarly effective in reducing the mobility of Ebola VLP in AM, as shown in FIG. 16A. Relative to the control with no Ab and similar to with ZMapp™, the <$D_{eff}$> of Ebola VLP was reduced by ~28-, 22-, and 25-fold in AM treated with c2G4, c116C6FR1 and c4G7, respectively. Similarly, the fraction of mobile Ebola VLP was reduced to 27%, 33% and 30%, respectively.

To better illustrate how the aforementioned changes in VLP mobility might alter the flux of virions reaching target cells, we performed first passage time analysis as described above. The predicted time for 10% of Ebola VLP to diffuse across a 50 m thick mucus layer increased from ~0.1 hours (i.e., approximately 5 minutes) for native AM to 2.2, 2.1, 1.6, and 1.7 hours for ZMapp™-, c2G4-, c116C6FR1- and c4G7-treated AM, respectively. Similarly, the estimated time for 50% of VLP to cross the mucus layer increased from 0.5 hours for native AM to 23, 22, 20, and 22 hours, respectively. Since mucociliary clearance occurs on the order of 15-30 minutes, these results suggest that, with the exception of native AM that is devoid of Ebola-binding IgG, the vast majority of Ebola virions would be quickly trapped and eliminated from ZMapp™-treated airways before they could penetrate AM.

Figures 18A, 18B, 18C, 18D, 18E:
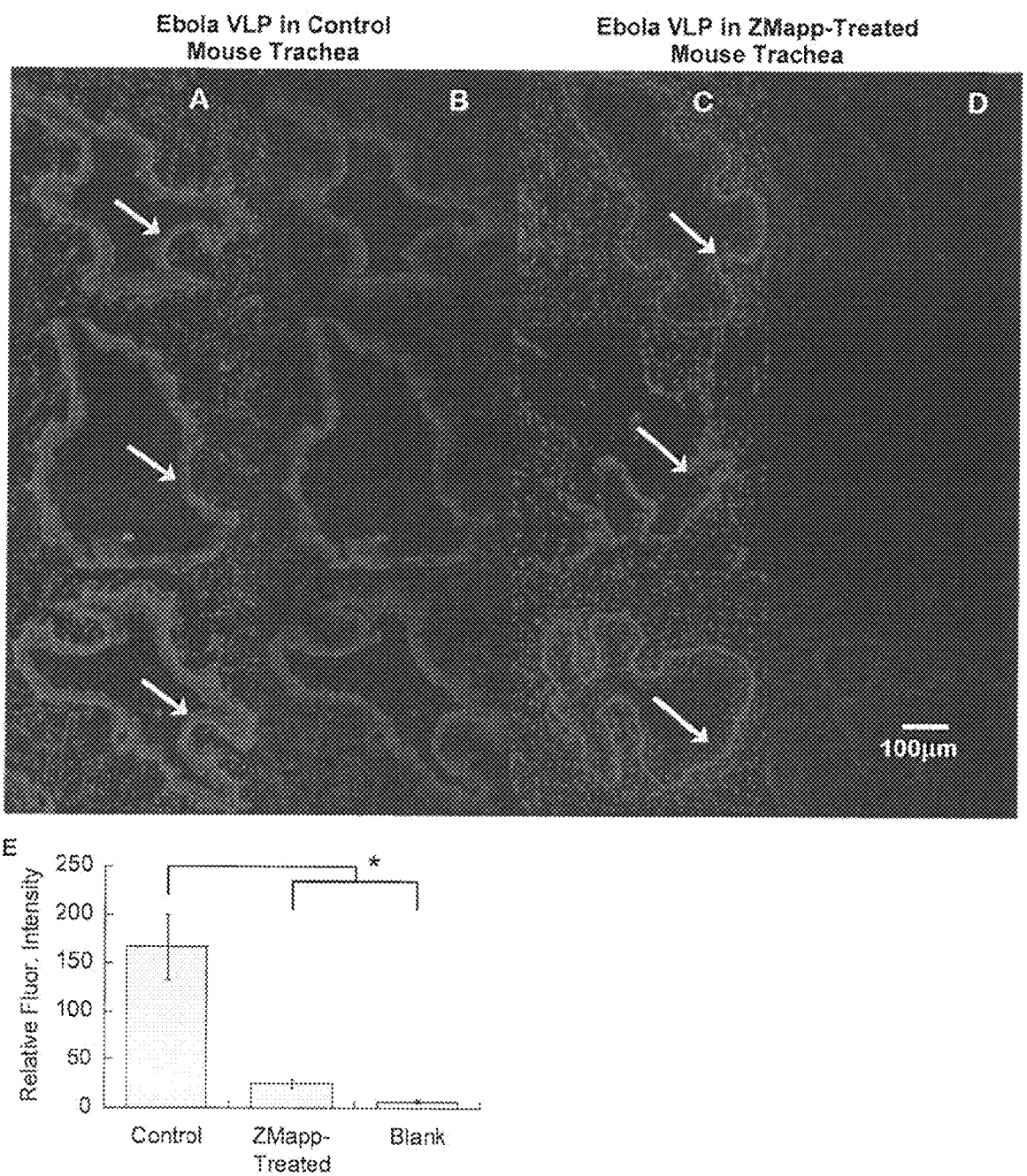
FIGS. 18A-18E show (e.g., FIGS. 18A-18D) representative transverse 50 µm thick frozen tissue sections showing the distribution of Ebola VLP in the mouse trachea treated with (A, B) PBS or (C, D) ZMapp™. Red corresponds to Ebola VLP, and blue corresponds to DAPI-stained cell nuclei. Arrows indicate the inner lining of the trachea. (E) Quantification of Ebola VLP signal in mouse trachea treated with PBS ("Control") or ZMapp™ ("ZMapp-Treated") compared to blank tissue ("Blank"). Data represent n=3 mice per group with on average 10 tissue sections quantified per mouse. Error bars represent standard error of the mean (SEM). * indicates a statistically significant difference (p<0.05) based on a two-tailed Student's t-test assuming unequal variance.

The topical delivery of ZMapp™ may facilitate the rapid elimination of Ebola from the lung airways: Lastly, we sought to evaluate whether ZMapp™-induced trapping of viruses in mucus secretions ex vivo would translate to an improved barrier against Ebola penetration of AM and consequently altered distribution in the lung airways in vivo. Using an aerosol delivery device (e.g., PennCentury microsprayer), we administered ZMapp™ or PBS to the mouse lung, followed by addition of fluorescent Ebola VLP 30 minutes later. In control mice treated, we observed substantial red fluorescence associated with Ebola VLP throughout the lung airways, including fluorescence indicative of mucosal penetration and accumulation in the underlying airway epithelium, as shown in FIGS. 17A and 17B. In contrast, far fewer Ebola VLP were present in the airways of mice treated with ZMapp™ (FIGS. 18C, 18D), presumably since VLP were trapped in the luminal mucus and rapidly cleared. Indeed, fluorescence levels in lung tissues of ZMapp™-treated mice were almost 7-fold lower than those in control mice, and only 3.5-fold above background. These results are consistent with previous observations that nanoparticles that bind to mucin mesh fibers are unable to penetrate the mucus layer and reach the underlying epithelium.

Ebola VLP readily penetrate fresh human AM secretions, but can be effectively immobilized in AM by antigen-specific IgG (e.g., ZMapp™). Trapping in turn facilitated rapid elimination of Ebola VLP from the mouse airways. Although Ebola is generally not considered an airborne pathogen, aerosol transmission of Ebola virus is biologically plausible. Ebola virus is present in saliva, feces, blood, and other body fluids that can be aerosolized through Ebola symptoms (e.g., coughing, vomiting, diarrhea) and through health care delivery (e.g., intubation, suctioning, delivery of nebulized medications). Large droplets from a human sneeze can travel up to 1-2 m, while smaller droplets can travel up to 6-8 m away within seconds to a few minutes. Studies have also found Ebola to survive in aerosol form for tens of minutes if not hours. Ebola can initiate infection in cells present in the respiratory tract, and fatal respiratory infection has been observed in guinea pigs and non-human primates following intranasal and aerosol exposure. Furthermore, Ebola transmission has been shown between infected and healthy macaques and between infected pigs and macaques without direct physical contact, likely via aerosol or droplet transmission, although potential cross-contamination during animal husbandry practices could not be discounted entirely. A study frequently cited in arguments against airborne transmission found no detectable Ebola transmission when monkeys inoculated intramuscularly were housed in neighboring open-barred cages separated by a Plexiglas® divider that prevented direct contact; nevertheless, high viral titers were only detected in the blood, suggesting virus titers in the lungs of these animals may not have achieved the critical titers necessary for respiratory transmission before the animals succumbed to the systemic effects of infection. In contrast, recent studies in humans have reported substantial quantities of Ebola in respiratory secretions, and pathology studies have also found viral antigen in lung tissue. Finally, aerosol dissemination of weaponized forms of these viruses, a version of which has reportedly already been developed for Marburg virus, presents a significant threat to both the military and potentially the general public. Altogether, these reports substantiate continued concern over aerosol transmission of Ebola virus, and the need to explore strategies to prevent and treat Ebola transmission at mucosal membranes, particularly if Ebola or other filoviruses become weaponized.

While the secretion of mucus can increase in response to infection, mucus is generally viewed as a passive rather than adaptive barrier against pathogens, and consequently overlooked in most studies of mucosal infection. The notion that Ab can work in tandem with mucus to reinforce the diffusional barrier properties of mucus has remained largely unexplored, despite the fact that large quantities of Ab, including both IgG and IgA, are secreted into AM. Here, in good agreement with our recent discovery that IgG can trap HSV-1 in human cervicovaginal mucus, we showed that Ebola-binding mAb, in the form of ZMapp™, were able to facilitate effective trapping of the majority of Ebola VLP in AM. Ab-mediated trapping of Ebola VLP markedly reduced the fraction of virions predicted to penetrate the mucus layer over the first few minutes of exposure. Since trapped viruses are quickly eliminated by natural mucociliary clearance in the airways, ZMapp™-mediated trapping of Ebola would likely reduce the total flux of viruses arriving at the airway epithelium and thus the likelihood and/or severity of infection, rather than simply delaying the onset of infection. Consistent with this hypothesis, we observed topical delivery (e.g., via aerosol) of ZMapp™ into the mouse lung greatly reduced the amount of fluorescent Ebola VLP retained in the conducting airways within 30 minutes. IgG-mediated trapping of viruses in mucus appears to be a universal protective immune function across different mucosal surfaces that enables protection directly at the portals of entry for viral transmission.

The concept of mucosal Ab prophylaxis and/or therapy based on Ab designed to work together with mucus to trap pathogens represents a unique and complementary approach in the arsenal of protective methods against infectious disease. First, the concept radically shifts the first line of defense against respiratory viruses to extracellular mucus gels instead of cellular targets, which is especially important against viruses that are either exceptionally virulent (e.g., Ebola) and/or without a cure (e.g., HIV, Ebola). Second, Ab that trap viruses in mucus need not bind to neutralizing epitopes; this greatly broadens the potential antigen targets that can be exploited to achieve protection. Indeed, one of the mAb in the ZMapp™ cocktail is actually a poor neutralizer. Third, since the viral load during the transmission episode at mucus membranes is likely low, the overall dose of mAb needed at mucosal surfaces, either before or immediately following a high-risk exposure event, may be substantially less than the mAb dose needed to treat a proliferating systemic infection. Thus, ZMapp™ delivered topically may be a particularly useful preventative measure or emergency intervention for populations at the highest risks of acquiring Ebola infections, such as healthcare workers, for reducing both the odds of becoming sick as well as the viral load entering the circulation following an exposure event.

Example 6

Blocking Penetration of Respiratory Syncytial Viruses in Human Airway Mucus

In the U.S., RSV is the leading cause of bronchiolitis, pneumonia and viral death, with >3.5 million RSV infections and >125,000 hospitalizations in children under 2 each year. RSV infection in nursing homes ranges between 5-10%, leading to 177,000 hospitalizations and significant rates of pneumonia (10-20%) and death (~14,000 deaths annually) among the infected elderly. Palivizumab (also referred to as SYNAGIS) is a mAb developed for treatment of RSV. Despite its modest efficacy in reducing risk of RSV-associated hospitalization, SYNAGIS is only given to a very small subset of the pediatric population. Per the CDC, there is currently no treatment for RSV.

SYNAGIS is typically applied by injection. Although it may decrease the risk of developing RSV, SYNAGIS is not effective in treating RSV infection. Surprisingly, based on the inventions described herein, this is likely because the amount of mAb extravasating into the airways is inadequate. In other words, there is likely just enough mAb reaching the lung lumen with IM injection to modestly reduce the rate of acquiring RSV infection, especially since the viral titers of typical RSV exposure are low. However, once infection is established, the amount of mAb is inadequate to contain the spread of higher titers of RSV. Given the unique pathophysiology of RSV that sheds infectious virions into the lumen, we believe concentrating mAb in the lung would be a more effective therapeutic approach than systemic or IM delivery. In cotton rat studies, pulmonary delivery of polyclonal IgG was 160-fold more effective in treating RSV than intramuscular delivery.

Figures 19A, 19B:
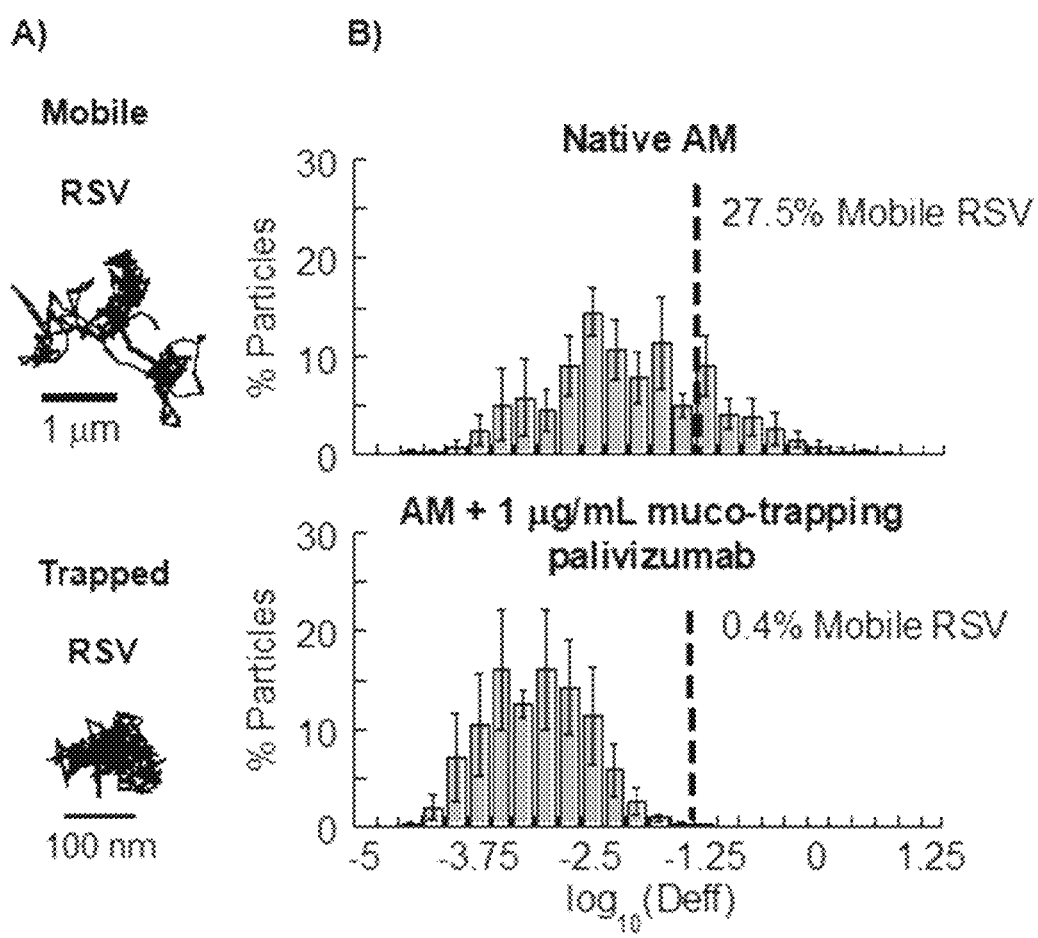
FIGS. 19A-19B show diffusion of RSV in human AM. (A) Representative traces of mobile vs. trapped RSV. (B) Distributions of the logarithms of individual particle effective diffusivities (Deff).
Figure 20A:
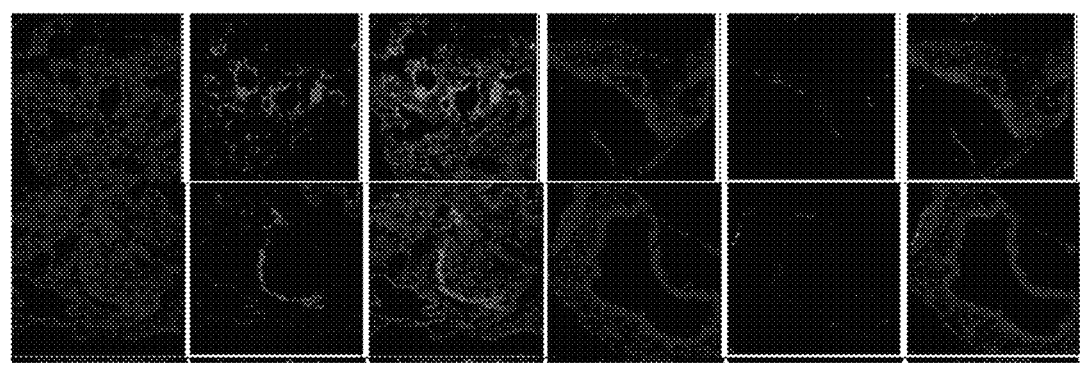
FIGS. 20A-20B show (A) cryosections of mouse airways inoculated with fluorescent RSV (red) treated with either PBS or RespiraClear, an aerosol formulation of mAb against RSV that is a "muco-trapping" antibody.
Figure 20B:
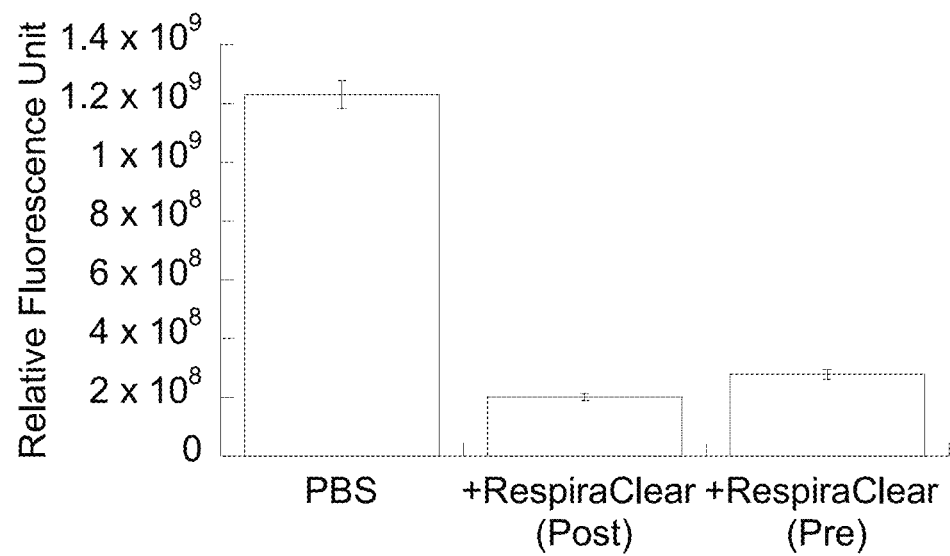
Figure 21:
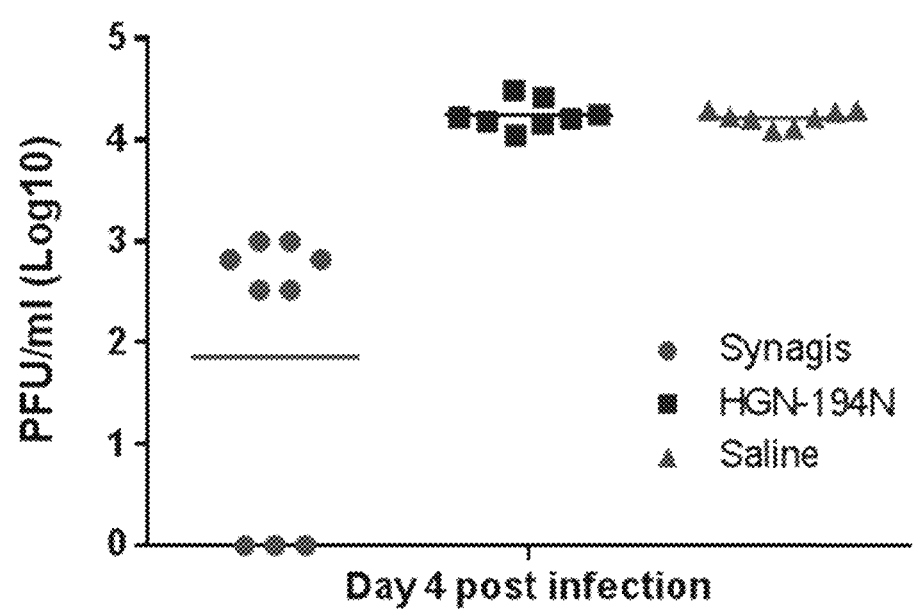
FIG. 21 shows the reduction in infectious viral titers in the cotton rat lung after intranasal administration of antibody.
Figure 22A:
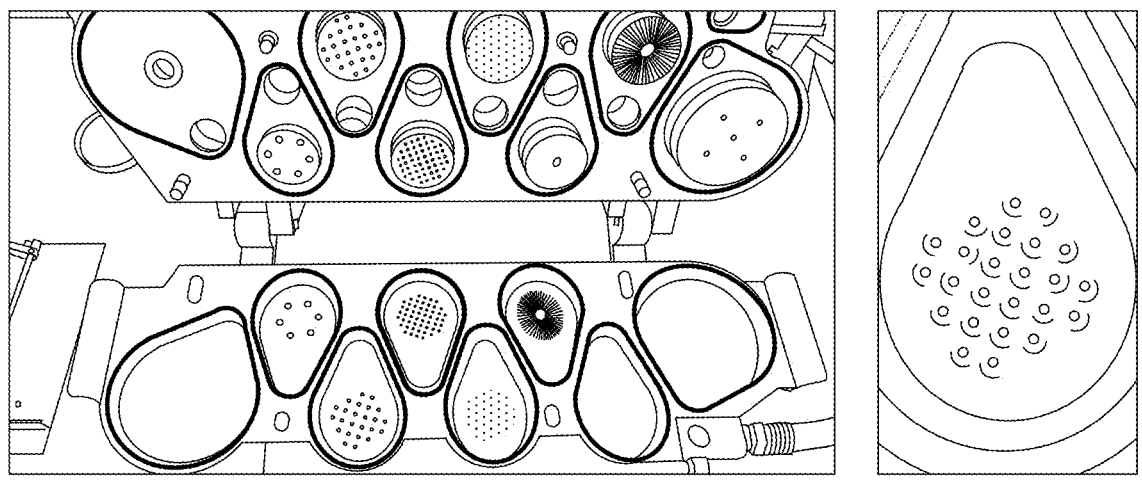
FIGS. 22A-22B show (A) photographs of a next generation impactor (NGI) for size verification of aerosol particles, following Privigen deposition. The right photograph is a zoomed in image of stage three of the NGI. (B) Inertial impaction results of nebulized Privigen when operating a NGI at 15 L/min for three minutes. Error bars represent one standard deviation above and below the mean (n=3).
Figure 22B:
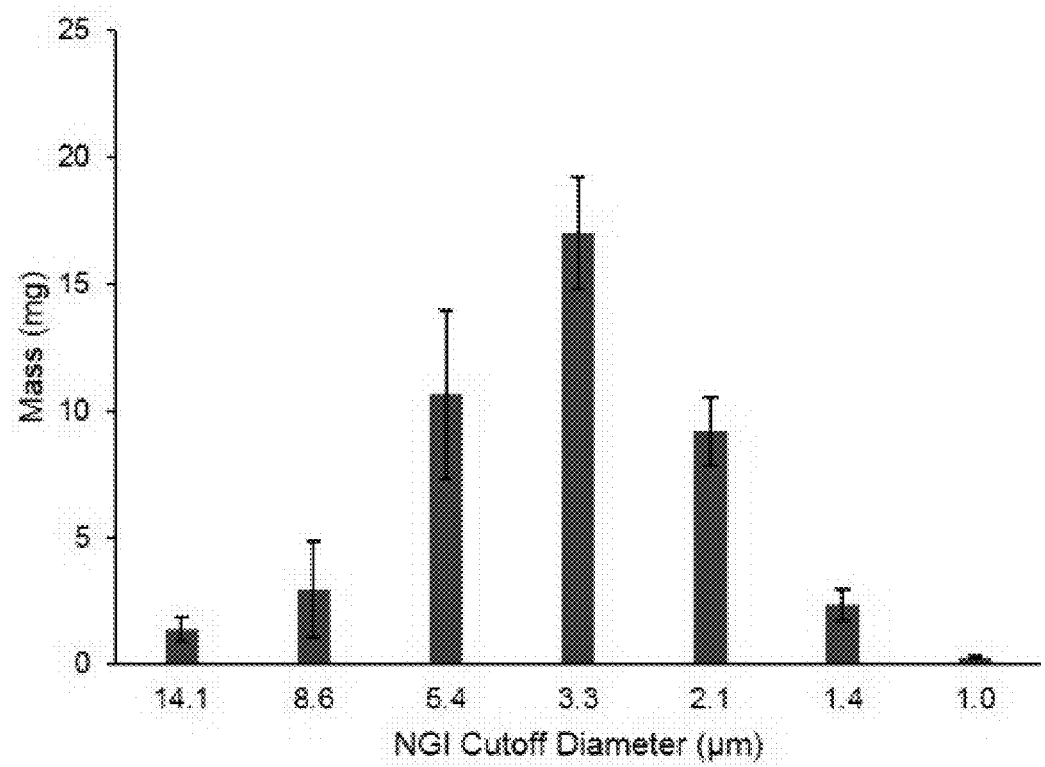

To visualize individual RSV virions in AM, we fluorescently tagged RSV by conjugating AF488 dye to the virus surface, which reduced the total mAb that could bind RSV by only ~10%-20%. When mixed into fresh, physiological human AM collected from intubated endotracheal tubes, a substantial fraction of RSV (~28% 7%) exhibited rapid diffusion in all 12 independent AM specimens tested (FIGS. 19A-19B). The large fraction of trapped RSV (all RSV to the left of the dashed line) is likely due to endogenous RSV-binding Ab in adult AM; we expect the fraction of mobile RSV would be higher in AM from young children, who are less likely to have substantial endogenous RSV-binding Ab. In aliquots of the same AM specimens, we mixed into AM our "muco-trapping" palivizumab to a final concentration of 1 μg/mL, and found that virtually all RSV became immobilized (i.e., moved less than their diameter (d 100 nm as indicated by the dashed line) over at least the course of the 20 s movies). We observed similar trapping potency down to 50 ng/mL. Addition of a non-binding IgG control (a human $IgG_1$ against polyethylene glycol (PEG)), did not slow the diffusion of RSV. As described above, virions can be effectively immobilized in human AM by virion-binding Ab.

The "muco-trapping" palivizumab described herein includes the heavy and light chain variable regions of palivizumab and includes a glycosylation pattern on the Fc region that enhances mucous trapping. For example, the muco-trapping palivizumab may be a population of mAb in which at least some percentage (e.g., at least 50%, at least 60%, etc.) of the mAb having the heavy and/or light chain variable regions of palivizumab (or a derivative of palivizumab) contains a glycosylation pattern of G0/G0F (i.e. GnGn) such that they facilitate trapping of viruses in mucus. For example, in some variations the population of muco-trapping antibody (e.g., muco-trapping palivizumab) has at least 60% of the recombinant antibodies in the population having a glycosylation pattern comprising the biantennary core glycan structure Manα1-6(Manα1-3)Manβ1-4GlcNAcβ1-4GlcNAcβ1 with terminal N-acetylglucosamine on each branch.

Further, muco-trapping mAb against RSV rapidly eliminates RSV from mouse airways. To verify that trapping in mucus facilitates rapid elimination from the airways, we performed an in vivo study where fluorescent RSV was dosed to the airways of Balb/c mice (8-10 weeks), followed by either PBS or muco-trapping Ab against RSV, and finally euthanasia and cryo-sectioning of the trachea and airways 30 mins later. As shown by cryosectioned images, topical delivery of the RSV-trapping IgG effectively reduces the amount of RSV remaining in the mouse airways as little as 30 mins post-delivery compared to PBS control, reaching levels comparable to mouse treated with the same RSV-trapping IgG 15 mins prior to RSV inoculation (n=6; FIGS. 20A-20B). Similar results to PBS were observed with topical delivery of control IgG (n=2). These results underscore the ability of muco-trapping IgG against RVS in enabling rapid elimination of RSV from infected airways.

Intranasally dosed "muco-trapping" mAb against RSV effectively reduces infectious RSV titers in cotton rats. Based on our observations above that muco-trapping mAb against RSV was able to trap RSV in human AM and facilitate rapid elimination of RSV in the mouse lung, we next proceeded to evaluate whether topical delivery of the same mAb can be used to treat RSV infections. Cotton rats remain the gold standard as a first in vivo model for RSV infection. In this study, we inoculated RSV Strain A2 (100 μL; $1\times10^6$ PFU per rat) on Day 0. After a 48 hr period to allow the infection to proliferate, we treated 3 groups of mice with either 2 daily doses (i.e., once each on Day 2 and Day 3) of the muco-trapping mAb against RSV (possessing same Fab as SYNAGIS, modified to have enhanced mucosal trapping as described herein; n=9), control IgG (e.g., HGN-194, a mAb against HIV; n=8), or vehicle control (e.g., saline; n=8). All treatments were administered intranasally, and lungs were harvested from all rats on Day 4, snap frozen, and finally homogenized for viremia analysis via immunoplaque assay. An anti-RSV antibody having enhanced mucosal trapping (Muco-trapping mAb) mediated on average >100-fold reduction in infectious viral titers in the cotton rat lung, including 3 rats that showed no detectable viremia, underscoring the potential effectiveness of this treatment. This is illustrated in, FIG. 21.

To demonstrate that we can deliver mAb to the lung airways via nebulization, we performed initial characterization of nebulization using PARI's off-the-shelf eRapid system. Using the Copley Next Generation Impactor (NGI), shown in FIG. 22A. We tested the eRapid device operated at 15 L/min for 3 minutes using a human IVIG solution (Privigen®) at 25 mg/mL. Analysis of inertial impaction results, based on distribution of antibody mass with respect to impaction stage cutoff diameter, shows a Mass Median Aerodynamic Diameter (MMAD) of 4.5±0.21 μm (GSD=1.57±0.01), with a fine particle fraction of 66.5±6.2% (indicative of the percentage of mass deposited on stage 3 of the NGI and below which, at 15 L/min, has a cutoff diameter of 5.39 μm). These results underscore our ability to generate aerosol droplets using a vibrating mesh nebulizer in a size range that support lung mucous deposition (1-5 μm range). The MMAD of 4.5 μm matches well with the value presented by the eFlow nebulizer manufacturer. To further validate that the IgG is stably nebulized, we performed gel electrophoresis on the nebulized IgG. We did not observe separation of the heavy and light chains or aggregation, and the concentration of IgG recovered was at 93%-108% of the input concentration. These results validate the ability to deliver RespiraClear via PARI's nebulizers.

What is claimed is:

1. A method for immobilizing or inhibiting a sexually transmitted infection by a pathogen, or reducing pathogen load in a subject in need thereof, the method comprising administering to a mucosal surface of the subject a recombinant antibody with a specific affinity for the pathogen, the recombinant antibody comprising a human or humanized Fc region, wherein the recombinant antibody comprises a population of antibodies in which at least 40% comprise an oligosaccharide having a GOF glycosylation pattern comprising a biantennary core glycan structure of Manα1-6 (Manα1-3)Manβ1-4GlcNAcβ1-4GlcNAcβ1 with a fucose residue and a terminal N-acetylglucosamine, wherein the terminal N-acetylglucosamine is on each branch, that enhances the trapping potency of the recombinant antibody in mucus, so that the recombinant antibody binds to the pathogen to form an antibody/pathogen complex that is trapped in the subject's mucus.

2. The method of claim 1, wherein the recombinant antibody comprises an N-linked glycosylation site on the Fc region of the antibodies to which the oligosaccharide is attached.

3. The method of claim 1, wherein 50% or more of the recombinant antibodies in the population have a glycosylation pattern comprising the biantennary core glycan structure Manα1-6(Manα1-3)Manβ1-4GlcNAcβ1-4GlcNAcβ1 with the fucose and with the terminal N-acetylglucosamine on each branch.

4. The method of claim 1, wherein the recombinant antibody is configured to bind to a non-neutralizing epitope of the pathogen.

5. The method of claim 1, wherein administering comprises administering a dose at a sub-neutralization dose level.

6. The method of claim 1, further comprising reducing the mobility of the pathogen in the patient's mucus to no more than about 50% relative to its mobility in water.

7. The method of claim 1, further comprising reducing the percentage of pathogen that can penetrate the patient's mucus by at least 10%.

8. The method of claim 1, wherein the recombinant antibody is a human or humanized IgG or IgM monoclonal antibody, or a fragment thereof.

9. The method of claim 1, wherein the recombinant antibody is formulated as a topical composition.

10. The method of claim 1, wherein the pathogen is selected from: *Neisseria gonorrhoeae* (gonorrhea); *Chlamydia trachomatis* (*chlamydia*, lymphogranuloma venereum); *Treponema pallidum* (syphilis); *Haemophilus ducreyi* (chancroid); *Klebsiella granulomatis* or *Calymmatobacterium granulomatis* (donovanosis), *Mycoplasma genitalium, Ureaplasma urealyticum* (mycoplasmas); human immunodeficiency virus HIV-1 and HIV-2 (HIV, AIDS); HTLV-1 (T-lymphotrophic virus type 1); herpes simplex virus type 1 and type 2 (HSV-1 and HSV-2); Epstein-Barr virus; cytomegalovirus; human herpesvirus 6; varicella-zoster virus; human papillomaviruses (genital warts); hepatitis A virus, hepatitis B virus, hepatitis C virus (viral hepatitis); molluscum contagiosum virus (MCV); Trichomona *vaginalis* (trichomoniasis); and *Candida albicans* (vulvovaginal candidiasis).

11. The method of claim 1, wherein the pathogen is herpes simplex virus type 1 or type 2.

12. A method of immobilizing a sexually transmitted pathogen in mucus of a subject's reproductive tract, the method comprising administering to the subject, via a topical route, a population of recombinant antibodies with a specific affinity for the pathogen, the recombinant antibodies comprising a human or humanized Fc region, wherein at least 40% of the recombinant antibodies comprise an oligosaccharide having a glycosylation pattern comprising the biantennary core glycan structure Manα1-6(Manα1-3) Manβ1-4GlcNAcβ1-4GlcNAcβ1 with a fucose and a terminal N-acetylglucosamine, wherein the terminal N-acetylglucosamine is on each branch to enhance the trapping potency of the recombinant antibody in mucus, so that the recombinant antibodies bind to the pathogen to form an antibody/pathogen complex that is trapped in the subject's mucus.

13. The method of claim 12, wherein the recombinant antibodies are configured to bind to a non-neutralizing epitope of the pathogen.

14. The method of claim 12, wherein administering comprises administering a dose at a sub-neutralization dose level.

15. The method of claim 12, wherein the recombinant antibodies comprise N-linked glycosylation sites on the Fc region of the antibodies to which the oligosaccharide is attached.

16. The method of claim 12, further comprising reducing the mobility of the pathogen to no more than about 50% relative to its mobility in water.

17. The method of claim 12, further comprising reducing the percentage of pathogen that can penetrate mucus by at least 10%.

18. The method of claim 12, wherein the recombinant antibody is a human or humanized IgG or IgM monoclonal antibody, or a fragment thereof.

19. The method of claim 12, wherein the recombinant antibody is formulated as a gel, lotion, cream, or ointment.

20. The method of claim 12, wherein at least 50% of the recombinant antibodies in the population have a glycosylation pattern comprising the biantennary core glycan structure Manα1-6(Manα1-3)Manβ1-4GlcNAcβ1-4GlcNAcβ1 with terminal N-acetylglucosamine on each branch.

21. The method of claim 12, wherein the pathogen is selected from: *Neisseria gonorrhoeae* (gonorrhea); *Chla-* mydia trachomatis (*chlamydia*, lymphogranuloma venereum); *Treponema pallidum* (syphilis); *Haemophilus ducreyi* (chancroid); *Klebsiella granulomatis* or *Calymmatobacterium granulomatis* (donovanosis), *Mycoplasma genitalium, Ureaplasma urealyticum* (mycoplasmas); human immunodeficiency virus HIV-1 and HIV-2 (HIV, AIDS); HTLV-1 (T-lymphotrophic virus type 1); herpes simplex virus type 1 and type 2 (HSV-1 and HSV-2); Epstein-Barr virus; cytomegalovirus; human herpesvirus 6; varicella-zoster virus; human papillomaviruses (genital warts); hepatitis A virus, hepatitis B virus, hepatitis C virus (viral hepatitis); molluscum contagiosum virus (MCV); Trichomona *vaginalis* (trichomoniasis); and *Candida albicans* (vulvovaginal candidiasis).

22. The method of claim 12, wherein the pathogen is herpes simplex virus type 1 or type 2.

23. A method for inhibiting a sexually transmitted pathogen in mucus of a subject's reproductive tract, the method comprising immobilizing the pathogen by administering to the subject a population of recombinant antibody in which at least 40% comprise an oligosaccharide having a GOF glycosylation pattern comprising a biantennary core glycan structure of Man$\alpha$1-6(Man$\alpha$1-3)Man$\beta$1-→GlcNAc$\beta$1-4GlcNAc$\beta$1 with a fucose reside and a terminal N-acetylglucosamine, wherein the terminal N-acetylglucosamine is on each branch, wherein the recombinant antibody has a specific affinity for the pathogen so that the recombinant antibody is trapped in the subject's mucus, the recombinant antibody comprising a human or humanized Fc region, wherein the recombinant antibody comprises an oligosaccharide having a glycosylation pattern that enhances the trapping potency of the recombinant antibody in mucus.

\* \* \* \* \*

UNITED STATES PATENT AND TRADEMARK OFFICE
CERTIFICATE OF CORRECTION

PATENT NO. : 11,897,939 B2
APPLICATION NO. : 17/066874
DATED : February 13, 2024
INVENTOR(S) : Lai et al.

It is certified that error appears in the above-identified patent and that said Letters Patent is hereby corrected as shown below:

In the Specification

Column 7, Line 57: Please correct "a becomes" to read --α becomes--

Column 35, Line 65: Please correct "50 L" to read --50 µL--

Column 36, Line 2: Please correct "25 L" to read --25 µL--

Column 36, Line 14: Please correct "25 L" to read --25 µL--

Column 36, Line 55: Please correct "100 L" to read --100 µL--

Column 37, Line 30: Please correct "200 g" to read --200 µg--

Column 37, Lines 56-57: Please correct "50 L/well" to read --50 µL/well--

Column 38, Line 4: Please correct "210 L" to read --210 µL--

Column 38, Line 45: Please correct "0.156 m/pixel" to read --0.156 µm/pixel--

Column 39, Line 2: Please correct "and a is" to read --and α is--

Column 39, Line 30: Please correct "20 L" to read --20 µL--

Column 39, Line 52: Please correct "50 L" to read --50 µL--

Column 55, Line 27: Please correct "0.45 m" to read --0.45 µm--

Column 57, Line 63: Please correct "$[x(t+\tau-x(t)]^2$" to read --$[x(t+\tau)-x(t)]^2$--

Signed and Sealed this
Seventh Day of May, 2024

Katherine Kelly Vidal
*Director of the United States Patent and Trademark Office*

CERTIFICATE OF CORRECTION (continued)
U.S. Pat. No. 11,897,939 B2

Column 58, Line 46: Please correct "$w_j$" to read --$w_i$--

Column 58, Line 49: Please correct "Gibco@" to read --Gibco®--

Column 60, Line 37: Please correct "slope a" to read --slope α--

Column 60, Line 62: Please correct "50 m" to read --50 μm--

Column 63, Line 34: Please correct "(~28% 7%)" to read --(~28%±7%)--

Column 63, Line 44: Please correct "d 100 nm" to read --d~100 nm--

In the Claims

Column 75, Line 24, Claim 1: Please correct "GOF" to read --G0F--

Column 75, Line 41, Claim 3: Please correct "fucose and" to read --fucose residue and--

Column 76, Line 34, Claim 12: Please correct "fucose and" to read --fucose residue and--

Column 76, Line 36, Claim 12: Please correct "branch to" to read --branch, to--

Column 77, Line 21, Claim 23: Please correct "GOF" to read --G0F--

Column 77, Line 23, Claim 23: Please correct "Manβ1-→GlcNAcβ1-" to read --Manβ1-4GlcNAcβ1- --

Column 77, Line 24, Claim 23: Please correct "fucose reside and" to read --fucose residue and--